(12) United States Patent
Guzman

(10) Patent No.: US 10,408,789 B2
(45) Date of Patent: Sep. 10, 2019

(54) DISEASE DETECTION SYSTEM AND METHOD

(71) Applicant: Princeton Biochemicals, Inc., Princeton, NJ (US)

(72) Inventor: Norberto A. Guzman, Princeton, NJ (US)

(73) Assignee: PRINCETON BIOCHEMICALS, INC., Princeton, NJ (US)

( * ) Notice: Subject to any disclaimer, the term of this patent is extended or adjusted under 35 U.S.C. 154(b) by 862 days.

(21) Appl. No.: 14/868,328

(22) Filed: Sep. 28, 2015

(65) Prior Publication Data

US 2016/0123925 A1    May 5, 2016

Related U.S. Application Data

(60) Division of application No. 12/713,966, filed on Feb. 26, 2010, now Pat. No. 9,146,234, which is a continuation of application No. 11/601,568, filed on Nov. 17, 2006, now Pat. No. 8,007,724, and a continuation of application No. 11/601,855, filed on Nov. 17, 2006, now Pat. No. 8,030,092, and a continuation of application No. 11/601,856, filed on Nov. 17, 2006, now Pat. No. 8,007,725, said application No. 11/601,568 is a division of application No. 10/728,499, filed on Dec. 5, 2003, now Pat. No. 7,329,388, said application No. 11/601,855 is a division of application No. 10/728,499, filed on Dec. 5, 2003, now Pat. No. 7,329,388, said application No. 11/601,856 is a division of application No. 10/728,499, filed on Dec. 5, 2003, now Pat. No. 7,329,388.

(60) Provisional application No. 60/518,186, filed on Nov. 7, 2003.

(51) Int. Cl.
*G01N 27/447* (2006.01)
*G01N 33/561* (2006.01)
*G01N 1/40* (2006.01)

(52) U.S. Cl.
CPC . *G01N 27/44756* (2013.01); *G01N 27/44708* (2013.01); *G01N 27/44743* (2013.01); *G01N 33/561* (2013.01); *G01N 1/405* (2013.01)

(58) Field of Classification Search
None
See application file for complete search history.

(56) References Cited

U.S. PATENT DOCUMENTS 5,637,458 A * 6/1997 Frankel ............... B01J 19/004
356/244
6,248,063 B1 * 6/2001 Barnhill ............... G01N 33/50
600/300
6,406,604 B1 * 6/2002 Guzman .......... G01N 27/44704
204/601

\* cited by examiner

*Primary Examiner* — Andrea S Grossman
(74) *Attorney, Agent, or Firm* — Porzio Bromberg & Newman P.C.

(57) ABSTRACT

An electrophoresis apparatus is generally disclosed for sequentially analyzing a single sample or multiple samples having one or more analytes in high or low concentrations. The apparatus comprises a relatively large-bore transport capillary which intersects with a plurality of small-bore separation capillaries and includes a valve system. Analyte concentrators, having antibody-specific (or related affinity) chemistries, are stationed at the respective intersections of the transport capillary and separation capillaries to bind one or more analytes of interest. The apparatus allows the performance of two or more dimensions for the optimal separation of analytes. The apparatus may also include a plurality of valves surrounding each of the analyte concentrators to localize each of the concentrators to improve the binding of one or more analytes of interest.

39 Claims, 34 Drawing Sheets

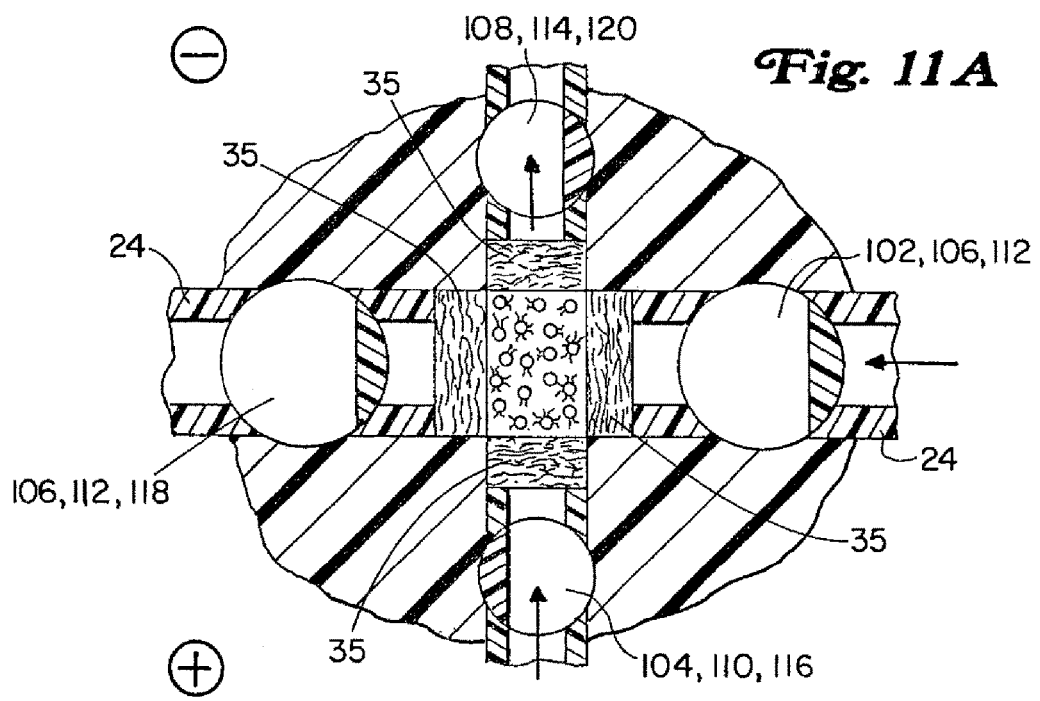
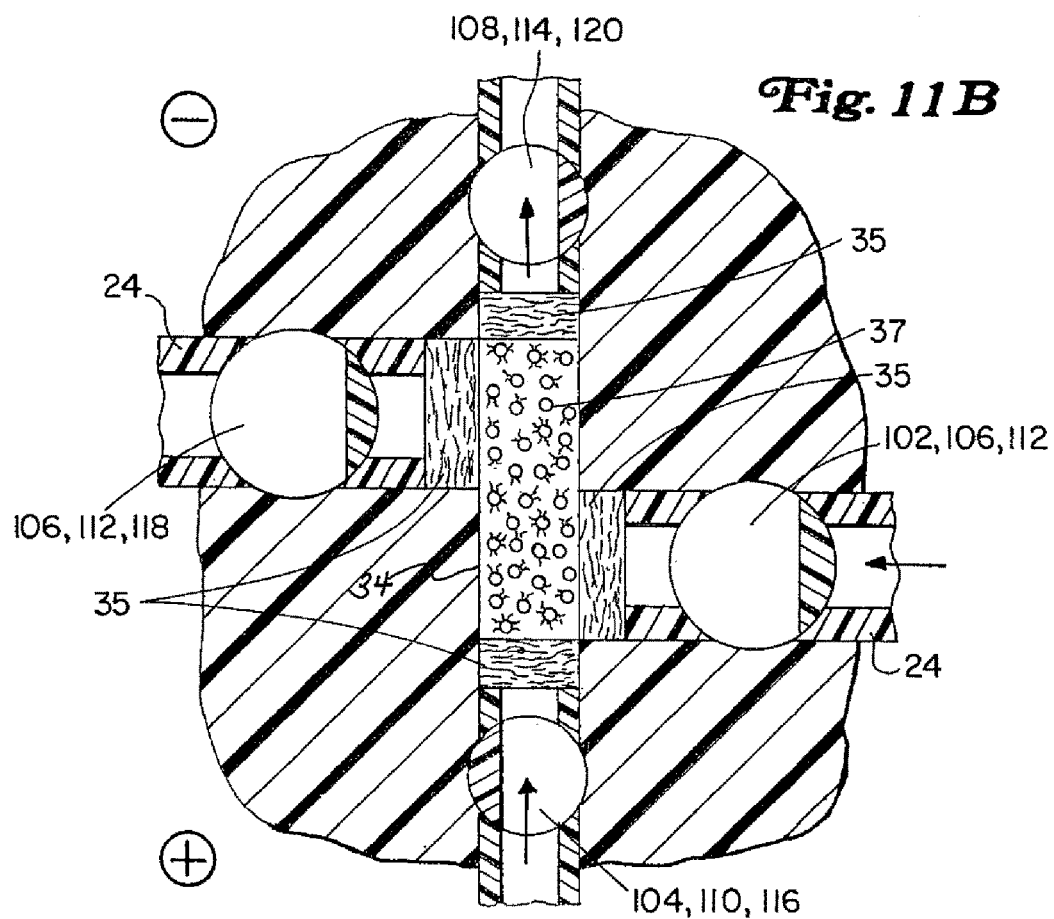

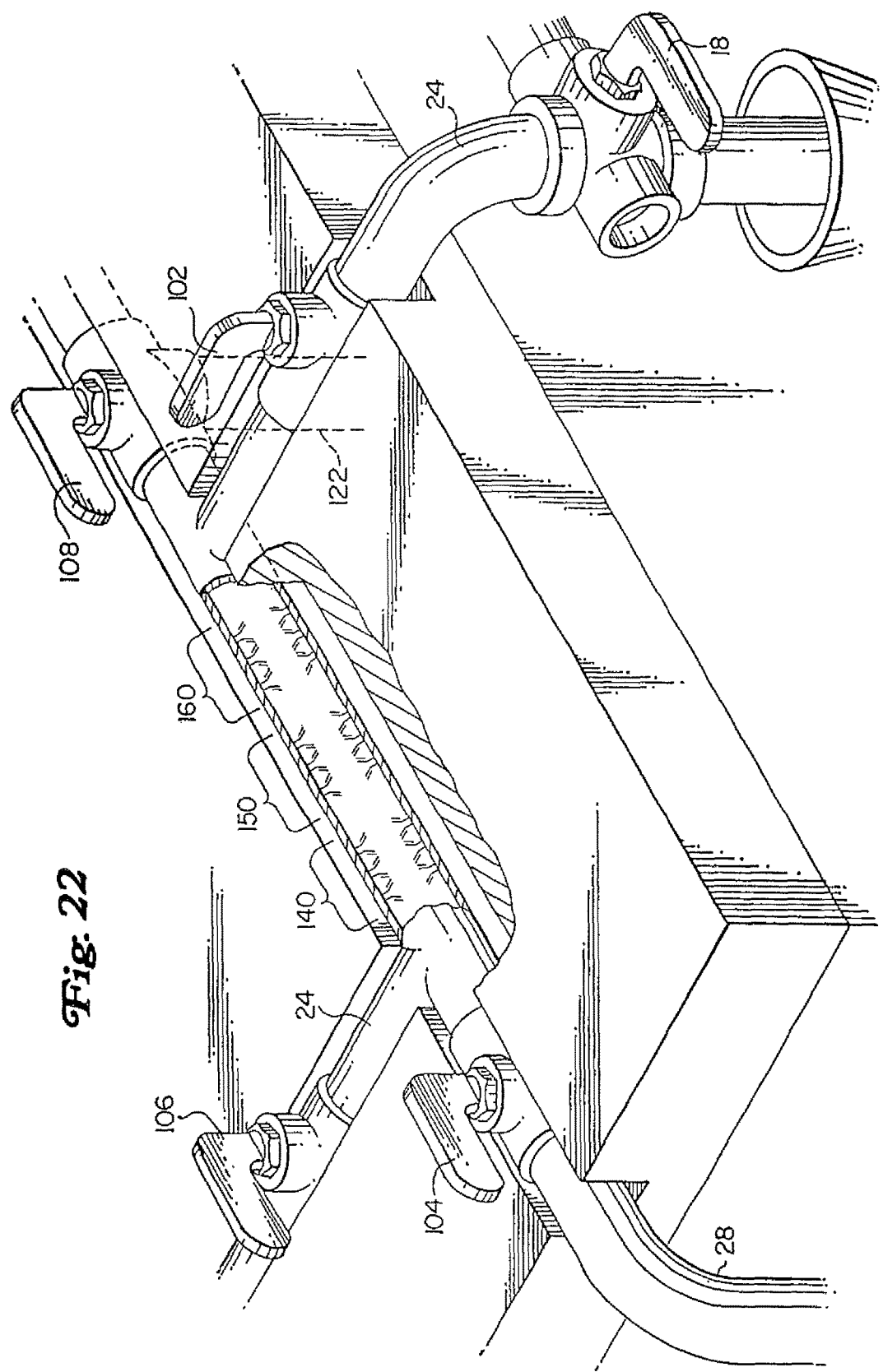

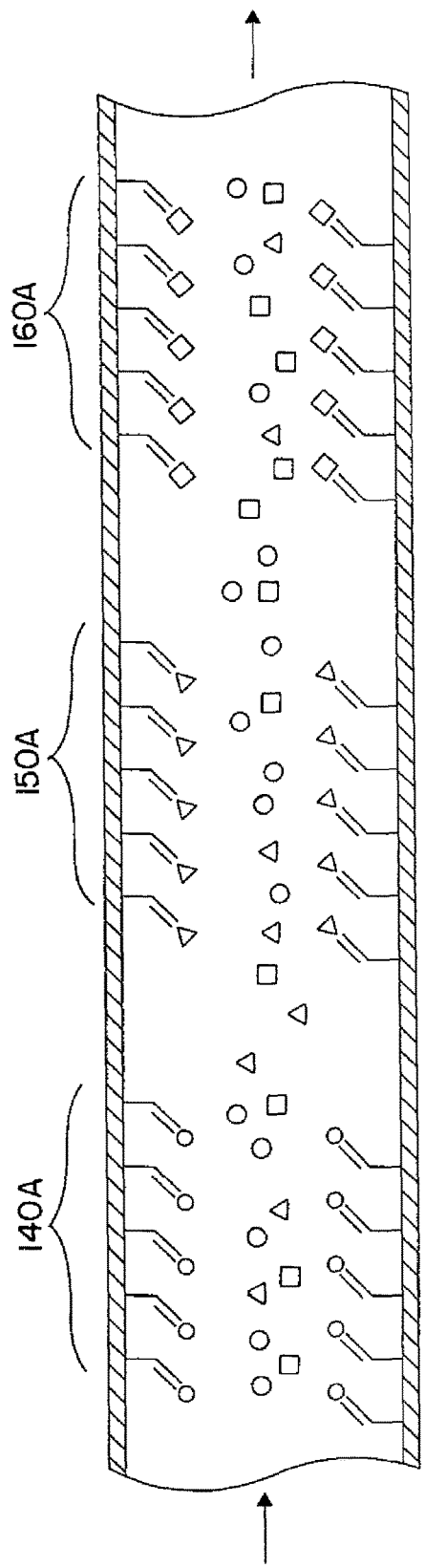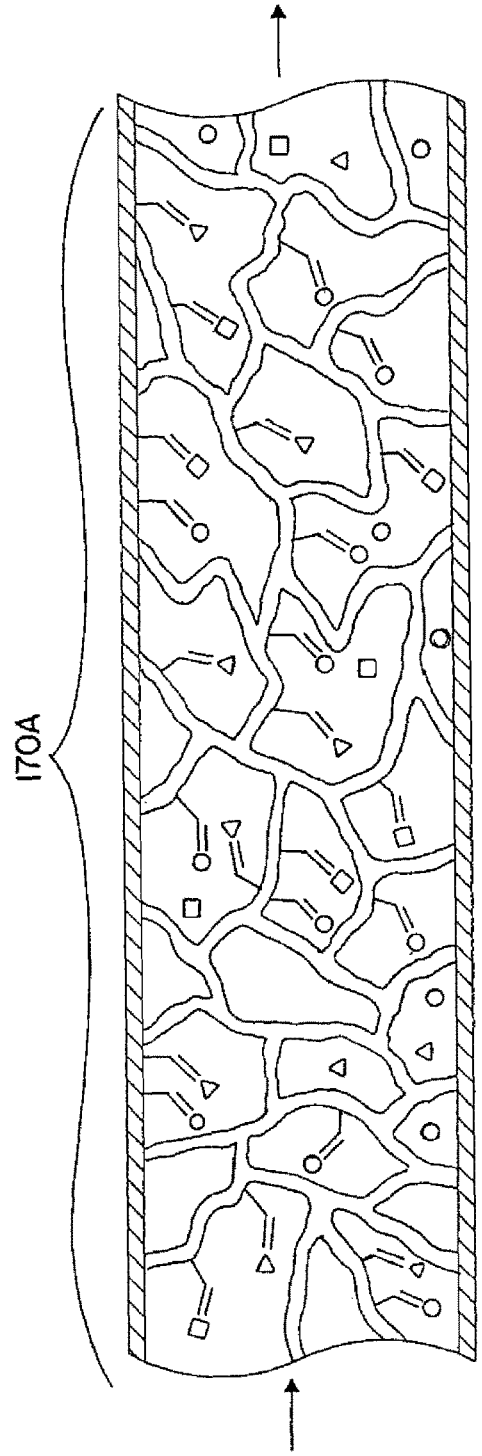

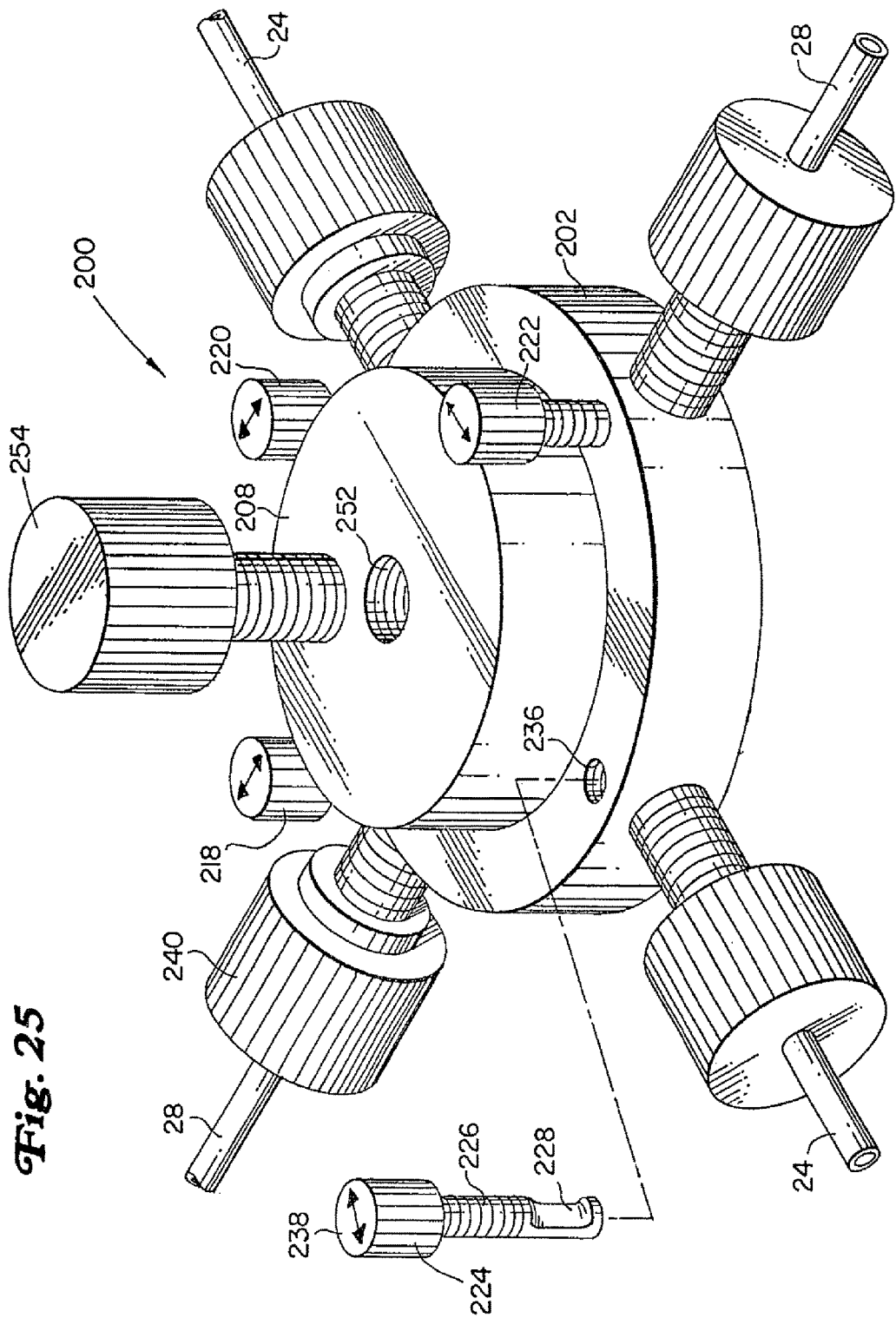

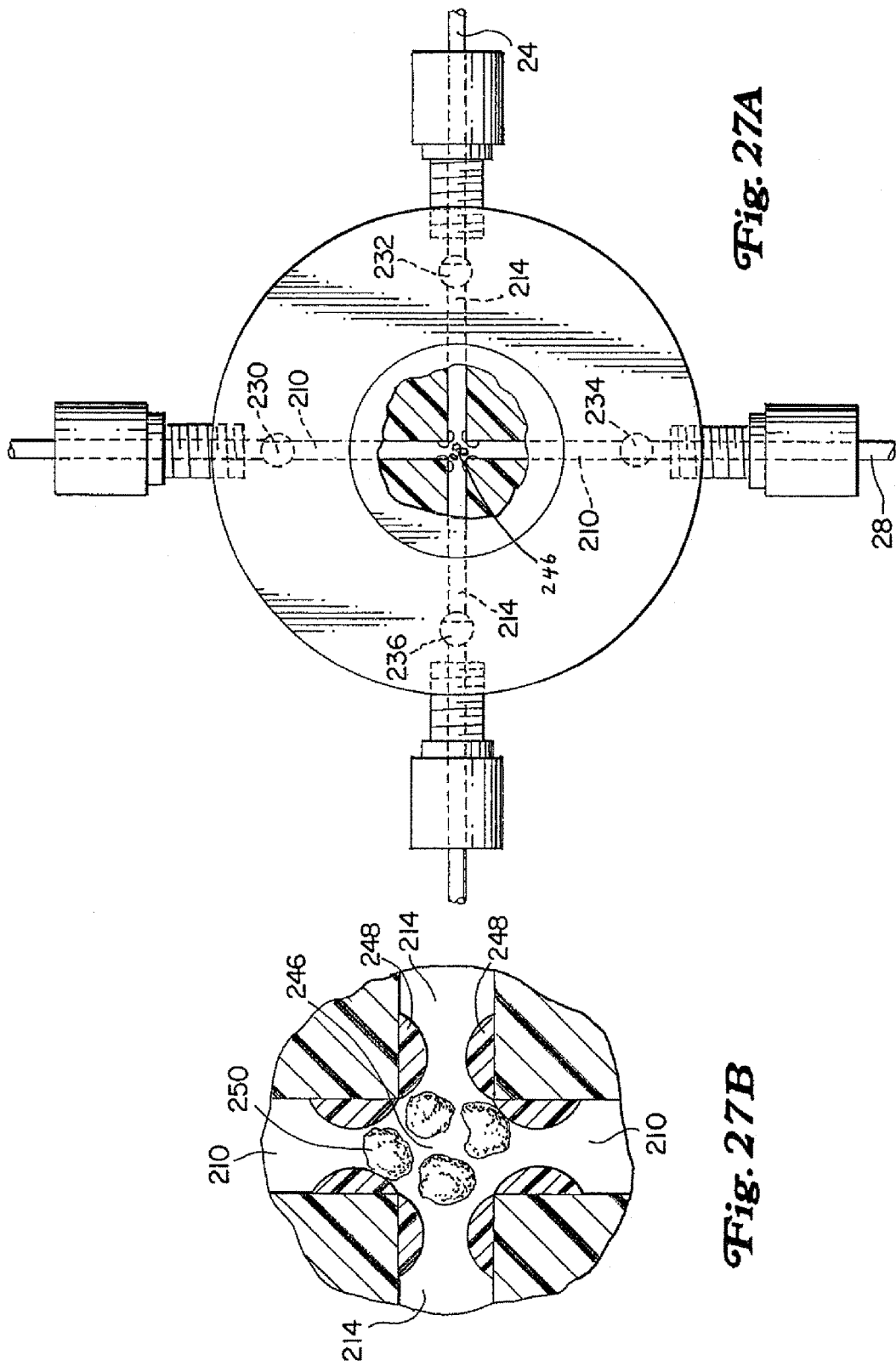

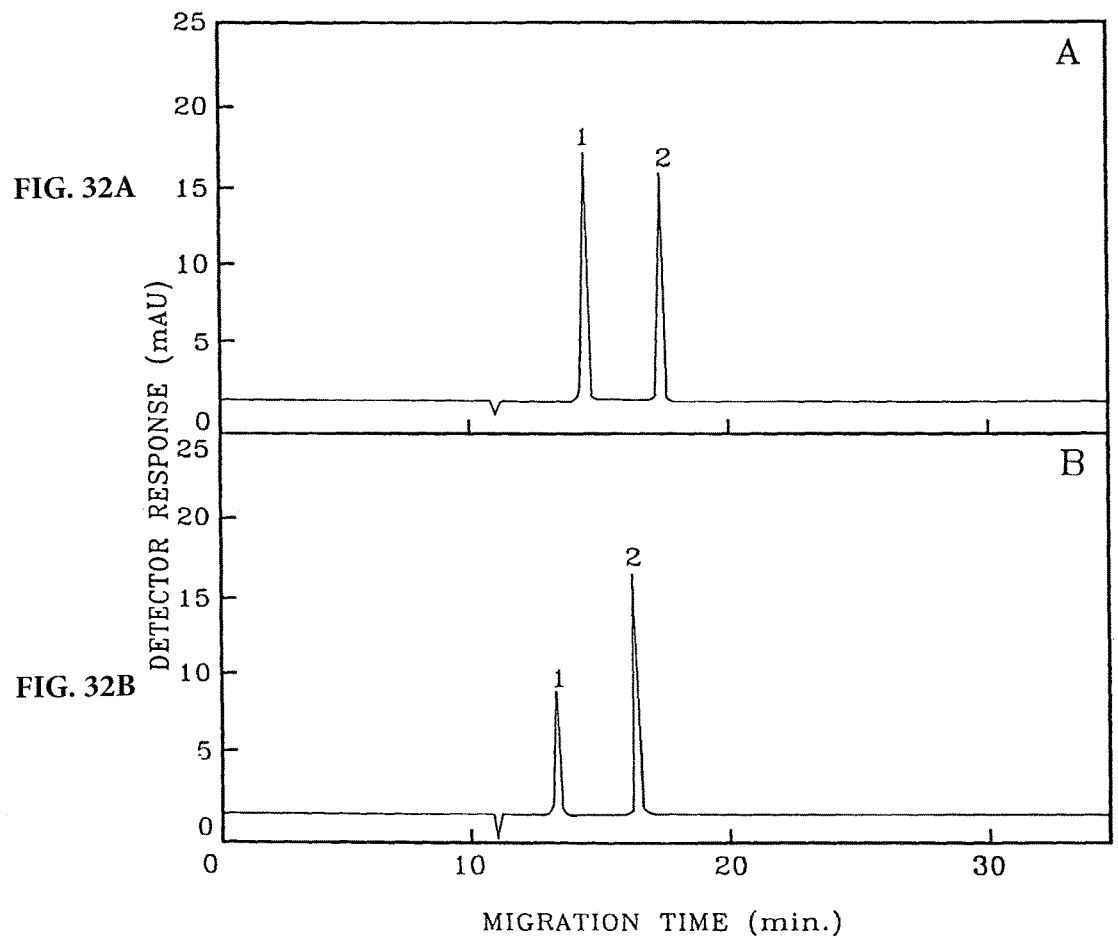

DISEASE DETECTION SYSTEM AND METHOD

RELATED APPLICATION

This application is a continuation-in-part of U.S. Patent Application entitled MULTI-DIMENSIONAL ELECTROPHORESIS APPARATUS, filed on Jun. 17, 2002, which is a continuation of U.S. Pat. No. 6,406,604 B1, filed on Nov. 8, 1999, which issued on Jun. 18, 2002, and claims priority to provisional application No. 60/518,186 filed on Nov. 7, 2003.

BACKGROUND OF THE INVENTION

1. Field of the Invention

The present invention relates generally to the analysis of chemical and biological materials and, more particularly, to an improved electrophoresis apparatus which simultaneously performs multiple analyses on a plurality of analytes.

2. General Background and State of the Art

Electrophoresis is a known technique for separating and characterizing constituent and/or biological molecules, or analytes, present in simple and complex matrices undergoing analysis. Candidate sample compounds include drugs, proteins, nucleic acids, peptides, metabolites, biopolymers and other substances which exist in simple and complex forms.

Conventional systems are based on interchangeable cartridges which house a thin capillary tube equipped with an optical viewing window that cooperates with a detector. Sample solutions and other necessary fluids are placed in vials (cups) positioned beneath inlet and outlet ends of the capillary tube by means of a rotatable table.

When high voltage is applied to a capillary filled with an appropriate solution and/or matrix, molecular components migrate through the tube at different rates and physically separate them. The direction of migration is biased toward an electrode with a charge opposite to that of the molecules under investigation. As the molecules pass the viewing window, they are monitored by a UV and/or other detector which transmits an absorbance and/or appropriate signal to a recorder. The absorbance and/or appropriate values are plotted as peaks which supply qualitative and quantitative analytical information in the form of electropherograms.

Electrophoresis separation relies on the different migration of charged particles in an electric field. Migration speed is primarily influenced by the charge on a particle which, in turn, is determined by the pH of the buffer medium. Electric field strength, molecular size and shape of the analyte, temperature of the system, and other parameters also influence migration behavior.

Electrophoresis is a family of related techniques that perform high efficiency separations of large and small molecules. As one embodiment of this science, capillary electrophoresis is effective for obtaining rapid and highly efficient separations in excess of one-hundred-thousand plates/meter. Because it is a non-destructive technique, capillary electrophoresis preserves scarce physical samples and reduces consumption of reagents. A fused silica (quartz) capillary, with an inner bore diameter ranging from about 5 microns to about 200 microns and a length ranging from about 10 centimeters to about 100 centimeters, is filled with an electrically conductive fluid, or background electrolyte, which is most often a buffer. Since the column volume is only about 0.5 to about 30 microliters, the sample introduction volume is usually measured in nanoliters, picoliters and femtoliters (ideally 2% of the total volume of the column). As consequence, the mass sensitivity of the technique is quite high.

Improved instrumentation and buffer-specific chemistries now yield accurate peak migrations and precise area counts for separated analytes. But, capillary electrophoresis is still limited by concentration sensitivity.

To overcome this deficiency, a series of solid-phase microextraction devices have been developed for selective and non-selective molecular consolidation. These devices, which are used on-line with a capillary tube, are commonly known as analyte concentrators containing affinity probes to bind target compounds. Typical embodiments are described in U.S. Pat. No. 5,202,010 which is incorporated by reference in this disclosure. Other relevant teachings are provided by U.S. Pat. No. 5,741,639 which discloses the use of molecular recognition elements; and U.S. Pat. No. 5,800,692 which discloses the use of a pre-separation membrane for concentrating a sample.

Even with the advent of analyte concentrators, there is still a need to improve the sensitivity levels for the samples that exist in sub-nanomolar quantities. This deficit is particularly acute in the clinical environment where early detection of a single molecule may be essential for the identification of a life-threatening disease.

Known capillary electrophoresis instruments are also limited by low-throughput, i.e., the number of samples that can be analyzed in a specified period of time. U.S. Pat. No. 5,045,172, which is incorporated by reference, describes an automated, capillary-based system with increased analytical speed. The '172 patent represents a significant improvement over the prior art. But, throughput is still relatively low because the instrument uses only one capillary which performs single sample analyses in approximately 30 minutes.

U.S. Pat. No. 5,413,686 recognizes the need for a multifunctional analyzer using an array of capillary tubes. Like other disclosures of similar import, the 86 patent focuses on samples having relatively high concentrations. There is no appreciation of the loadability and sensitivity necessary for analyzing diluted samples, or samples present at low concentrations in a variety of liquids or fluids.

Based on these deficiencies, there exists an art-recognized need for an electrophoresis instrument having higher loadability, better detectability of constituent analytes, faster throughput and multi-functional capability for analyzing a plurality of components in a single sample and/or a plurality of samples with high and low concentrations of components using a variety of chromophores, detectors and/or pre-concentration devices.

OBJECTS OF THE INVENTION

Accordingly, it is a general object of the present invention to provide an improved electrophoresis apparatus having at least one transport capillary, at least one separation capillary and an analyte concentrator positioned there between.

It is another object of the present invention to provide an electrophoresis apparatus having greater operating efficiency, detectability and throughput.

An additional object of the present invention is to provide a user-friendly, sample preparation step which is designed to eliminate unwanted analytes that occupy binding sites and contaminate the inner walls of capillaries or channels.

A further object of the present invention is to provide an electrophoresis apparatus that can analyze multiple samples having a single constituent, or multiple constituents of a single sample, or multiple constituents of multiple samples.

It is a further object of the present invention to provide an electrophoresis apparatus which uses more than one analyte concentrator to sequentially bind more than one analyte in a single complex matrix, or in multiple matrices of simple or complex configuration.

It is yet another object of the present invention to provide an electrophoresis apparatus having enhanced loadability and sensitivity which is capable of analyzing samples present in a wide range of concentrations, including those found at low concentrations in diluted liquids or fluids with simple or complex matrices.

It is a further object of the present invention to provide an electrophoresis apparatus that delivers high-throughput for screening and analyzing a wide variety of samples in multiple application areas, utilizing a single or multiple dimension separation principle or mode.

Another object of the present invention is to provide an electrophoresis apparatus which uses more than one separation method to sequentially permit binding to, and elution from, an analyte concentrator to effect the separation of one or more analytes.

It is another object of the present invention to provide an automated, miniaturized desk-top electrophoresis apparatus for bioanalysis and other applications.

Additional objects of the present invention will be apparent to those skilled in the relevant art.

SUMMARY OF THE INVENTION

In one aspect of the invention, a sample including a number of analytes of interest is passed through a relatively large-bore transport capillary orthogonal to a plurality of smaller-bore separation capillaries. An analyte concentrator is positioned at each intersection of the transport capillary and separation capillaries.

After the sample has been passed through each of the analyte concentrators, and after the analytes of importance are captured by each concentrator matrix, a selected buffer is applied to each analyte concentrator to free the system of salts and other non-relevant components. For example, a typical buffered solution is sodium tetraborate having a pH in the range of 7.0 to 9.0. The bound analytes are then eluted from each concentrator matrix in a sequentially time-controlled fashion using an aliquot or plug of an optimal eluting solution. The process continues until each of the analytes has been removed from the concentrator matrices and passed through the detector by high resolution electrophoresis migration. To increase the sensitivity of the analytes, an additional analyte concentrator containing a chromophoric reagent may be placed in one or more of the separation capillaries to react with the analyte present in that capillary. Alternatively, the eluting solution may contain a chromophoric reagent allowing decoupling and derivatization to occur simultaneously. The derivatized analytes can then be isolated in the separation capillary.

To separate and analyze multiple samples with the electrophoresis apparatus of the invention, individual separation capillaries are provided, each of which contains an analyte concentrator that enriches the analytes present in dilute solutions of low concentration or enriches the analytes present at low concentrations in solutions of simple or complex matrices containing constituent components at a wide range of concentrations. Multiple elutions are carried out in a manner similar to that performed when analyzing a single sample. Effective results can also be achieved using solutions that contain an appropriate eluting chemical and a chromophoric reagent to simultaneously elute the targeted analyte and enhance sensitivity. As with a single-sample analyzer, an extra analyte concentrator may be placed in one or more of the separation capillaries to allow on-line derivatization of analytes, prior and/or after separation conditions, to achieve even further enhancement of concentration sensitivity. In addition, an extra analyte concentrator may be placed in one or more of the separation capillaries to permit chemical and/or biochemical reactions, such as the on-line cleavage of proteins to generate peptides.

An analyte concentrator may also be used to quantify enzymatic products generated by the action of one or more pharmacological agents during a specific enzyme reaction. Furthermore, the use of an analyte concentrator coupled to a different mode of electrophoresis can be used to differentiate structurally related substances present in biological fluids or tissue specimens. For example, the identification and characterization of natural proteins from artificially-made proteins or other chemicals in serum.

All reactions described above can be performed in an apparatus containing a format that includes either capillaries or channels. In addition, the migration of analytes can be accomplished by an electrical or mechanical pump.

BRIEF DESCRIPTION OF THE DRAWINGS

FIG. 11A illustrates a cross-sectional view of the analyte concentrator of FIG. 10.

FIG. 11B illustrates a cross-sectional view of the analyte concentrator where the transport capillary is staggered to form a analyte concentrator that is elongated;

FIG. 22 illustrates a separation capillary having more than one type of antibodies within its interior wall between two valves;

FIG. 24A illustrates an enlarge view of multiple Fab' fragments along the interior surface of a separation capillary;

FIG. 24B illustrates polymeric microstructures with Fab' fragments having affinity for a particular analyte within the concentrator area without the need for fits;

FIG. 25 is a perspective view of a microextraction device having four tubing-connecting ports adapted to couple to transport and separation capillaries;

FIG. 27A illustrates the intersection area of FIG. 26;

FIG. 27B is an enlarge view of the intersection area of FIG. 27A;

FIG. 32A is a chart illustrating an electropherogram of ibuprofen (1) and naproxen (2), extracted by immunoaffinity bead technology from an aliquot of a diluted urine specimen;

FIG. 32B is a chart illustrating an electropherogram of angiotensin II (1) and neurotensin (2) extracted by immunoaffinity bead technology from a second aliquot of the same diluted urine specimen used in FIG. 32A;

DETAILED DESCRIPTION OF THE INVENTION

Figure 1:
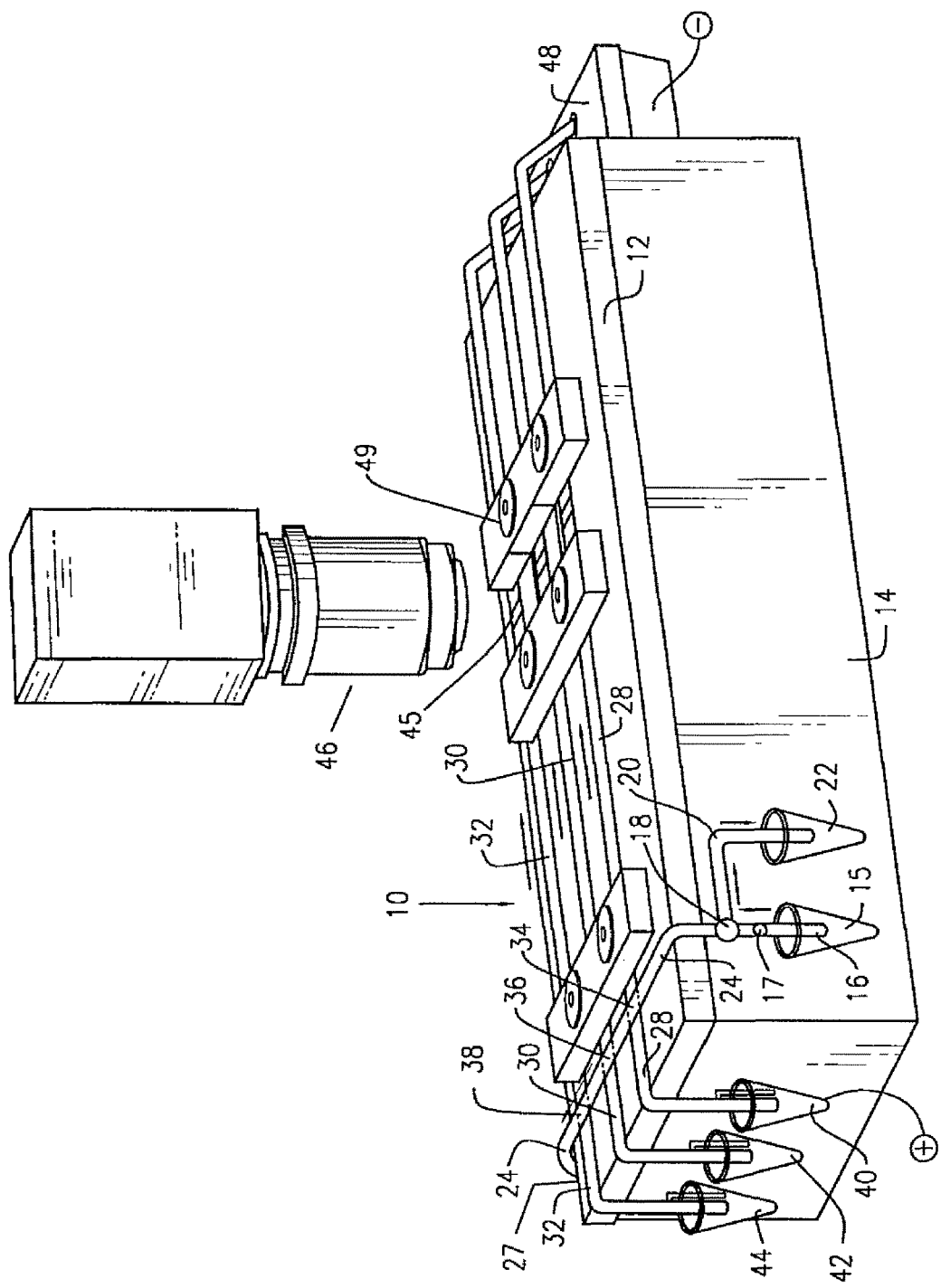
FIG. 1 is a perspective view of the electrophoresis apparatus of the present invention.

FIG. 1 illustrates electrophoresis apparatus 10 of the present invention. In its elementary mode (e.g., FIG. 8), apparatus 10 performs single sample studies on chemical or biological matrices having constituents or analytes of interest. But, according to the operating principles shown and described, apparatus 10 can perform multiple analyses by detecting and measuring the presence of a plurality of analytes (for example, three). Suitable and representative analytes may include narcotics, glucose, cholesterol or pharmaceutical drugs that may be present in urine or whole blood, as well as small and large molecular weigh substances having simple and complex structures.

As shown in FIG. 1, apparatus 10 includes platform 12 having side wall 14. Sample cup 15 is mounted laterally on side wall 14. A large-bore (150-300 mm in length×500-2000 µm I.D.), nonselective introduction capillary 16 and large-volume (1-3 ml) analyte concentrator 17 connect sample cup 15 to a first input of valve 18 which is coupled, by capillary 20, to waste container 22 positioned on side wall 14 adjacent to sample cup 15. In a typical configuration, analyte concentrator 17 comprises a matrix-like assembly of the type shown in U.S. Pat. No. 5,202,010. The collective mass of the matrix is provided by large quantities of microstructures such as beads, platelets, chips, fibers, filament of the like. Individual substrates can be made from glass, plastic or other polymeric material, ceramic, or metallic compositions, and mixtures thereof. Coated or otherwise deposited onto the microstructures are immobilized analyte-specific antibodies or other affinity chemistries which are suitable for characterizing and separating particular analytes of interest. Representative antibodies include those which act against peptide hormones such as insulin, human growth hormone and erythropoietin. These antibodies are readily available from commercial vendors such as Sigma-Aldrich Co., St. Louis, Miss., and Peninsula Laboratories, Belmont, Calif.

The present invention contemplates a user-friendly, sample preparation step which is designed to eliminate unwanted analytes that occupy binding sites and contaminate the inner walls of capillaries or channels. This procedure will now be described with specific reference to apparatus 10 of FIG. 2.

A first output of valve 18 is placed in the closed position and a quantity of solution from sample cup 15 is introduced into analyte concentrator 17. Depending on its pre-selected matrix, analyte concentrator 17 traps, in a non-specific manner, many (up to 100 or more) different analytes, including the analytes under investigation. Sample cup 15 is then replaced by a buffer container (not shown). This replacement step may be accomplished by a rotatable table mechanism of the type described in U.S. Pat. No. 5,045,172. Thereafter, a quantity of buffer is injected through analyte concentrator 17 to remove excess amounts of sample and unwanted sample components. Because valve 18 remains closed during this operation, excess and unwanted samples are passed into waste container 22.

Figure 2:
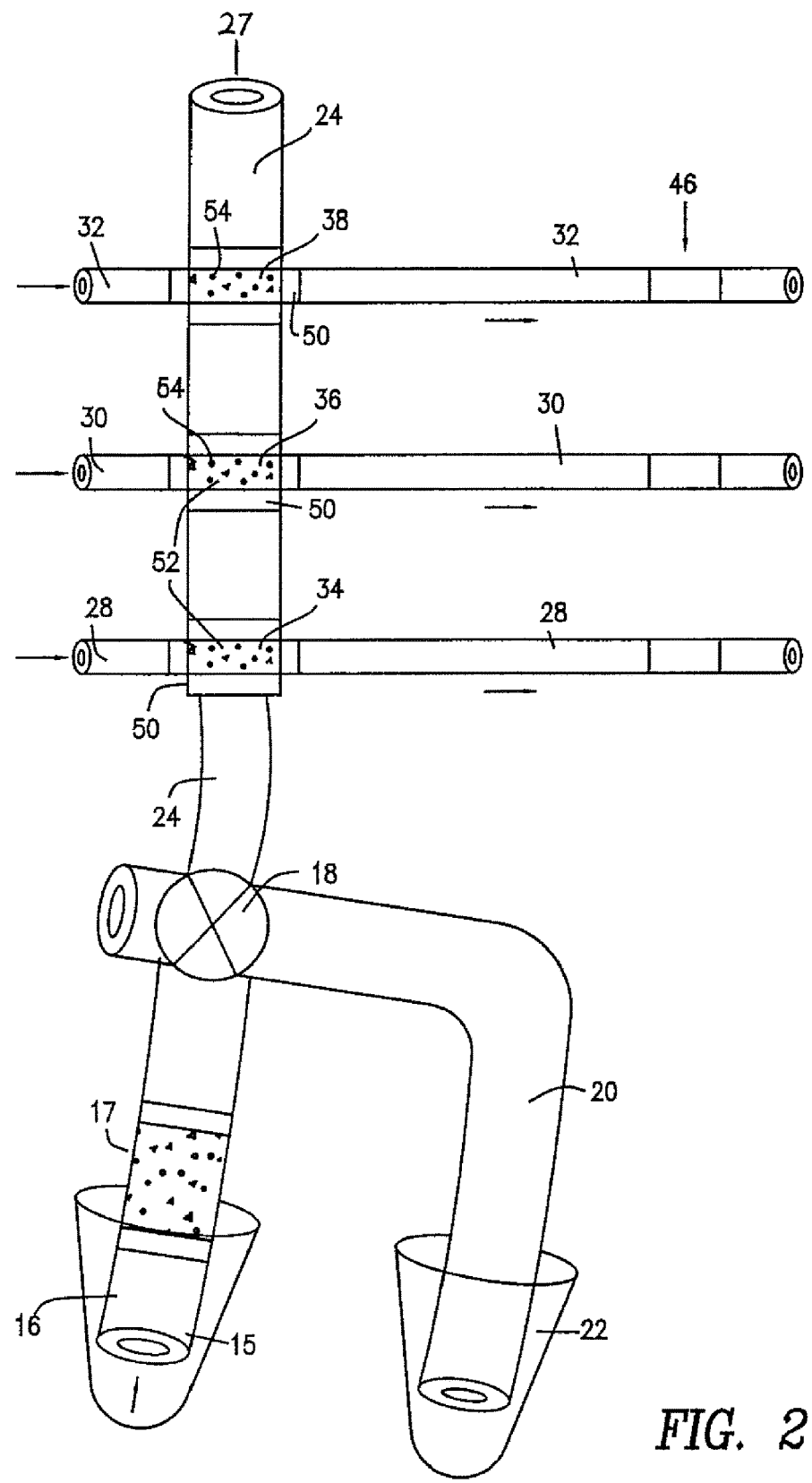
FIG. 2 is an enlarged, elevated view of a plurality of analyte concentrators stationed at the respective intersections of a large bore transport capillary and an equal plurality of small bore separation capillaries.

The remainder of apparatus 10 can now be considered. A second output of valve 18 communicates with transport capillary 24 which, as shown by FIG. 2, intersects a plurality, here shown as three, of narrow-bore (20-75 µm) separation capillaries 28, 30 and 32. Analyte concentrators 34, 36 and 38 are sequentially stationed at the intersections of transport capillary 24 and separation capillaries 28, 30 and 32 to trap or bind different analytes of interest.

Figure 3:
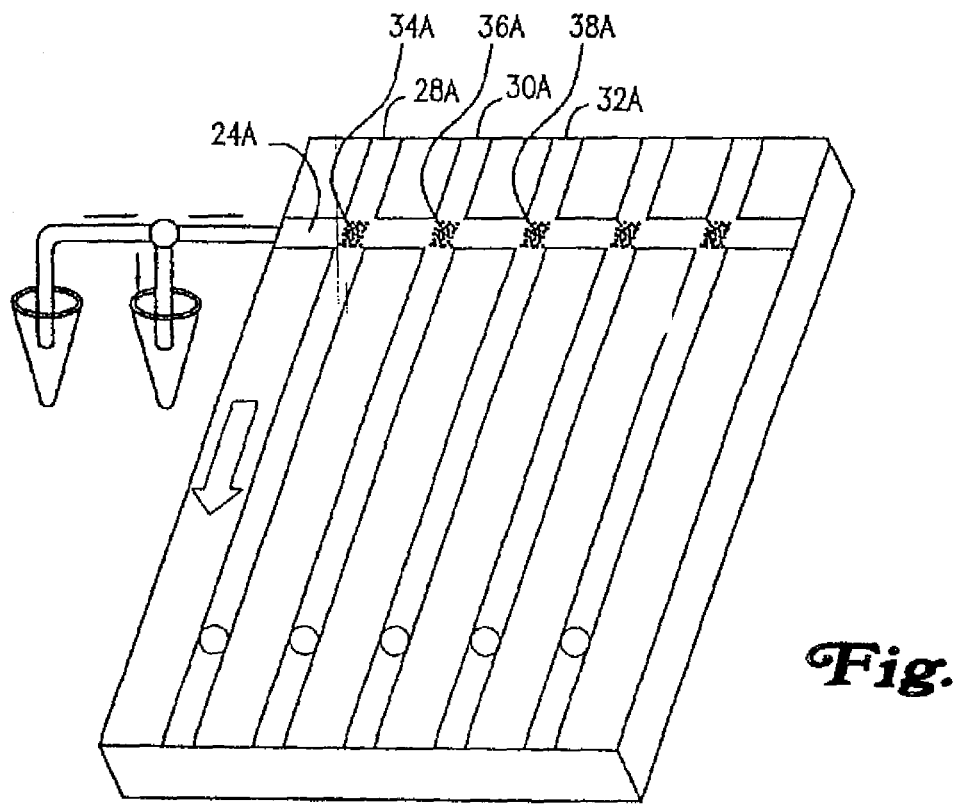
FIG. 3 is an elevated view of a second embodiment of the present invention, showing a plurality of analytes concentrators stationed at the respective intersections of an alternative transport channel and an equal plurality of separation channels.
Figure 3A:
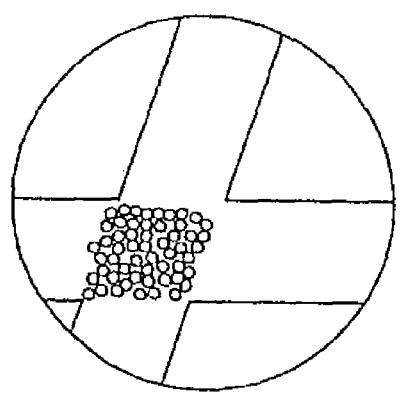
FIG. 3A is an enlarged view of the described intersection containing the analyte concentrator microstructure.

A first end (the left as viewed in FIG. 1) of separation capillary 28 is initially placed in buffer solution cup 40. In like manner, a first end of separation capillary 30 is placed in buffer solution cup 42; and a first end of separation capillary 32 is placed in buffer solution cup 44. A major portion of separation capillaries 28, 30 and 32 extend in parallel over the upper surface of platform 12 through detection zone 45 where the analytes respectively present in each of the separation capillaries are identified by an otherwise conventional detector 46. Separation capillaries 28, 30 and 32, which terminate at ground connection 48, may be secured to the upper surface of platform 12 by holder 49. Platform 12 can also take the form of an interchangeable cartridge with pre-positioned capillaries and analyte concentrators properly secured and aligned with respect to the optical system. In yet another embodiment, best shown in FIG. 3, transport channel 24A and separation channels 28A, 30A and 32A, having uniform and concave shapes, can be engraved, etched or otherwise formed into a glass or plastic microchip using known lithography or other manufacturing techniques. Analyte concentrators 34A, 36A and 38A are disposed at the respective intersections of transport channel 24A and separation channels 28A, 30A and 32A as previously described.

When the sample preparation step is complete, valve 18 is opened to the main system and a buffer (e.g., sodium tetraborate) is passed through introduction capillary 16 and analyte concentrator 17. At this time, the analytes of interest are released from analyte concentrator 17 using an eluting solution, along with other analyte constituents present in the sample. The analytes of interest and all the other analytes captured and released by concentrator 17 are passed through transport capillary 24 to analyte concentrators 34, 36 and 38 which, as described below with reference to FIG. 3, contain a large quantity of microstructures that are capable of binding different analytes of interest; that is, each of the analyte concentrators 34, 36 and 38 select and isolate a different one of the analytes under investigation. Excess amounts of sample then pass through the other end of transport capillary 24 to waste container 27. Transport capillary 24 is subsequently washed with running buffer until unwanted substances are removed.

Separation capillaries 28, 30 and 32 are filled hydrodynamically (pressure or vacuum) with an appropriate electrophoresis separation buffer which occupies the entire volume of the capillary or channel. Immobilized analytes on a solid support are stable for long period of time. As a result, large numbers of analytes can be consequently separated over time, thereby providing high throughput for the apparatus of the present invention. Separation capillary 28 is first activated by introducing a plug of an appropriate eluting buffer from cup 40 by hydrodynamic (pressure or vacuum) or electrokinetic methods to desorb or elute analytes bound to analyte concentrator 34. The eluting buffer is immediately followed by a freshly prepared electrophoresis separation buffer present in replacement cup 40. Then, the power supply connected to cup 40 is activated to begin the process of analyte separation.

As shown in Table 1, with insulin taken as representative, a typical analysis involves the targeted analyte of interest, its corresponding antibody, an appropriate buffer and eluting solution.

TABLE 1

| Antigen | Antibody | Separation Buffer[+] | Eluting Solution[*] |
|---------|----------|----------------------|---------------------|
| Insulin | Anti-insulin antibody | Sodium tetraborate (pH 8.5) | Magnesium Chloride and Ethylene Glycol |

[+]Concentrations of electrophoresis separation buffer may range from 50 mM to 200 mM.
[*]Elution of other antigens or haptens may require a different eluting method. Effective eluting buffers include a 2M solution of Magnesium Chloride and a 25% solution of Ethylene Glycol.

When the initial separation is complete, the next cycle, using separation capillary 30 and analyte concentrator 36, is performed in a similar manner, i.e., the analyte is eluted from concentrator 36 and then separated by electrophoresis migration in separation capillary 30. During these operations, the power supply is connected to one analyte concentrator-separation capillary system at a time.

Separated analytes are then passed sequentially to detection zone 45 where each analyte is recognized and measured by detector 46 using, for example, known UV or fluorescence techniques. In one embodiment of the present invention, a single, bi-directional detector is indexed laterally above platform 12 to detect analytes of interest in separation capillaries 28, 30 and 32 or separation channels 28A, 30A and 32A. Other sub-assemblies could include a single, fixed detector and movable platform 12 which operates to position separation capillaries 28, 30 and 32 or separation channels 28A, 30A and 32A beneath the detector. Multiple detectors are movable platforms configured for X, Y and Z indexing are also contemplated.

Figure 4:
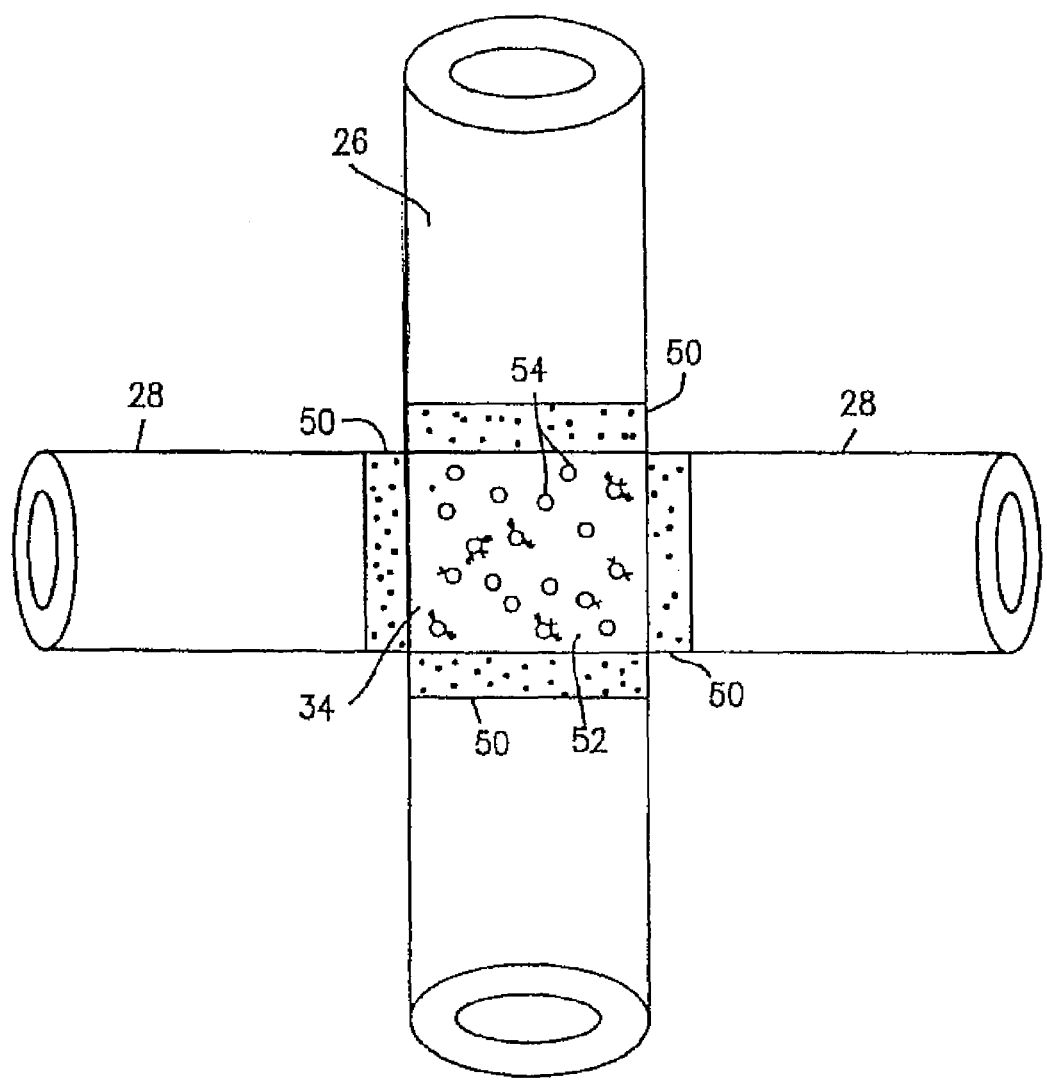
FIG. 4 is an enlarged, elevated view of an analyte concentrator stationed at the intersection of a transport capillary and a separation capillary.

FIG. 4 illustrates the location of analyte concentrator 34 stationed at the intersection of transport capillary 24 and separation capillary 28. As shown in FIG. 4, and in U.S. Pat. No. 5,202,010, porous end plates or frits 50, which permit fluid flow, are provided in transport capillary 24 and separation capillary 28 to act as barriers for holding microstructures 54 in analyte concentrator 34.

Figure 5:
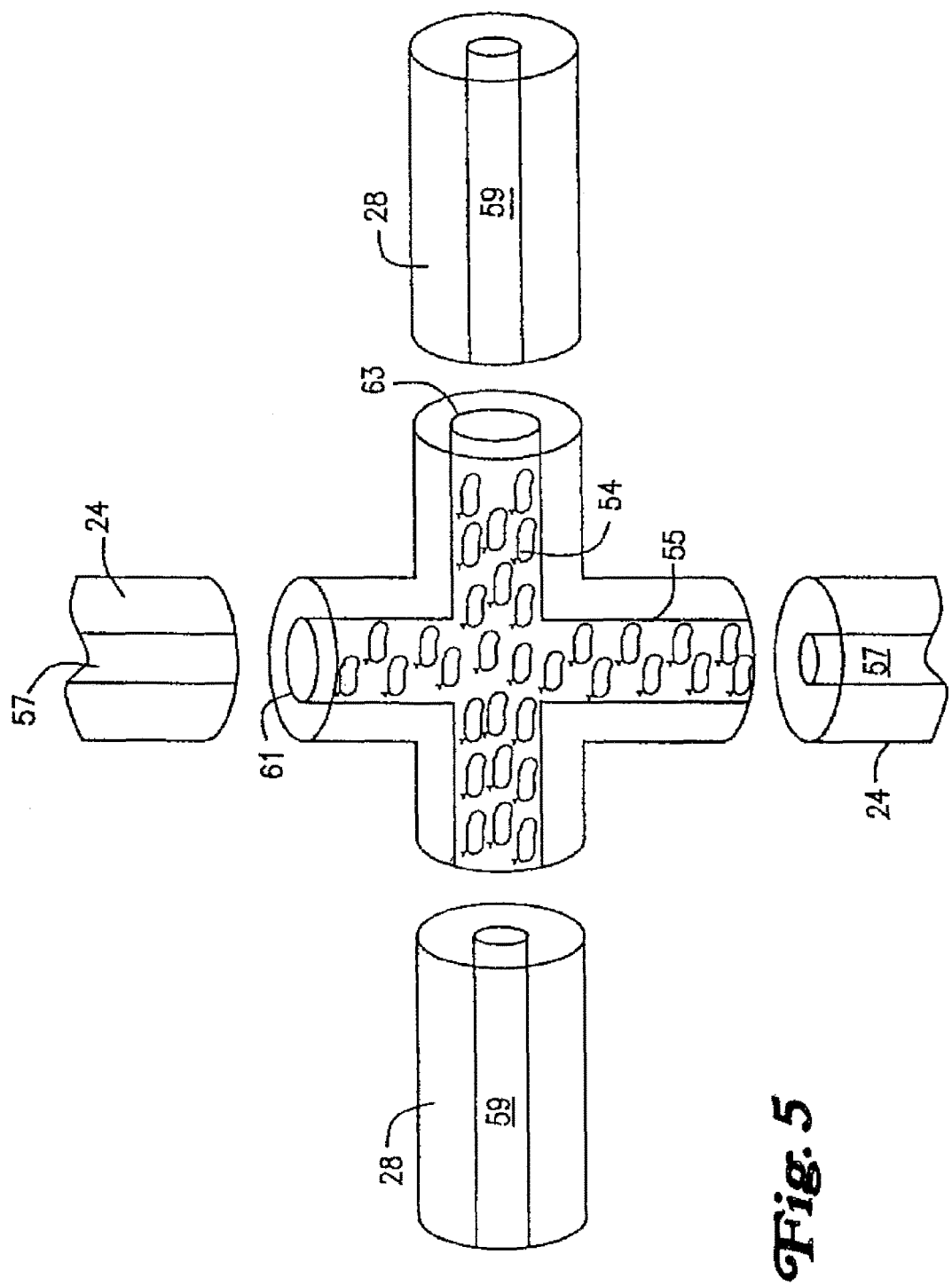
FIG. 5 is an elevated view of an analyte concentrator in the form of a cross-shaped capillary.

Alternatively, as shown in FIG. 5, analyte concentrator 55 can be fabricated by using two constricted areas with no frits at all. Analyte concentrator 55, in the form of a cross-shaped capillary, has inner diameter 61 and 63 pre-formed in relation to inner diameter 57 of transport capillary 24 and inner diameter 59 of separation capillary 28.

Analyte concentrator capillary 55 contains a plurality of previously described microstructures 54 which are larger than inner diameters 57 and 59. They are typically coated with non-specific chemistries such as C-18 or highly specific antibodies or antigens having an affinity for one of the analytes under investigation. Several other well-known chemistries can also be used.

In the embodiment illustrated by FIG. 5, microstructures 54 are retained or confined in the interior of analyte concentrator 55 by making inner diameter 57 of transport capillary 24 smaller than inner diameter 61 of analyte concentrator 55. In like manner, inner diameter 59 of separation capillary 28 is smaller than inner diameter 63 of analyte concentrator 55. For example, inner diameters 57 and 59 may be one-quarter to one-half the size of inner diameters 61 and 63.

To increase detection sensitivity for a particular analyte, a chromophore may be added to the eluting buffer to elute and tag the bound analyte for the purpose of enhancing the ultraviolet absorptivity, fluorescence, phosphorescence, chemiluminescence or bioluminescence of the analyte as it passes through detector 46.

Figure 6:
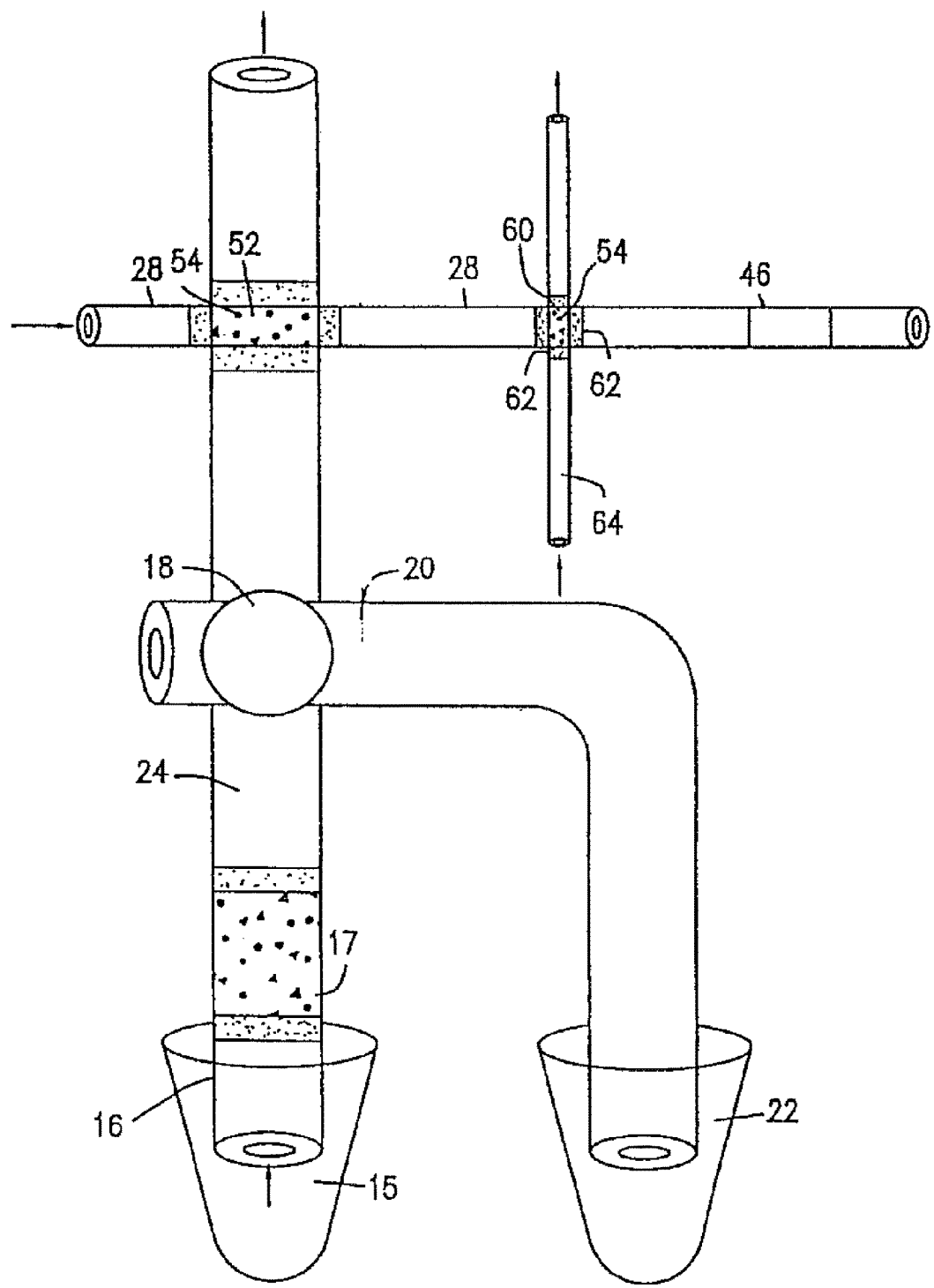
FIG. 6 is an elevated view of the electrophoresis apparatus of the present invention, showing an analyte concentrator disposed along the length of a separation capillary.

In an alternative technique to increase detection sensitivity, additional analyte concentrator 60 may be placed in one of separation capillaries 28, 30 and 32, as shown in FIG. 6. Analyte concentrator 60 has a plurality of microstructures 54 coated with a chromophoric agent or antibody that binds to a portion of a chromophoric agent which increases ultraviolet absorptivity, fluorescence or phosphorescence when bound to a minute quantity of a specific analyte. Frits 62 are located at the input and output of analyte concentrator 60, and narrow capillary 64, which interests with separation capillary 28, carries a buffer to periodically cleanse microstructure 54 in analyte concentrator 60 after each analysis.

An analyte tagged with a chromophoric agent is more readily identify by the apparatus of the present invention, thereby increasing the sensitivity of analyte detection by as much as 100 times or more. Many different chromophoric agents emit light when they bind a specific functional group to form a product molecule in an electronically excited state.

Figure 7:
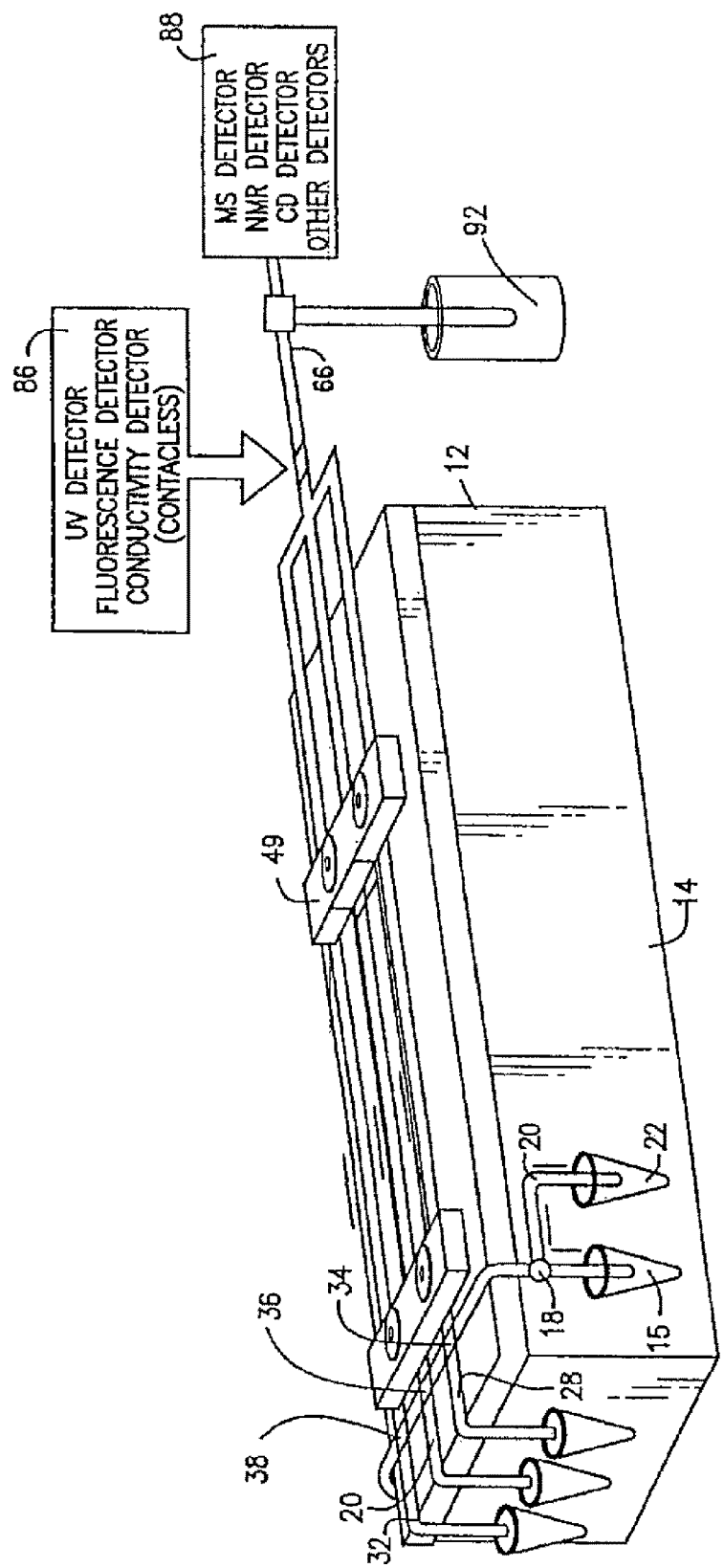
FIG. 7 is a perspective view of a third embodiment of the present invention, showing a plurality of separation capillaries connected to a single outlet capillary for sequential detection.

The alternative embodiment illustrated by FIG. 7 is similar to that shown in FIG. 1. But, the FIG. 7 embodiment is different because the output ends of separation capillaries 28, 30 and 32 are connected to each other at the interface with a single outlet capillary 66 which cooperates with on-column detector 86 that senses ultraviolet (UV) or fluorescent energy. The exit position of outlet capillary 66 may also be connected (as shown) to off-column detector 88 which comprises an electrochemical, mass spectrometry, circular dichroism detector or nuclear magnetic resonance detector.

The electrophoresis apparatus of FIG. 7 employs multiple separation capillaries or channels for sample concentration, but only one outlet capillary for sample detection. This coordinated separation by individual capillaries may be sequentially activated and controlled by well-known electronic circuitry. Like the FIG. 1 embodiment, preceding analytes are completely separated and detected before the next separation operation is activated.

Figure 8:
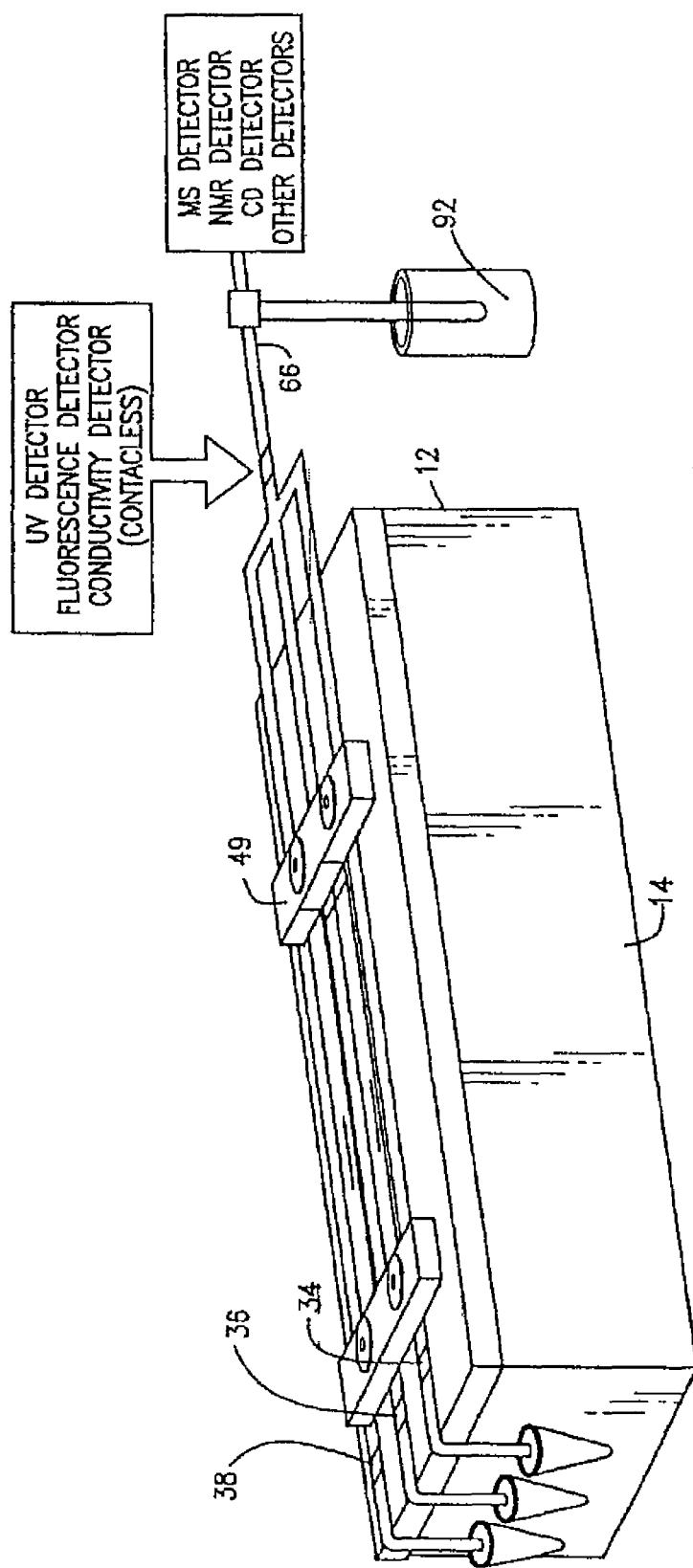
FIG. 8 is a perspective view of a fourth embodiment of the present invention, showing a plurality of separation capillaries adapted to analyze multiple samples according to the techniques described in the specification.

The electrophoresis apparatus of FIG. 8 is similar to that of FIG. 7, but it is adapted to work with multiple samples (here, e.g., three) having a simple or complex component. There is no introduction (transport) capillary 16 or sample cup 15 as provided by embodiments of FIG. 1 and FIG. 7. Separation capillaries 28, 30 and 32 are equipped with single analyte concentrators 34, 36 and 38, respectively. Individual samples are directly and sequentially delivered to separation capillaries 28, 30, 32, and the analytes of interest are captured using suitable chemistries as previously described. The capillaries may be washed with buffer until all salts and unwanted substances are removed. Like the FIG. 7 embodiment, separation capillaries 28, 30 and 32 are activated in series one after the other. When all the analytes are separated in a single capillary, the apparatus begins the next separation cycle in the next capillary. In each of the described embodiments, apparatus 10 provides greater efficiency and higher throughput when compared to prior art devices.

Improved instrumentation containing a series of solid-phase microextraction devices on-line in a multi-dimensional electrophoresis apparatus has been developed for selective and non-selective molecular consolidation and it is described in U.S. Pat. No. 6,406,604 B1, which is hereby incorporated by reference. These devices, known as analyte concentrators or analyte concentrators-microreactors containing affinity probes to bind target compounds, permit the capturing of analytes present in simple or complex mixtures for purification, desalting and enrichment purposes. Furthermore, it allows the performance of many chemical and/or biochemical reactions, such as the on-line enzymatic cleavage of proteins to generate peptides. This continuation-in-part describes further improvements of the described embodiment.

Figure 9:
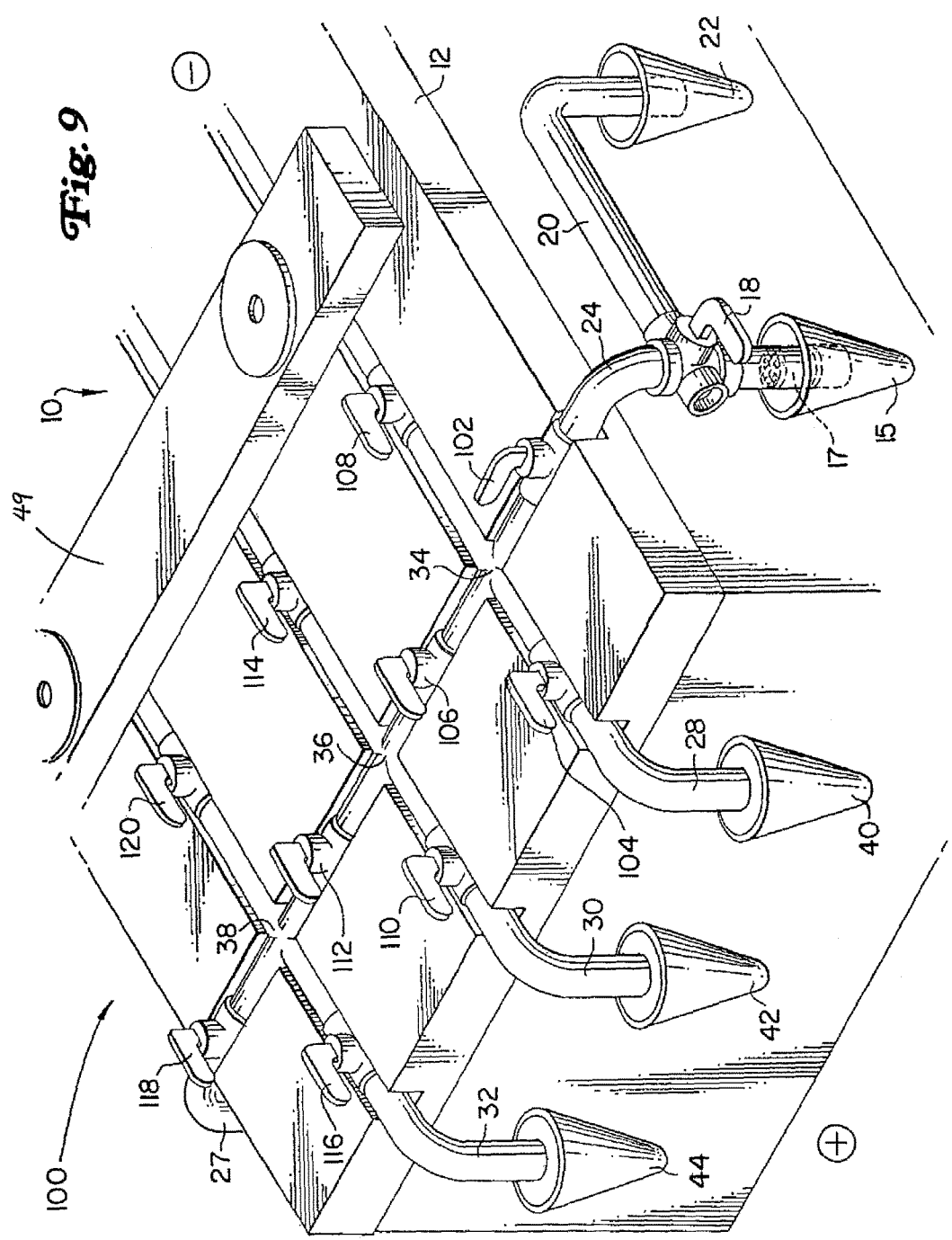
FIG. 9 is a perspective view of an electrophoresis apparatus having a valving system that directs the flow of fluid along a desired path through the transport capillary and separation capillaries.

FIG. 9 illustrates an electrophoresis apparatus 10 including a valving system 100 that directs the flow of fluid along a desired path through the transport capillary 24 and separation capillaries 28, 30, and 32. In this example, valves 102, 104, 106, and 108 may control the flow of buffer solution(s) around the concentrator 34; valves 106, 110, 112, and 114 may control the flow of buffer solution(s) around the concentrator 36; and valves 112, 116, 118, and 120 may control the flow of buffer solution(s) around the concentrator 38. With the valving system 100, the environment for each of the concentrator may be localized. Localizing a concentrator allows for independently controlling the microenvironment of that concentrator, such as controlling concentration of reagents, temperature, time of reactions, etc. The valving system 100 allows the loading of one or more appropriate background electrolyte solution, the introduction of the samples to be analyzed by the various modes of capillary electrophoresis, and the cleaning of the capillaries so that the capillaries may be reused.

The transport capillary 24 and the separation capillaries 28, 30, and 32, along with the valving system 100 may be incorporated into the platform 12 of the electrophoresis apparatus 10 in a variety of ways. For instance, holders 49 may be used to hold the capillaries in place relative to the platform 12. After certain number of usage, the condition of the capillaries or the valving system 100 may degrade so that they may need to be replaced. In such instances, the holders 49 may be removed from the platform 12 and a new system of capillaries and valving system may be installed into the platform. Alternatively, a new system of capillaries and valves may replace the existing capillaries to isolate different types of analytes from the sample solution in the cup 15. The concentrators 34, 36, and 38 in the replacement capillaries may each have different immobilized affinity ligands that are attracted to a different type of analyte than the ones they are replacing. This way, the electrophoresis apparatus 10 may be reused and adapted to isolate a variety of analytes.

The transport capillary 24 may be also adapted to perform isoelectric focusing (IEF) separation of a sample solution by maintaining the valves on the transport capillary opened and the valves on the separation capillaries closed. The intersection of the transport and separation capillaries may be emptied without frits and matrix-assembly in the concentrators. IEF is a method of determining the isoelectric point (pI) of a protein by carrying out electrophoresis in a capillary or gel containing a pH gradient. The pI is the pH at which a protein will not migrate in an electric field and is determined by the charged groups in the protein. Proteins can carry positive, negative or zero charge depending on their local pH, and for every protein there is a specific pH at which its net charge is zero; this is its pI. IEF utilizes different pI in proteins to separate the proteins based on their pI levels. When a protein is placed in a medium with a pH gradient and subjected to an electric field it will initially move towards the electrode with the opposite charge.

During migration through the pH gradient the protein will pick up or lose protons. As it migrates the net charge and the mobility will decrease and the protein will slow down. Eventually the protein will arrive at the point in the pH gradient which is equal to its pI. At such point, the protein will be uncharged and stop its migration. If the protein should happen to diffuse to a region outside its pI it will pick up a charge and hence move back to the position where it is neutral. In this way proteins are condensed, focused, or separated into certain bands according to their pI levels. This way, dual mode of separations may occur with the electrophoresis apparatus 10, IEF separation through the transport capillary and the separation of the desired analyte through the separation capillaries. In this case, one electrode may be provide in the cup 15 and the other electrode on the outlet end of the transport capillary to provide the electric field to focus and separate the proteins present in transport capillary 24. After isoelectric focusing separation is completed, the valves on the transport capillary may be closed and the valves on the separation capillaries may be opened. Further separation of the proteins may be accomplished by other modes of capillary electrophoresis in separation capillaries 28, 30, and 32.

Figure 10:
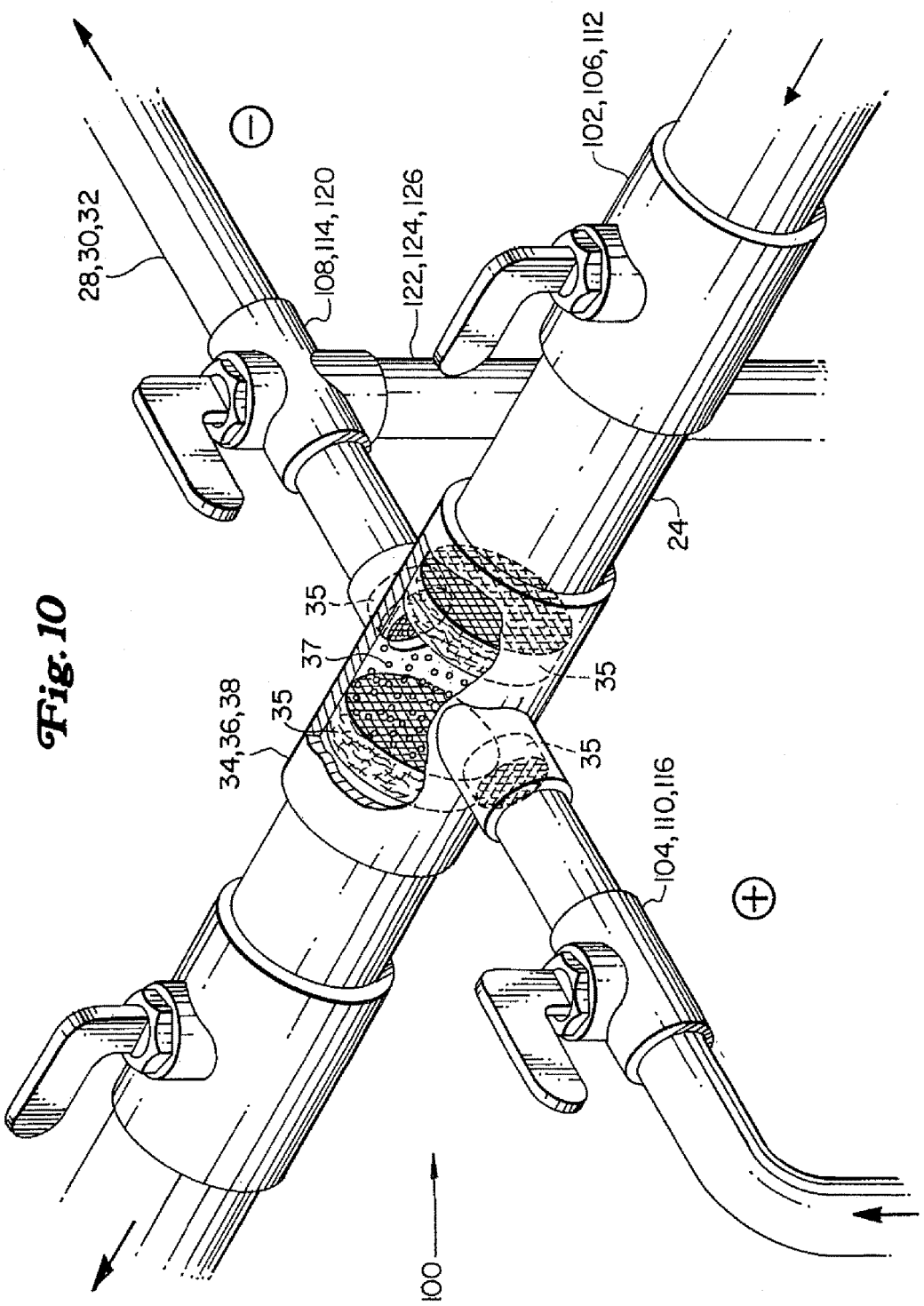
FIG. 10 is an enlarge view of an analyte concentrator capable of being localized by surrounding valves on the transport and separation capillaries.

FIG. 10 illustrates a perspective view of the valving system 100 for one of the analyte concentrators. Each concentrator may be surrounded by frits or porous end plates 35 provided along the path of the transport capillary 24 and the respective separation capillary to retain the matrix-like assembly 37 within the concentrator. The valves on the transport capillary and the separation capillary also surround each of the concentrators to control the flow of sample solution through the transport capillary 24 and through the respective separation capillary. The valves may be motor operated that is controlled remotely by a processor based on a predetermined set of instructions such as a software program. After the concentrators 34, 36, and 38 have been properly conditioned, the valves along the transport capillary may be opened and the valves along the separation capillaries 28, 30, and 32 may be closed to allow the concentrated sample solution from the concentrator 17 to pass through the concentrators 34, 36, and 38. This allows each of the matrix-like assembly in the concentrators 34, 36, and 38 to bind to the desired analyte from the concentrated sample solution. The remaining concentrated sample solution may be released to the waste container 27 on the other end of the transport capillary 24.

Once each of the desired analytes of interest are bound to the respective matrix-like assembly within the concentrator, the valves on the transport capillary may be closed and the valves on the separation capillaries 28, 30, and 32 may be opened. To separate the desired analyte(s) that are attached to each of the matrix-like assembly in the concentrators 34, 36, and 38, a separation solution may be passed through the separation capillaries 28, 30, and 32 so that each of the desired analyte may travel towards the detection area 45 after released from the concentrators 34, 36, and 38. More detail steps involved in the process of concentrating, isolating, and separating the desired analytes from the sample solution provided in the sample cup 15 are discussed later in the specification.

FIG. 10 illustrates a concentrator with porous end plates or frits 35, which permit fluid flow, in the transport capillary 24 and separation capillary 28 to act as semi-permeable barriers for holding matrix-like assembly 37 within the analyte concentrator. For the concentrator 34, the flits 35 may be formed along the transport capillary 24 and the separation capillary 28. The fit 35 and the matrix-like assembly 37 may be the type shown in U.S. Pat. Nos. 5,202,010 and 6,406,604, which are hereby incorporated by references. The matrix-like assembly may be provided in many forms. For instance, the collective mass of the matrix may be provided by large quantities of microstructures such as beads, platelets, chips, fibers, filaments, monolithic polymers, sol-gel, or the like. Individual substrates can be made from glass, plastic, ceramic, metallic, or any appropriate polymeric chemistry compositions, and mixtures thereof. The use of interconnected beaded and/or polymeric microstructures may not require the presence of frit structures to hold the matrix, because they form a net that it is linked by chemical bonding, and they are usually positioned in a rigid configuration. In most cases, these beaded or polymerized microstructures may sustain low-pressures. However, in certain cases that high-pressure may be needed, their network configuration can be deteriorated or destroyed. Covalently or non-covalently affinity ligands coated or immobilized onto the surface of the beaded microstructures or monolithic polymers, sol-gel, or directly onto the inner wall of the capillary, are immobilized analyte-specific antibodies or other affinity chemistries which are suitable for characterizing and separating particular analytes of interest. Representative antibodies include those which act against peptide hormones such as insulin, human growth hormone and a variety of antibodies directed against any substance of small molecular weight (classified as hapten) or any substance of larger molecular weight or biopolymer (classified as antigen). These antibodies are readily available from commercial vendors such as Sigma-Aldrich Co., St. Louis, Mo. and Peninsula Laboratories, Belmont, Calif., and many other companies worldwide. Alternatively, one skilled in the art may manufacture a desire monoclonal and/or polyclonal antibody by conventional methods or protocols described in the literature. Not all haptens are capable of elicit an antigenic response by itself, usually they need to be bound to an antigenic protein carrier to generate an antibody.

The matrix-like assembly may include affinity elements immobilized in various configurations and orientations in order to obtain a higher concentration of the desired analytes. For example, antibody fragments may be used instead of complete antibodies to obtain a higher concentration of the desire analytes. The larger diameter of the transport capillary 24 may require that the two frits in capillary 24 be larger than the frits in the separation capillaries 28, 30, and 32. Conversely, the matrix-like assembly may be configured to capture the desired analytes through the use of affinity ligands that are immobilized onto the surface of frit-free polymeric structures, as mentioned above. Alternatively, affinity ligands may be immobilized onto the surface of commercially available magnetic beads to be used as matrix material and substantially confined to a predetermined location within the capillary through magnetic attraction. Using magnetic attraction to hold the matrix in a predetermined location along the capillary may eliminate the need for frits. The absence of the frits may allow the flow of sample through the capillary to move faster, while retaining a surface to attach the affinity elements.

The concentrator 17 may include immobilized ligands comprised of a single nonselective or a mixed-mode nonselective type of chemistries such as reversed-phase C18 and ion-exchanger matrices or resins, etc. The mixed mode may be allowed to capture and enrich a wide range of analytes based primarily on their physico-chemical properties, including the charge, size, shape, hydrophobicity, etc. The reversed-phase C18 chromatography adsorption resins, anion exchange matrices or resins, cation exchange, immobilized metal affinity capture, or mixed-modes resins may be placed in the concentrator 17 in a sequential order, one type first and then the other, or as a mixed matrix. The analytes can also be eluted in a sequential order according to their physico-chemical properties.

The concentrator 17 may also be composed of immobilized ligands including a selective type of chemistry such as antibody, lectin, enzyme, aptamer, dye affinity chromatography, etc. For example, a particular lectin can recognize a specific sugar in a sugar-containing element, such as a glycoprotein, and retain the entire glycoprotein molecule. The selective type of chemistry may bind a single analyte or a very close structurally related analyte. In the case of a complete monomeric antibody, it may have two antigen-binding sites; in the case of a Fab fragment, it may have a single antigen-binding site. However, in the case of other selective affinity ligands, it may have more than one site to bind the target analyte, an enzyme may have an active site to bind the corresponding substrate, and an inhibitor-activator may bind to the same active site or to a different site (e.g., allosteric site). The concentrators 34, 36 and 38 may also include immobilized affinity ligands other than antibody fragments, as described above for concentrator 17. Proteolytic enzymes may be immobilized to the analyte-concentrator-microreactor to carry out microreactions, such as the cleavage of a protein into peptide components. In the microreactor or bioreactor, a number of chemical and/or biochemical reactions can be performed involving a large number of affinity ligands to be immobilized to the microreactor. For example, peptide synthesis, nucleic acid synthesis, small molecular weight substances synthesis can be accomplished in a small scale. The entrapment of viruses, cells, or subcellular structures may also be used to study metabolic pathways and degradation products of small molecular weight substances, as well as biomolecules.

The concentrator 17 generally includes matrix-like assembly or resin material that captures a larger number of analytes as well as a greater variety of analytes than the concentrators 34, 36, and 38. The concentrators 34, 36, and 38 may include corresponding matrix material including high-specificity immobilized affinity ligands that may be more selective than the matrix material including non-specific immobilized affinity ligands used in the concentrator 17. As a consequence, the matrix in the concentrators 34, 36, and 38 may capture or isolate a smaller quantity of analytes than the concentrator 17, but more selective and pure desired analytes, so that the captured analytes are more concentrated than in the original biological fluid cell, tissue, organ, or any other simple or complex matrix. The selectivity of the concentrator 34, 36 and 38 comes from the antibody capable of recognizing a specific area in a particular analyte called the epitope (e.g., a monoclonal antibody recognize a single epitope, a polyclonal antibody recognized multiple epitopes). Some analytes may have abundant amount of sugars or additional components on the surface of the molecule (e.g., certain glycoproteins) that may hinder the binding process to a specific peptide sequence. To better enable the capture of complex analytes, such as bulky and complex biomolecules, concentrator 34, 36, and 38 may contain two or more affinity ligands components. For example, a combination of a specific antibody and a specific lectin may be placed inside the concentrator to be able to capture a particular type of analyte through a selective peptide and/or epitope or through a selective sugar present on the analyte or to both. The specific attraction of each component to a different portion of the analyte may increase the number of complex analytes being attached.

FIG. 11A illustrates a cross-sectional view of the FIG. 10 where the valves on the transport capillary are in the second or closed position to substantially prevent the sample solution from passing towards the concentrator. The valves on the separation capillary are in the first or open position to allow the buffer solution to pass through the concentrator. The frits 35 surrounding the concentrator substantially retain the matrix-like assembly 37 within the concentrator.

FIG. 11B illustrates that the transport capillary 24 may be staggered from one separation capillary to another to form a concentration area 34 that is elongated. This allows additional matrix-like assembly 37 to be incorporated into the concentration area 34 to attach a desired analyte from the sample solution. In addition, the sample solution may take more time to pass through the elongated concentration area 34, which allows the matrix-like assembly additional time to bind to the desired analyte from the sample solution. The concentration area 34 may be surrounded by fits or porous end plates 35 to retain the matrix-like assembly 37 within the concentration area 34.

Figure 12:
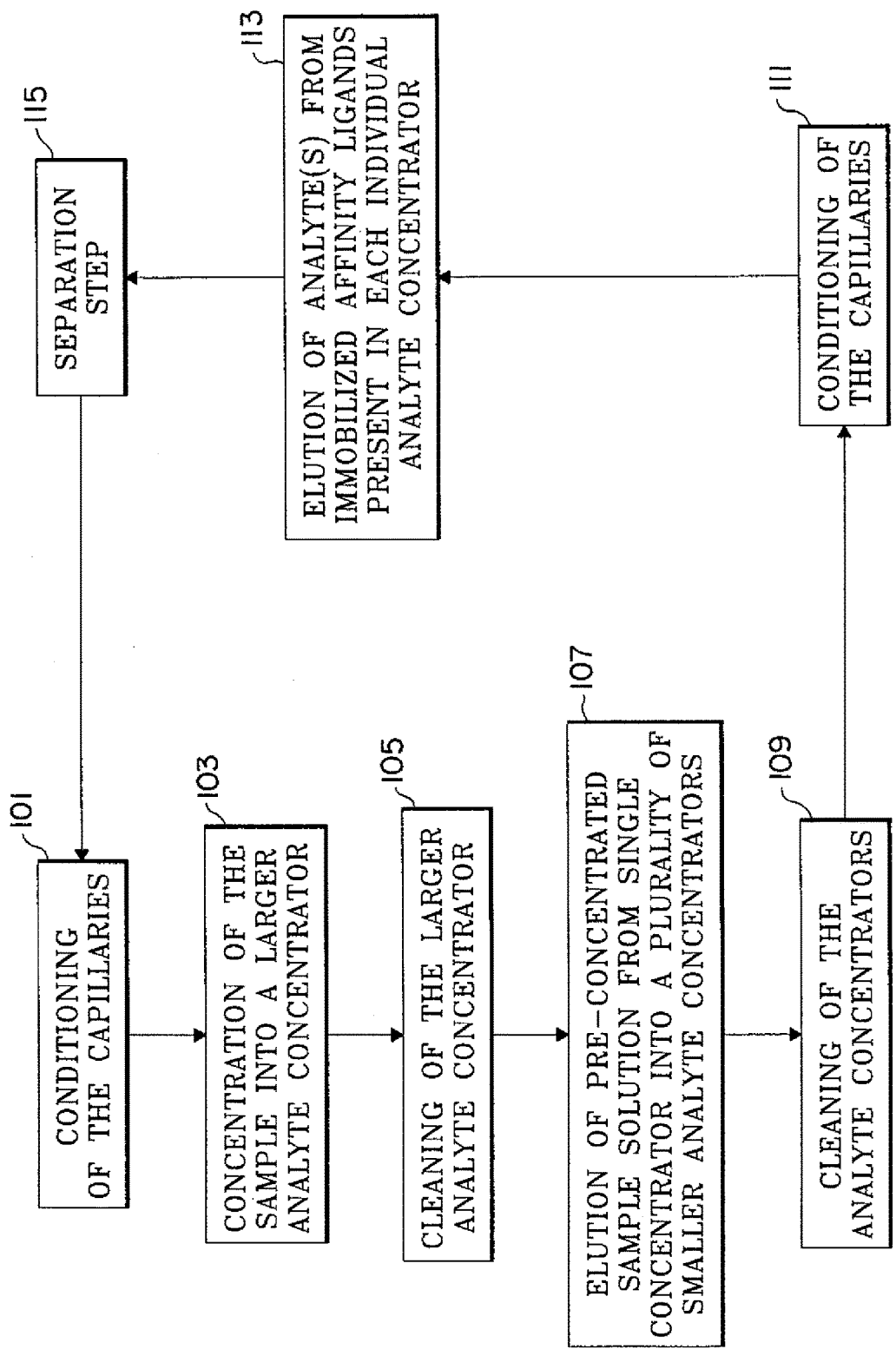
FIG. 12 illustrates the steps that may be taken to concentrate, isolate, and separate the desired analytes from the sample solution.

FIG. 12 illustrates the steps that may be taken to concentrate, isolate, and separate the desired analytes from the sample solution provided in the sample cup 15. A first conditioning step 101 prepares the transport and separation capillaries to a desired condition. This may be accomplished by passing conditioning buffer solution through the transport and separation capillaries. The conditioning step 101 may improve the binding properties for the immobilized affinity ligands so that once the desired analyte is attracted, it is retained by the immobilized affinity ligands for as long as the optimized conditions are maintained. The conditioning buffer solution may be provided through the transport capillary 24 and/or the separation capillaries 28, 30, and 32.

Once the capillaries have been conditioned with a conditioning buffer or solution, the sample solution in the cup 15 may be introduced through the transport capillary 24. For a large capacity concentration step 103, the valve 18 may be closed and the concentrator 17 is used to obtain the concentrated sample of desired analytes. The concentrator 17 may have more surface area for greater capacity to capture the desired analytes than the other concentrators used in the valving system 100. In general, the concentrator 17 may be used for more complex matrices where several analytes may be present in the sample. For instance, the concentrator 17 may be used when hundreds or thousands of analytes are present in the sample. On the other hand, when isolating certain compounds present in simple matrices, there may not be a need for the concentrator 17, tube 20, and waste cup 22 (depicted in FIG. 9). Examples of simple matrices include microdialysates, artificial matrices containing standard compounds, etc. In such instances, the samples solution may be introduced directly to transport capillary 24 from the cup 15 containing the simple matrix.

The isolation or concentration of the desired analytes may be done in a different location and time. The concentrated analytes may then be provided to the transport capillary 24 at a later time. The independence of the concentrator 17 from the apparatus 10 allows the concentrator 17 to be removed and replaced with a new concentrator without altering the apparatus 10. In addition, a plurality of original samples may be provided in a plurality of cups that are positioned along a rotatable table or through an appropriate fraction collector or the like, to provide the sample solution in each cup to the transport capillary 24 in intervals as the table rotates or moves, thereby providing multiple samples to the transport channel 24. Similar rotatable table may be used to change buffer solutions present in cups 40, 42, and 44.

After the sample solution has been introduced into the transport capillary 24 and passed through concentrator 17, in step 105, the concentrator 17 may be cleaned. This may be accomplished by passing copious amount of cleaning buffer to the concentrator 17 followed by conditioning buffer from another cup 15', replacing cup 15, through capillary 20 and towards waste cup 22. At this stage the bound compounds to concentrator 17 can be removed or eluted out of the concentrator 17. In the elution step 107 of FIG. 12, analytes retained by the concentrator 17 can be eluted from the concentrator 17 in many ways. One way is to pass a small amount or plug of an appropriate elution or desorption solution through the concentrator 17 to remove the bound analytes to the transport capillary 24. The bound analytes from the concentrator 17 are passed through the transport capillary 24 so that the concentrators 34, 36, and 38 may further isolate the desired analytes in each of the concentrators 34, 36, and 38. The removal of the bound compounds can be carried out as a group (simultaneously), or one or more at the time (stepwise or sequential). For isolating the desired analytes, which are cleaner or more pure and more concentrated than the original sample solution, provided in the sample cup 15, a plurality of concentrators containing more selective affinity ligands in this matrix may be used, such as concentrators 34, 36, and 38 along the transport capillary 24 with the purpose of individually capturing a single or a more reduced number of compounds than those bound to the concentrator 17. Accordingly, there may be two concentration steps in the invention: in the first concentration step, the concentrator 17 may be used to clean or purify the sample solution from a complex mixture; and in the second concentration step, the cleaned sample solution is passed through the concentrators 34, 36, and 38 to isolate the desired analyte(s) into each of the concentrators 34, 36, and 38 to isolate the desired analyte(s) that is different than the other.

To allow the sample solution to flow through the concentrators 34, 36, and 38, the valves 18, 102, 106, 112 and 118 along the transport capillary 24 may be opened; but to prevent the sample solution from flowing through the separation capillary, the valves 104, 108, 110, 114, 116, and 120 along the separation capillaries may be closed so that the sample solution does not flow to the buffer solution cups 40, 42, and 44, nor towards the detection system. Each of the concentrators 34, 36, and 38, may be filled with matrix-like assembly that are free-floating or chemically bonded microstructures, or polymeric monolithic matrices, containing appropriate selective and/or non-selective affinity chemistries. The concentrators may contain frit structures or be fritless.

As the sample solution passes through the concentrators, each of the concentrators may isolate the desired analyte(s) from the sample solution as discussed above. The excess sample solution may pass through the other end of the transport capillary 24 to the waste container 27. To optimize the binding, the valves 102 and 118 may be closed along transport capillary 24, to allow the analytes present in the sample solution to have a longer period of time to be exposed to the matrix-like assembly with corresponding immobilized affinity ligands bound to the particles or microstructures in each of the concentrators 34, 36 and 38. Alternatively, an elongated concentration area 34 as disclosed in FIG. 11B may be provided to expose the sample solution to the matrix-like assembly for a longer period of time and a longer surface area to capture larger amounts of desired analyte(s).

With the valving system 100, each of the concentrator areas may be localized so that an appropriate temperature, for example, may be controlled to each of the concentrator areas to improve the condition for the desired analyte to bind to the immobilized affinity ligands in the respective concentrators 34, 36, and 38. The desired temperature for the binding to occur may vary for each analyte. For example, the desired temperature may be at 25 C rather than at 37° C., or vice-versa, or even higher or lower than these temperatures. Each concentrator may have an independent temperature control to optimize the binding. In some instances, a gently shaking or use of a microwave pulse or acoustic micromixing system may aid in the binding process. For example, the use of a microwave pulse can accelerate the work of proteases and reduce the time required to cleave a protein into its peptide components.

With the desired analytes isolated in the concentrators 34, 36, and 38 in step 107, the isolated analytes in the concentrators 34, 36, and 38 may be cleaned, in the cleaning step 109. The cleaning step 109 removes remaining salts and unwanted materials present in the enriched sample solution passed from concentrator 17. This may be done by passing the cleaning solution through transport capillary 24 or through the separation capillaries. The cleaning solution washes away at least some of the salts and unwanted materials while the immobilized affinity ligands in each of the concentrators 34, 36, and 38 maintain its bind on the desired analyte(s). The cleaning step 109, however, may weaken the binding properties for the immobilized affinity ligands in the concentrators 34, 36, and 38. As such, once concentrators are clean, a second conditioning step 111 of the capillaries may be provided to once again improve the binding properties of the immobilized affinity ligands in the concentrators 34, 36, and 38. The separation capillaries 28, 30 and 32 may be conditioned until they are equilibrated with a conditioning buffer present in cups 40, 42 and 44.

In the second elution step 113, the elution buffer is used for releasing the desired analyte from the immobilized affinity ligands in the concentrators 34, 36, and 38. The amount of a plug of elution buffer that is needed to release the desired analyte from the immobilized affinity ligands may vary. In general, about 50 to about 200 nanoliters of the elution buffer may be used. Also, as the size of the internal diameter of the capillary increases, greater amount of the elution buffer solution may be used. The condition of elution buffer may be gentle as possible so that the capturing properties of the immobilized affinity ligands remain intact in the surface of the particles or microstructures, or in a portion of the inner wall of the capillary so that it may be reused.

In the separation step 115, the separation buffer is used to separate the analyte(s) released from the concentrators. The separation buffer may be provided through cups 40', 42' and 44'. In some instances, the conditioning buffer and separation buffer may be the same. The composition of each conditioning and separation buffer for each separation capillary may be the same or different. For the conditioning and separation step, the valves 102, 106, 112, and 118 on the transport capillary 24 may be closed and valves 104, 108, 110, 114, 116, and 120 on the separation capillaries 28, 30 and 32 may be open. At this stage the desired analytes bound to the concentrators 34, 36, and 38 may be released sequentially or simultaneously using a small plug of desorption solution. If analytes are released in a sequential order, they can be released from concentrators 34, 36, and 38 in any order. For example, to release the analyte(s) retained by the concentrator 36 first, the valves 110 and 114 are opened first with the valves 106 and 112 being closed. As mentioned above, this allows three buffer systems to be introduced to the separation capillary 30 from cup 42, creating an independent optimized microenvironment of conditioning, desorption and separation. The first buffer is a conditioning buffer. The second buffer is a separation buffer. The third buffer is a small plug of an elution or desorption buffer. The separation capillary can be temperature controlled where the separation capillary has a linear, coiled, serpentine configuration. In addition, each separation capillary may have a different configuration.

The buffers in the cup 42 may be changed using a variety of methods. For example, an autosampler, rotatable table or any other manual or automated device that holds a plurality of sample containers, vials, or cups, may be used. For instance, three cups may be needed for holding three different buffers, vials 42 (conditioning buffer), 42' (separation buffer), and 42" (elution buffer). For the separation step, a platinum-iridium electrode can be introduced to the cup 42 (high voltage side) containing the separation buffer. The electrode may, in turn, be connected to a high-voltage cable and a high-voltage power supply. On the opposite side of the separation capillary 30, a grounding electrode may be provided for grounding. When the power supply is switched on, the system is activated to begin the process of releasing and separating the analyte(s). The process of desorption or elution of the analyte(s) by the chemical constituents of the small plug of the elution buffer can occurs by moving the plug by pressure, or vacuum, or electrokinetically. Similar steps may be taken to release the analytes in the concentrators 34 and 38 in any order. For instance, to release the analyte isolated in the concentrator 34, the valves 102 and 106 may be closed and the valves 104 and 108 opened. Similar to a concentrator, each individual separation capillary 28, 30, or 32 may have an independently controlled temperature system. The capillary can be heated or cooled in a linear format or in a coiled configuration using a controlled-temperature fluid or device such as a Peltier.

As the analytes in the concentrators 34, 36, and 38 are released in a predetermined order, the detector 46 of FIG. 1 may be movable and aligned with the separation capillary corresponding to the concentrator that the analyte is released from. For instance, with the above example, if the analyte from the concentrator 36 is released first, then the detector 46 is first aligned with the separation capillary 30 to identify the analytes released from concentrator 36. Then, the detector 46 may be repositioned to align with the separation capillary 28 to detect the analytes released from the concentrator 34, and repositioned to detect the analytes passing through capillary 32 released from concentrator 38.

The valving system may communicate with a detection system for detecting the analytes released from the concentrators. The detecting system may operate in many ways. For instance, the detection system may include a detector for each separation capillary 28, 30, and 32. In another embodiment, the three separation capillaries may be merged into one exit capillary as shown in FIGS. 7 and 8, and one detector is aligned over the exit capillary. In this case, the detection system may have one detector that is fixed such that it can align over the detection window positioned in the exit capillary 66 for detecting the analytes passing through the exit capillary. For this operation, however, additional valves may be needed to direct the separated analytes from separation capillaries 28, 30, and 32 to the single detector. For example, when separation capillary 28 is active and analytes are separated within capillary 28, capillaries 30 and 32 may be inactivated, and the separation buffers may be blocked by the corresponding valves. The fixed detectors, 86 and 88, of FIGS. 7s and 8 may be a laser-induced fluorescence detector or a contactless electrochemical detector or a combination of similar detection devices. Furthermore, the outlet of the exit capillary may be connected to other detector systems, such as a mass spectrometer, including sample deposition onto a matrix assisted laser desorption/ionization (MALDI) plate, or a conductivity detector.

The analytes in the concentrators 34, 36, and 38 may be released simultaneously as well. This may be accomplished by closing the valves 102, 106, 112, and 118 along the transport capillary 24 and opening the valves 104, 108, 110, 114, 116, and 120 along the separation capillaries 28, 30, and 32. As the analytes in the concentrators 34, 36, and 38 are released simultaneously through the separation capillaries 28, 30, and 32, the detection of the separated analytes may be accomplished as described above. The capillary electrophoresis separation of the analytes in capillaries 28, 30, and 32 may require a single power supply with the appropriate high-voltage relays or multiple power supplies, each for a single column. With the valving system 100, the path that sample and buffer solutions flow through the transport capillary 24 and the separation capillaries 28, 30, and 32 may be controlled to localize the concentrators so that a customized environment for each analyte bound to the microstructures in the analyte concentrator may be formed. The separation of the analytes can occur using electricity (electroosmotic flow), controlled positive pressure or vacuum, or a combination of both.

Figure 13:
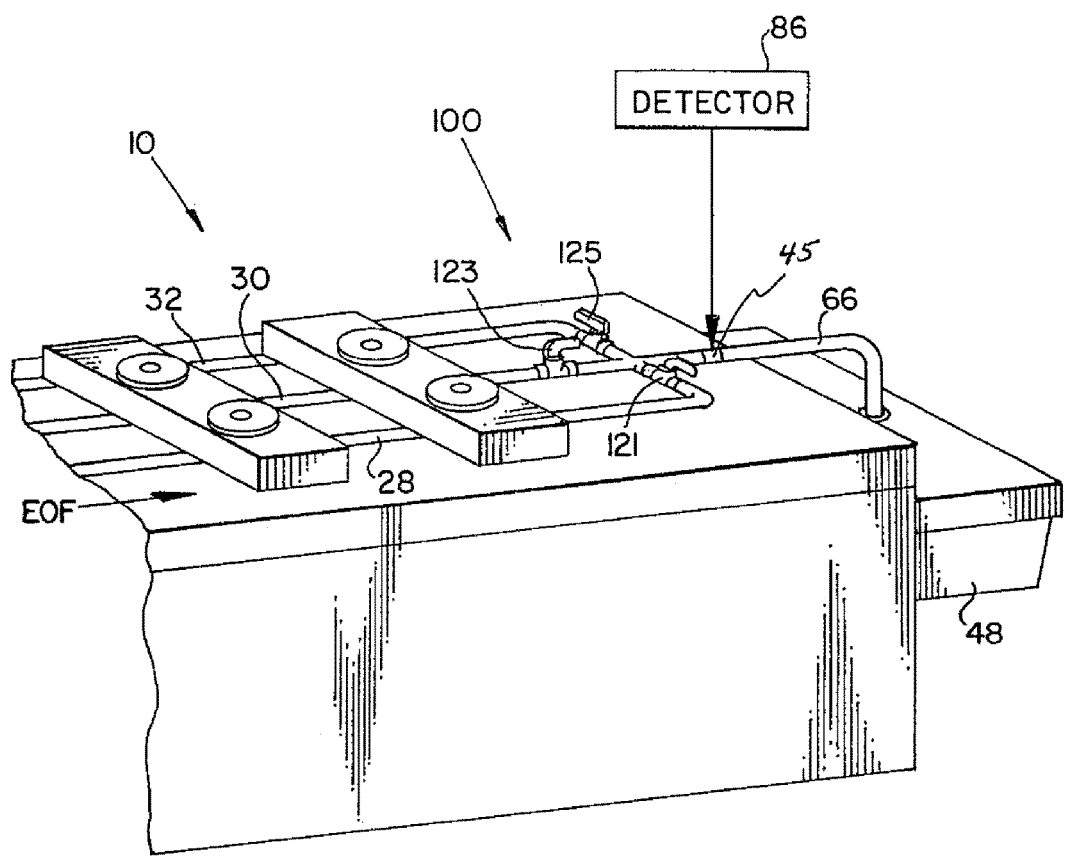
FIG. 13 is a perspective view of an electrophoresis apparatus having valves near the detector.

FIG. 13 illustrates an electrophoresis apparatus 10 including a valving system 100 having valves 121, 123, and 125 on the separation capillaries 28, 30, and 32, respectively, near the detection window 45. The output ends of the separation capillaries 28, 30 and 32 may be connected to each other at the interface with a single outlet capillary 66 which cooperates with on-column detector 86 that senses ultraviolet (UV) or fluorescent energy. The outlet of the outlet capillary 66 may also be connected (as shown) to a waste container 48. With the valves 121, 123, and 125, the analytes in the separation capillaries may be released to the output capillary 66 sequentially by opening one valve at a time. This allows the analytes in the concentrators 34, 36, and 38 to be released simultaneously but sequentially detect the analytes in each of the concentrators through the valves 121, 123, and 125. In addition, the valves 121, 123, and 125 may be synchronized with the valves surrounding the concentrators 34, 36, and 38 to release the analytes in the concentrators 34, 36, and 38 in a predetermined order.

Figure 14:
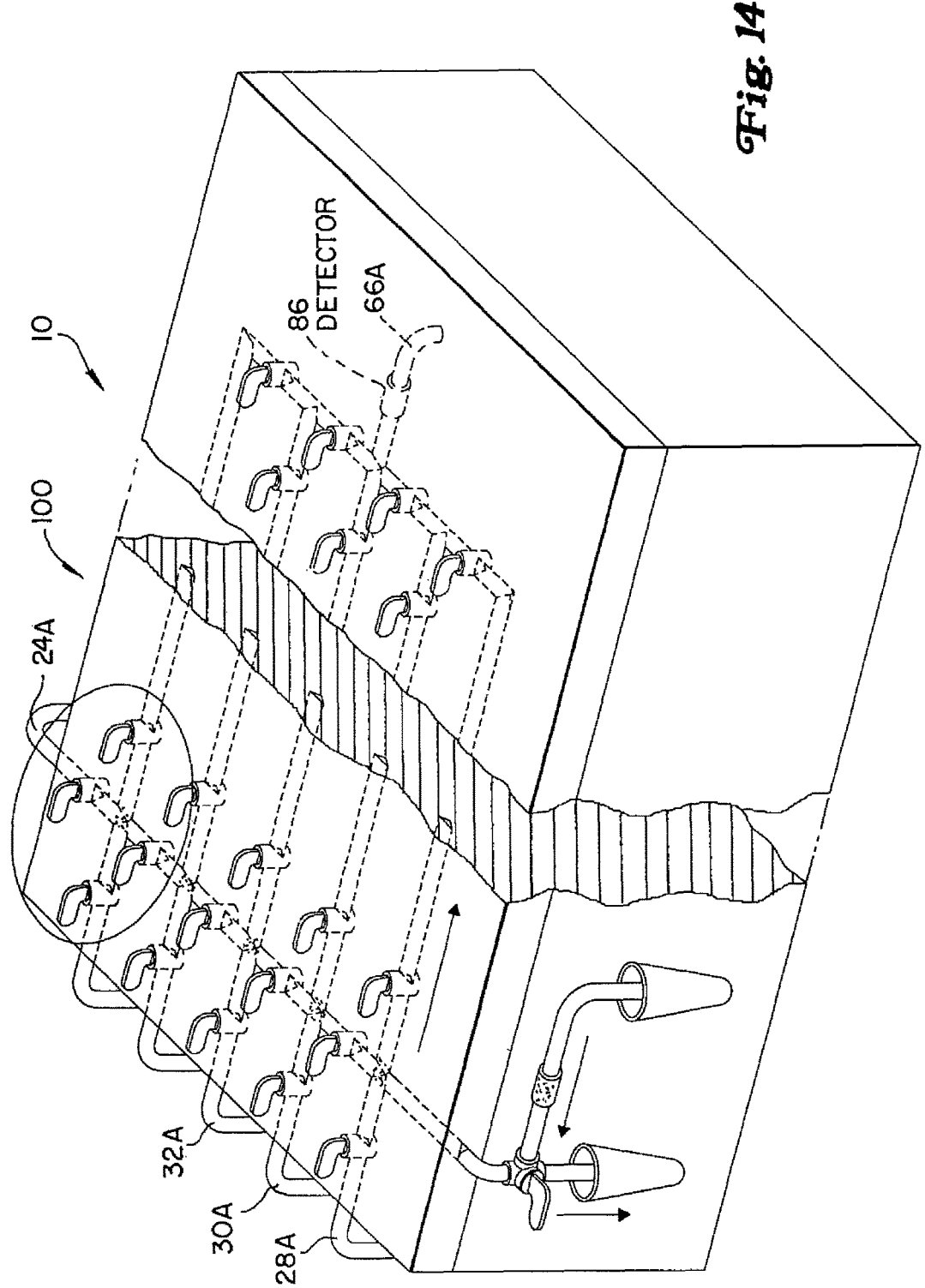
FIG. 14 is a perspective view of an electrophoresis apparatus having transport and separation channels with a valving system where the separation channels merge into one output channel.
Figure 15:
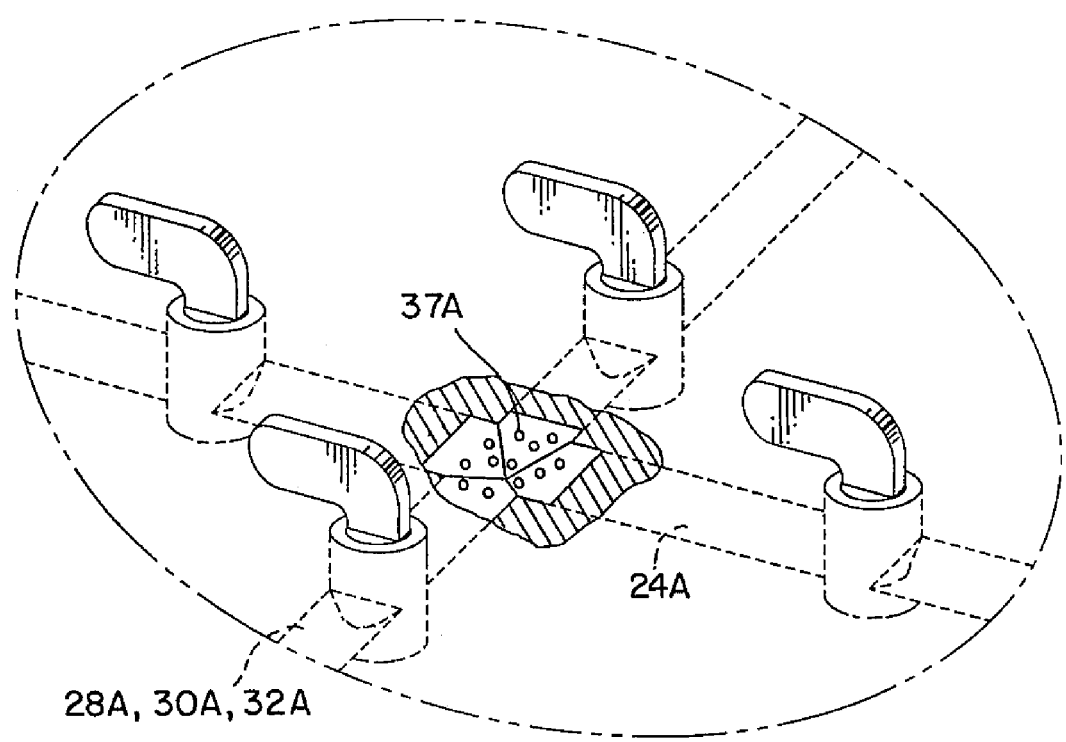
FIG. 15 is an enlarge view of one of the concentrators of FIG. 14.

FIG. 14 illustrates that the transport channel 24A and separation channels 28A, 30A and 32A, for the electrophoresis apparatus 10 may be formed with uniform and concave shapes that are engraved, etched or otherwise formed into a glass or plastic microchip using known lithography or other manufacturing techniques. Analyte concentrators 34A, 36A and 38A are disposed at the respective intersections of transport channel 24A and separation channels 28A, 30A and 32A with the valving system 100 to control the flow of fluid and microenvironment to each of the concentrators 24A, 36, and 38 as previously described. Near the detector 66, valves may be provided to control of fluid to the output capillary 66 from the plurality of separation capillaries. FIG. 15 illustrates that each concentrator formed by intersection of transport and separation channels may be surrounded by valves to control the flow of liquid through the transport channel 24A and the corresponding separation channel.

Figure 16:
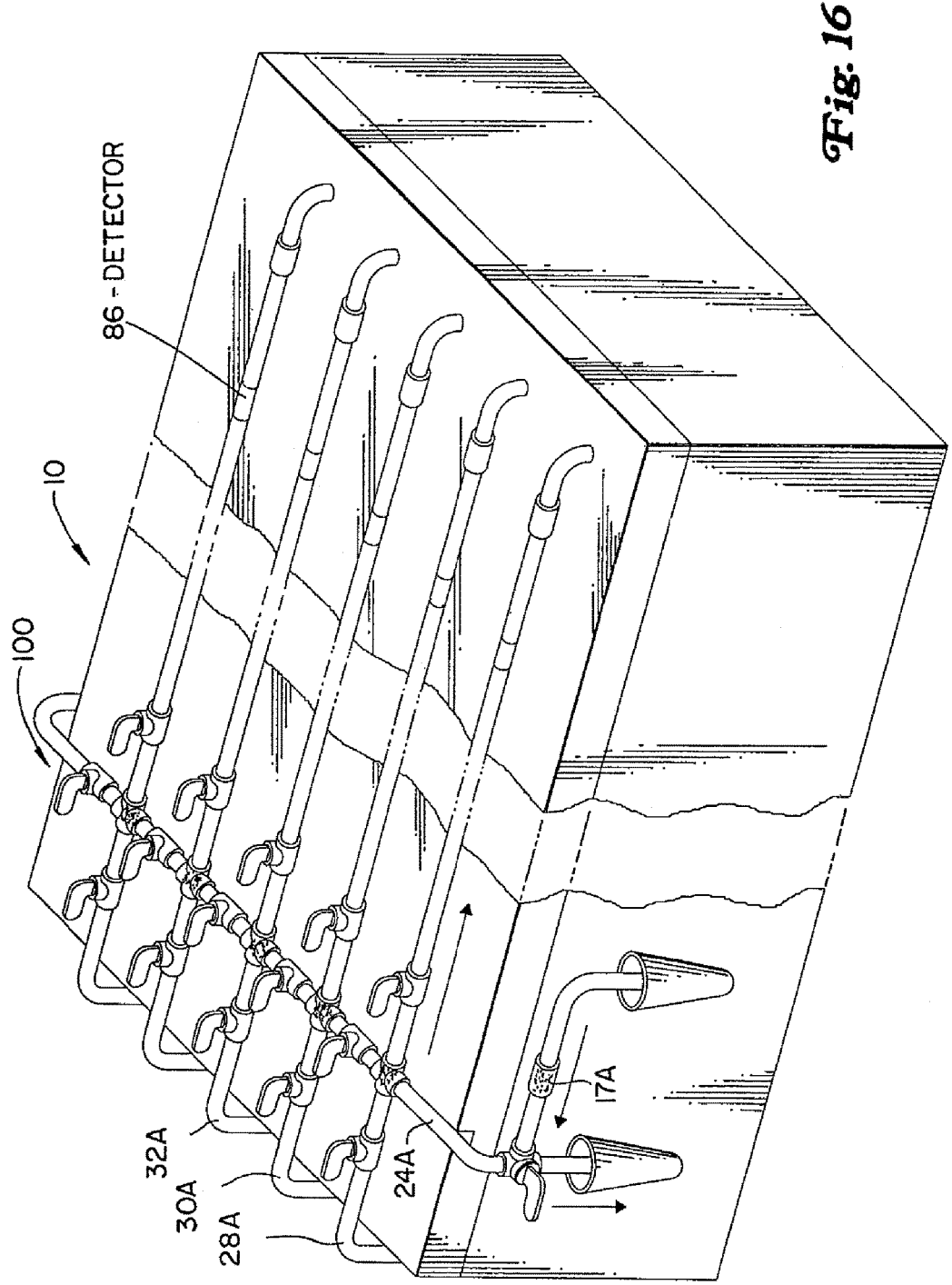
FIG. 16 a perspective view of an electrophoresis apparatus having transport and separation channels with a valving system.

FIG. 16 illustrates a perspective view of an electrophoresis apparatus 10 having a transport channel 24A and a plurality of separation channels 28A, 30A, 32A, and etc. Near the outlet side of the separation channels, a detector 86 may be provided that aligns with one of the detection windows of the separation channels to detect the analyte passing through the respective separation channels sequentially. To simultaneously detect the analytes passing through all of the separation channels, a detector may be provided for each separation channel to speed up the process.

Figure 17:
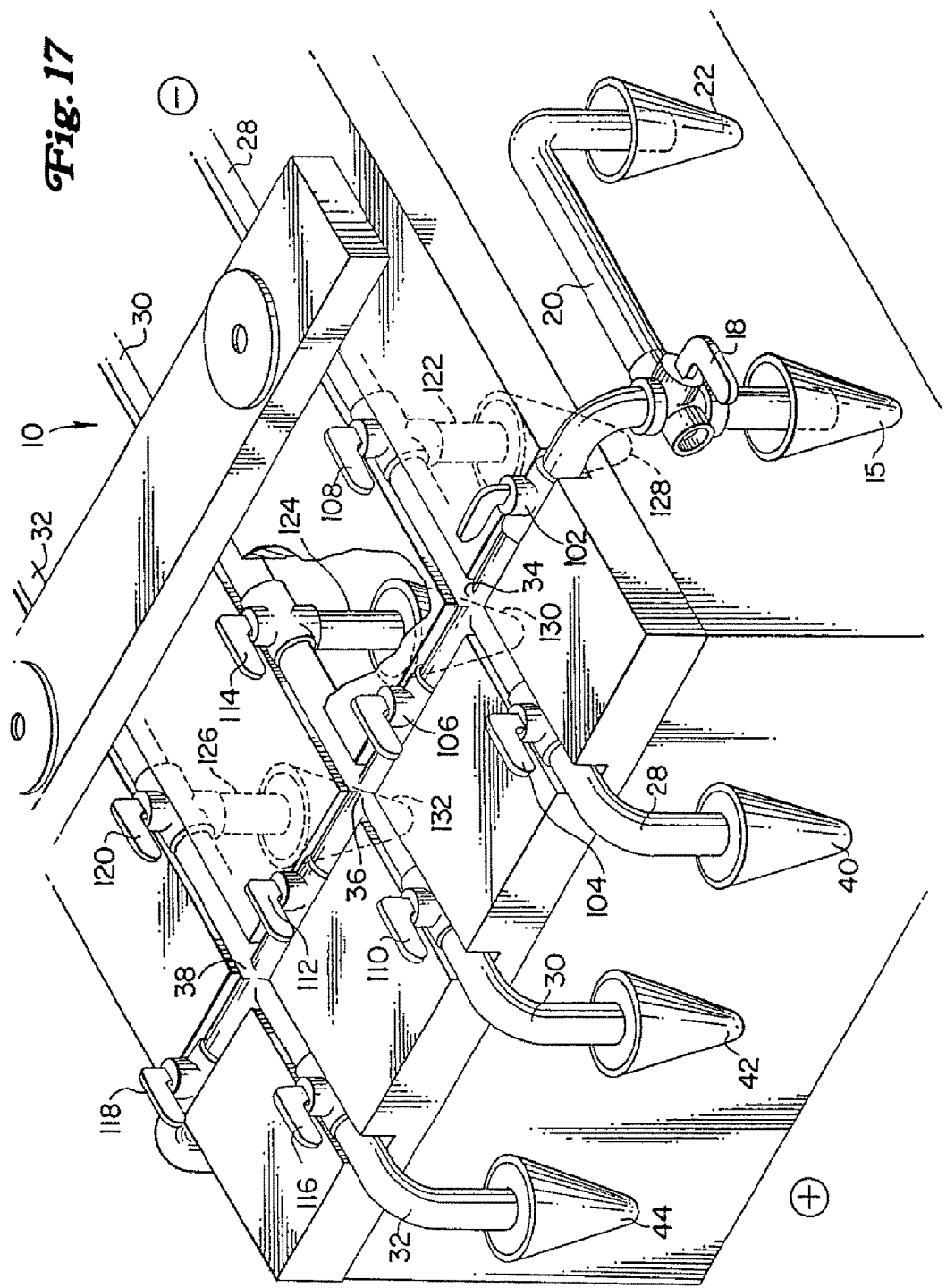
FIG. 17 is a perspective view of an electrophoresis apparatus with inlets in the separation capillaries downstream from the concentrators.

FIG. 17 illustrates that the new separation buffer solution may be added by auxiliary capillaries 122, 124, and 126 after or downstream from the concentrators in order to preserve the integrity of the antibody or any other immobilized affinity ligands. In certain applications the analytes under study may require for optimal separation from a separation buffer solution that may adversely affect the activity of the intact antibody, antibody fragment, lectin, enzyme, or any affinity ligands affected by certain compounds present in the separation buffer. Put differently, with certain separation buffer solutions may adversely affect the binding property of the immobilized affinity ligands in the concentrators so that the affinity ligands may not be used again. Also, the analytes may not be retained by the immobilized affinity ligands. With the auxiliary capillaries 122, 124, and 126, the separation buffer solution may be introduced into the separation capillaries using the cups 128, 130, and 132. This allows the separation buffer solution to flow towards the detecting zone so that there is minimal, if any, interaction between the separation buffer solution and the antibody in the concentrator. For example, the separation of an analyte may require the presence of organic solvents or other additives in the separation buffer solution such as urea, certain detergents, etc. If such separation buffer solution passes through the concentrator so that the separation solution interacts with the antibody in the concentrator, the separation buffer solution may disrupt the binding process between the analyte and the antibody during the conditioning process of the capillary and/or destroy the quality of the antibody in an irreversible manner. Such adverse effect on the antibody may destroy the integrity of the binding capacity of the antibody so that it may not bind to the analyte and/or may not be used again. To substantially prevent such adverse effect on the antibody, the antibody in the concentrator is isolated from such separation buffer solution to protect the immobilized antibody, or antibody fragments or other affinity element, such as a lectin or an enzyme.

In addition, the binding and separation conditions of a desired analyte may require different optimization conditions. In cases where the conditioning and/or separation buffer are different, one or more of the separation capillaries 28, 30, and 32 may be divided into two stages. In the first stage of the conditioning process, capillaries 28, 30, and 32 may be filled with the appropriate conditioning buffer located in the cups 40, 42, and 44, respectively, to improve the binding condition for the antibody. The conditioning buffers in the respective cups may pass through the open valves 104, 110, and 116, and pass through the concentrators 34, 36, and 38, and pass through the valves 108, 114, and 120, and then to the outlets of the separating capillaries. The valves 102, 106, 112, and 118 along the transport capillary may be closed to keep the conditioning buffer within each of the separation capillaries.

FIG. 17 illustrates cups 128, 130, and 132 located on the second stage of the separation capillaries 28, 30, and 32. The cups 128, 130, and 132 may be coupled to the corresponding separation capillaries through auxiliary capillaries 122, 124, and 126, respectively. The cups 128, 130, and 132 may hold separation buffer solutions that are feed into the separation capillaries 28, 30, and 32 downstream from the concentrators 34, 36, and 38, respectively. The auxiliary capillaries 122, 124, and 126 used to couple the cups 128, 130, and 132 to the separation capillaries 28, 30, and 32 may be electrolyte-provider capillaries (EPCs). The auxiliary capillaries 122, 124, and 126 may be coupled to the respective separation capillaries 28, 30, 32, downstream or after the concentrators 34, 36, and 38 so that the buffer solutions flow towards the detecting window 45. The auxiliary capillaries 122, 124, and 126 may be also coupled to the valves 108, 114, and 120 downstream from the concentrators 34, 36, and 38 to control the flow of the buffer solution into the separation capillaries 28, 30, and 32 by opening and closing the valves 108, 114, and 120. This way, the buffer solutions generally do not interact with the immobilized antibodies in the concentrators 34, 36, and 38. With the cups 128, 130, and 132 positioned downstream from the concentrators in the apparatus 10, the separation buffer may be introduced into the apparatus 10 either before the concentrators using the cups 40, 42, and 44, or after the concentrators using the cups 128, 130, and 132, depending on the interfering of the separation buffer on the binding between the analyte(s) of interest and the immobilized affinity ligands in the concentrators 34, 36, and 38 and/or the damage that the constituents of the separation buffer can do to the immobilized affinity ligands.

In applications where the separation buffer does not adversely affect the antibody, the separating buffer solution may be introduced into the separation capillary before the concentrator through the cups 40, 42, and 44 as discussed above. For applications where EPCs are used, the concentration step is similar to the step discussed above. For the eluting and separating steps, the valves on the separation capillaries 28, 30, and 32 may be opened sequentially or simultaneously to perform the process of simultaneous elution and separation of the analytes present in all of the concentrators and separation capillaries, the valves along the transparent capillary 24 may be closed, and the valves 104, 110, and 116 along the separation capillaries 28, 30, and 32 may be opened first. The eluting buffer solution flows through the separation capillaries 28, 30, and 32 to elute the analytes bound to the antibodies in the concentrators 34, 36, and 38, respectively. This causes the analytes to be released from the immobilized antibodies or antibody fragments, or other affinity ligands.

For the separating step in which a separation buffer for optimized separation of the analytes is needed, but may cause disruption of the binding between the analyte and affinity ligands or may damage the integrity of the affinity ligands, the valves 108, 114, and 120 may be opened to allow the separation buffer solutions in the cups 128, 130, and 132 to allow an optimized separation of the release analytes down stream from the concentrators. The separating buffer solution may enable the separation of the analytes under improved conditions so that one analyte or other closely related analyte(s) that have selectively bound to the immobilized ligands may be separated achieving a basedline resolution after elution from their respective analyte concentrators.

Figure 18:
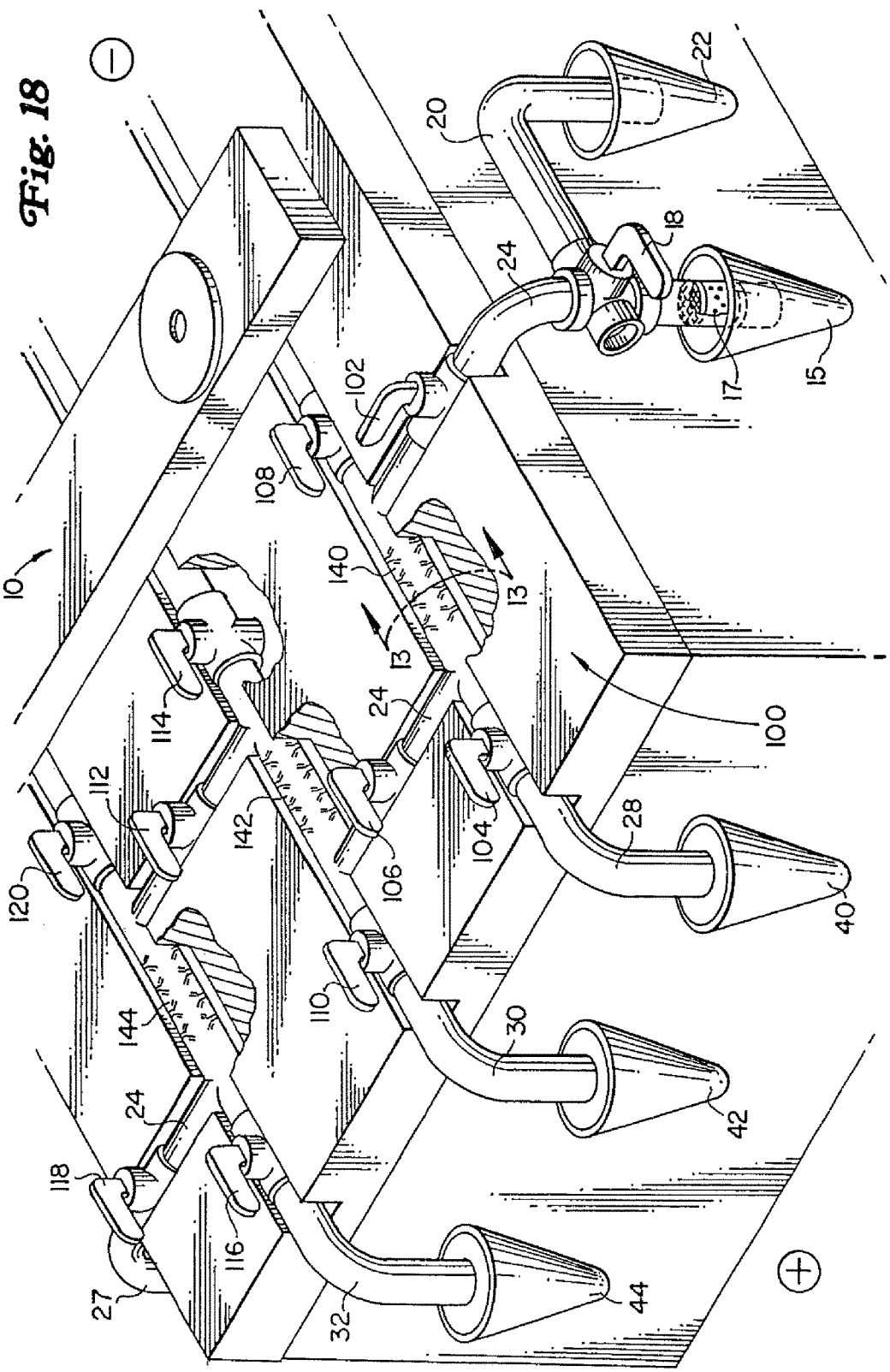
FIG. 18 is a perspective view of an electrophoresis apparatus with a staggered transport capillary forming a concentration area that is elongated.

FIG. 18 illustrates another embodiment of electrophoresis apparatus 10, configured to capture and detect primarily large sized particles such as cells, organelles, and/or other bulky globule structures. The large particles may require a larger cross-sectional area for the particles to pass through without blockage or interference during separation. The configuration where the affinity ligands are immobilized on the surface of a bead, or cross-linked, or on monolithic structures may not be appropriate for the separation of globule structures. The blockage may occur in such situations and may prevent the separation of such structures from occurring. This embodiment may also be used to capture and detect small molecules and bio-molecules.

Figure 19:
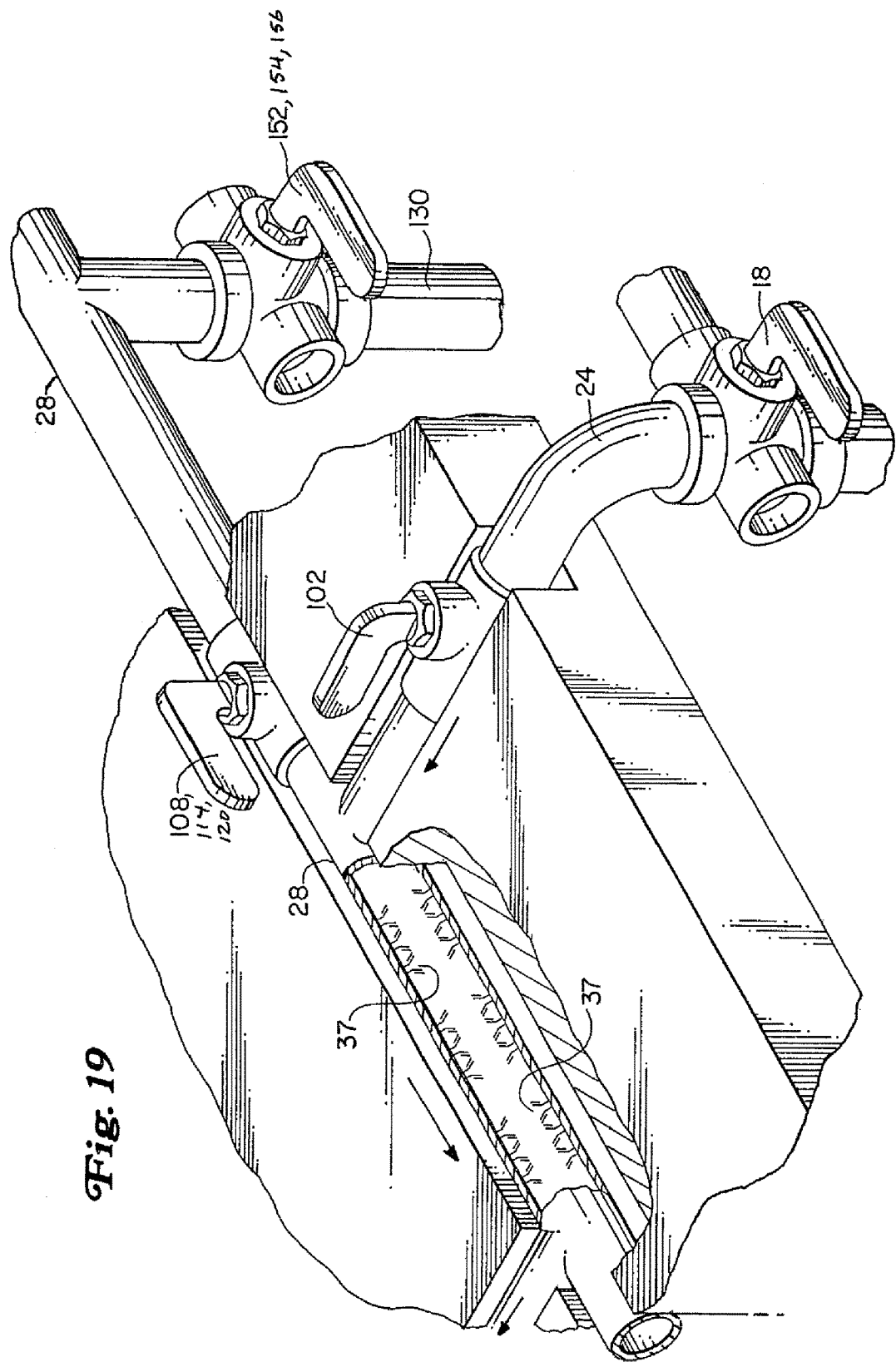
FIG. 19 is an enlarge view of one of the concentrators with affinity elements covalently bonded to the inner wall of the separation capillary.

FIGS. 18 and 19 illustrate the electrophoresis apparatus 10 having matrix-like assembly antibodies along the interior surfaces of the separation capillaries 28, 30, and 32. That is, the affinity 37 elements may be also covalently bonded directly to the inner wall of the capillary or to beads covalently bound to each other and also bound to the inner wall of the capillary. The use of covalent bonds to bind beads within a matrix is also described in U.S. Pat. No. 5,202,010, which is referred to as beaded capillaries. The attachment of beads to the capillary through covalent bonds may produce strong bonds that can hold the beads in the predetermined location along the capillary.

Figure 20:
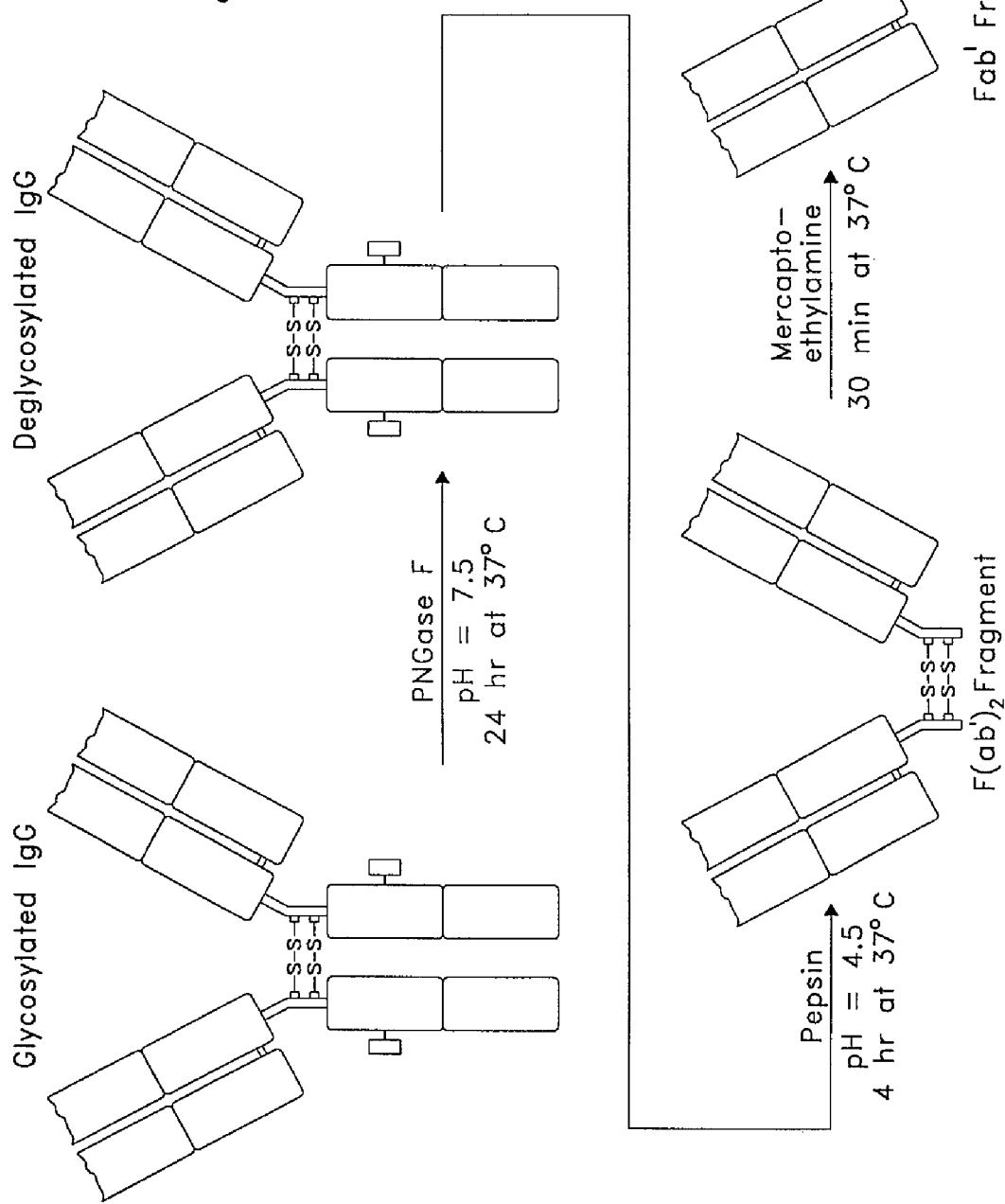
FIG. 20 illustrates the process undertaken to isolate the monovalent antibody fragment Fab'.
Figure 21:
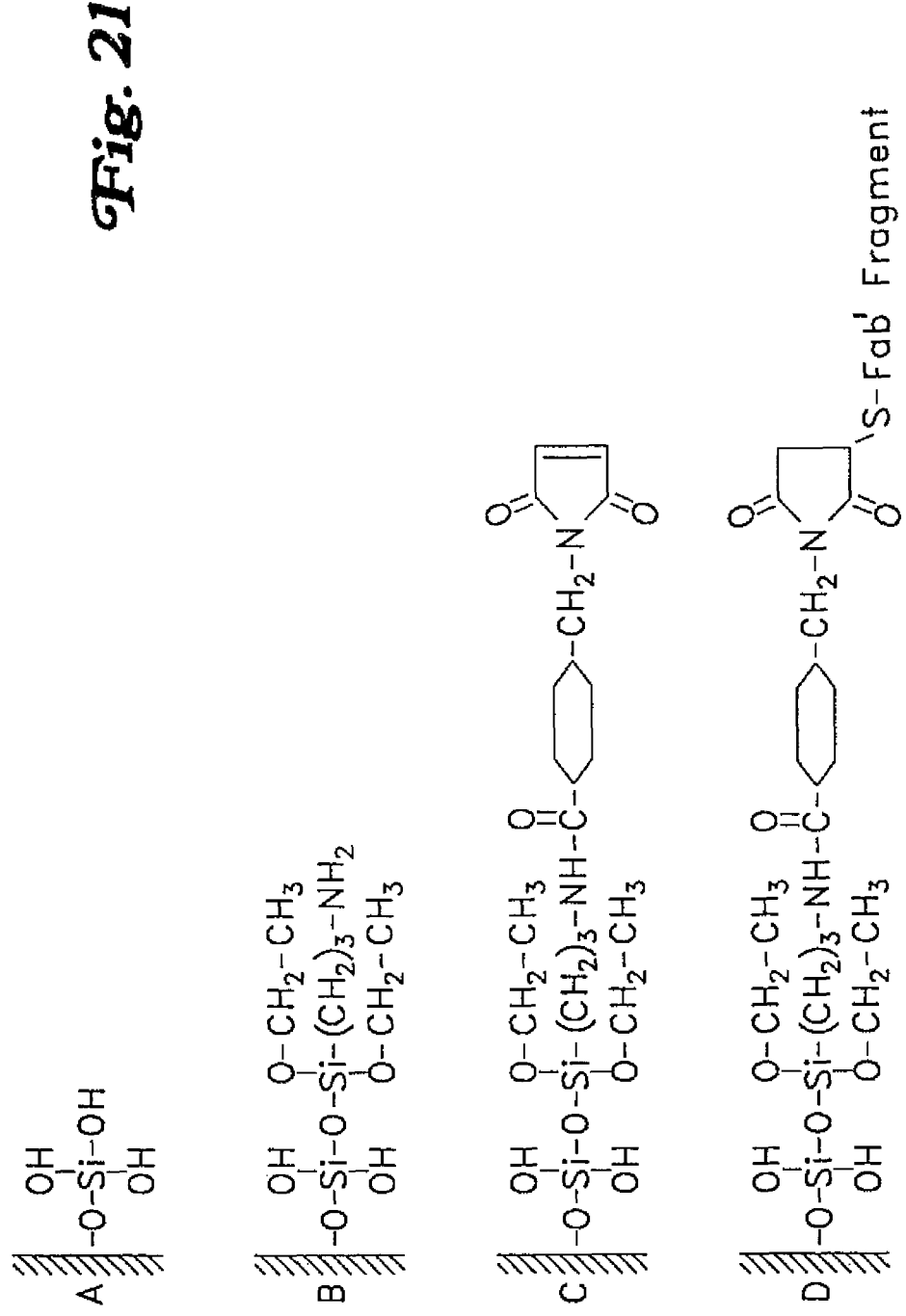
FIG. 21 illustrates various chemical reactions used to covalently immobilize an antibody or antibody fragment to the surface of controlled-pore glass beads or to the surface of the inner wall of a separation capillary, where the silanol groups of the surface of the beads or inner wall of the separation capillary were silylated with 3-aminopropyltriethoxysilane and then reacted with SSMCC before being conjugated to a monomeric Fab' fragment.

FIG. 20 illustrates the process undertaken to isolate the monovalent antibody fragment Fab'. The antibodies may be obtained by subjecting purified IgG antibody to two partial enzymatic digestions to obtain F(ab')2 fragment. The resulting F(ab')2 antibody fragment may be further reduced to produce monovalent Fab' antibody fragments. As shown in FIG. 21, the Fab' antibody fragment attaches to the inner wall of the capillary by creating cross-links or bridge chemistries between a sulfhydryl group of the antibody fragment Fab' and an amino group of a chemical arm bound to the silanol groups of the inner surface of the fused-silica (quartz) capillary or the surface of beaded structures or polymeric microstructures having terminal silanol groups. The antibody fragments attaches to the surface of the separation capillary in an orientation that facilitates the binding of the antibody and the desired analyte. A proper orientation of the Fab' antibody fragments results in an increased surface area of the analyte-concentrator to provide greater capacity to capture the desired target analyte. A number of antibodies that have affinity to a predetermined antigen or hapten may be provided along a predetermined portion of one or more separation capillaries 28, 30, and/or 32. An antigen is a chemical compound that normally causes the body to produce an antibody when the immunological system in the body recognizes it. A hapten is a chemical compound that normally does not produce an antibody because it is too small and may not be recognized by the immunological system. To produce an antibody for a hapten, the hapten may be bound to an immunogenic carrier (e.g., albumin, hemocyanin, etc.). This may allow the immunological system to recognize the package (hapten-carrier) as foreign, causing the development of an antibody. As discussed above, the concentrator 17 may provide a number of analytes of interest to the valving system 100 through the transport capillary 24. To identify the predetermined number of analytes of interest, each separation capillary 28, 30, and 32 may be provided with an antibody that has affinity to a particular analyte. For example, as illustrated in FIG. 18, a first type of antibodies 140 that have affinity to a first analyte provided by the concentrator 17 may be provided within the interior wall of the separation capillary 28. Likewise, a second type of antibodies 142 and a third type of antibodies 144 that have affinity to a second analyte and third analyte may be provided within the interior walls of the separation capillaries 30 and 32, respectively.

FIG. 18 illustrates a valving system 100 that allows the concentrated analytes from the concentrator 17 to pass through the first, second, and third antibodies 140, 142, and 144. The transport capillary 24 may be staggered from one separation capillary to another to form an elongated analyte concentrator. For instance, the transport capillary 24 is staggered at the separation capillaries 28, 30, and 32 forming elongated analyte concentrators 140, 142, and 144. To pass the concentrated analytes through the valving system 100, the valves 104, 108, 110, 114, 116, and 120 along the separation capillaries 28, 30, and 32 may be closed, and the valves 102, 106, 112, and 118 along the transport capillary 24 may be opened. Once the output valve 18 is opened, and the analytes bound to the concentrator 17 are eluted, as described in step 107 in FIG. 12, so that the concentrated analytes of interest flow through the first, second, and third types of antibodies 140, 142, and 144. As such, the antibodies that have affinity to a particular type of analyte may bind to that analyte. For example, as the concentrated analytes pass through the first antibodies 140, the first analytes of interest from the concentrated analytes from the concentrator 17 couple to the first antibodies 140, then as the remaining concentrated analytes pass through the second and third antibodies 142 and 144, the second and third analytes of interest couple to the second and third antibodies, respectively. The remaining concentrated analytes can then be discarded to the waste container 27.

With the desired analytes bound to the antibodies 140, 142, and 144, the conditioning, separating and eluting buffer solution from the cups 40, 40', 40", 42, 42', 42", and 44, 44', 44" may be provided to the immobilized antibodies or antibody fragments, to release and separate the bound analytes from the immuno complex. This may be accomplished by closing the valves 102, 106, 112, and 118 along the transport capillary 24, and opening the valves 104, 108, 110, 114, 116, and 120 to provide the separation buffer solutions from the cups 40, 42, and 44. For the separating step, the separating buffer solution may be provided either through the cups 40, 42, and 44 or through the cups 128, 130, and 132 as discussed above in FIG. 17. To capture cells, organelles, and/or other bulky structures, the concentrator 17 may not be needed.

FIG. 19 also illustrates the addition of valves 152, 154, and 156 to control the flow of buffer solutions in cups 128, 130, and 132 into the respective separation capillaries 28, 30, and 32. The valves 108, 114, and 120 are opened when the capillaries 28, 30, and 32 are filled with conditioning buffer from cups 40, 42, and 44. Then the valves 152, 154, and 156 may be opened to allow the separation buffer from the cups 128, 130, 132 to enter into the respective auxiliary capillaries 28, 30, and 32. As the electric charge creates an electroosmotic flow in the direction of the detection zone, the separation buffer entering the capillaries 28, 30, and 32 downstream from the concentrators flow towards the detection zone as well. The electroosmotic flow created by the electricity moves the analytes along the separation buffer towards the detection system, allowing separation of the elements to take place.

Having the antibodies within the interior surface of the separation capillary may provide a larger surface area of antibodies if the length of the surface is several centimeters, for example. In other words, more antibodies may be provided along the longer path that the concentrated analytes flow through. This means that greater quantity of a particular type of analyte may be isolated from the concentration of analytes. In addition, with the valving system 100, a number of different types of analytes in greater quantity may be identified through the different types of antibodies 140, 142, and 144. The diameter of the separation capillaries may be varied so that large size analytes such as cells, subcellular particles, or globules may pass through the separation capillaries and couple to the corresponding antibodies. Accordingly, a variety of analytes with a wide range of sizes may be isolated with the antibodies along the inner surface of the capillaries. In addition, the concentrators may be utilized as a capture matrix to purify at least one type of analyte present in a simple solution that has reduced number of chemical and/or biochemical compounds. The concentrator may be also utilized to purify at least one analyte from a complex solution that has greater number of chemicals and/or biochemical compounds than the simple solution. With the concentrator, a variety of chemical reactions may be performed such as multi-component chemical reactions, biochemical reactions, and multi-component biochemical reactions.

The length of the portion of the capillary in which the antibodies are bound along the separation capillary may vary. For example, the antibody 140 formed within the separation capillary 28 may be shorten or elongated depending on the quantity of the analytes to be isolated. For greater quantity, the length of the antibody formed along the capillary 28 may be lengthened.

FIG. 22 illustrates a separation capillary 28 having more than one type of antibodies within its interior wall between the valves 104 and 108. The separation capillary 28 may be divided into many portions, where each portion has one type of antibodies to isolate a particular type of analyte. For example, the separation capillary 28 may have different types of antibodies 140, 150, and 160 each having affinity to different type of analyte. As such, the separation capillary may isolate a number of different types of analytes. The separation capillary 28 may be elongated to incorporate more antibodies if desired. The transport capillary 24 may be coupled to the separation capillary 28 near the valve 108 to provide the concentrated analytes from the concentrator 17. As the concentrated analytes pass through the separation capillary 28, each of the antibodies may couple to the desired analytes.

A certain antibody may require a different eluting buffer solution to cause that antibody to release the analyte. In such a case, a number of eluting buffer solutions may be provided through valve 104 so that all of the antibodies release its analyte. After the eluting step, the separation buffer solution may be provided through the valve 104 as well. Alternatively, to minimize the adverse affect on the antibodies, the separation buffer solution may be provided down stream from the last antibodies 160 through the EPC 122 as discussed above. The separated analytes are then pass through the detecting zone 45 to identifying the individual analytes.

Figure 23A:
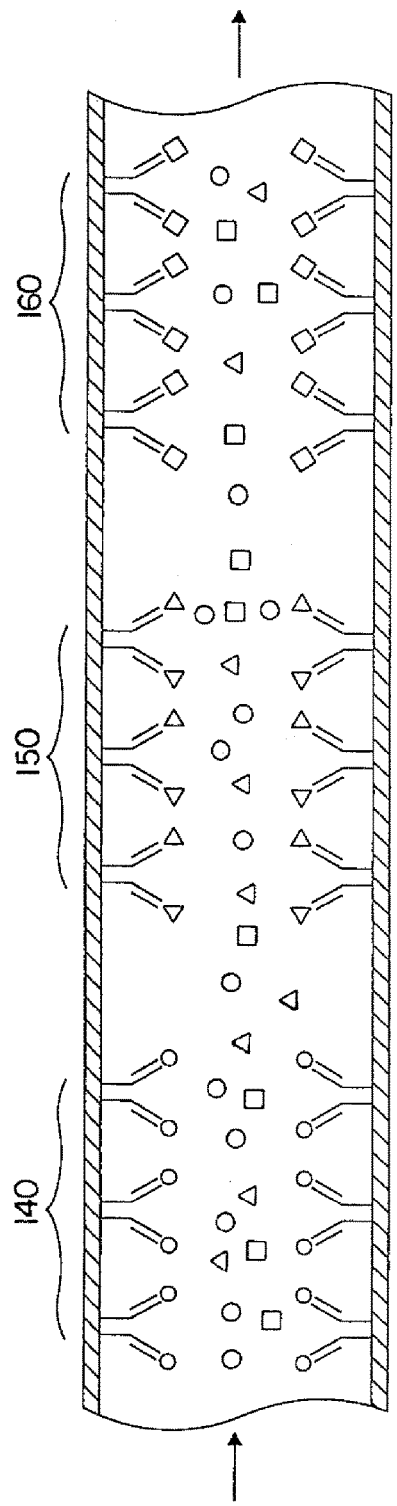
FIG. 23A illustrate an enlarge view of multiple antibodies along the interior surface of a separation capillary.
Figure 23B:
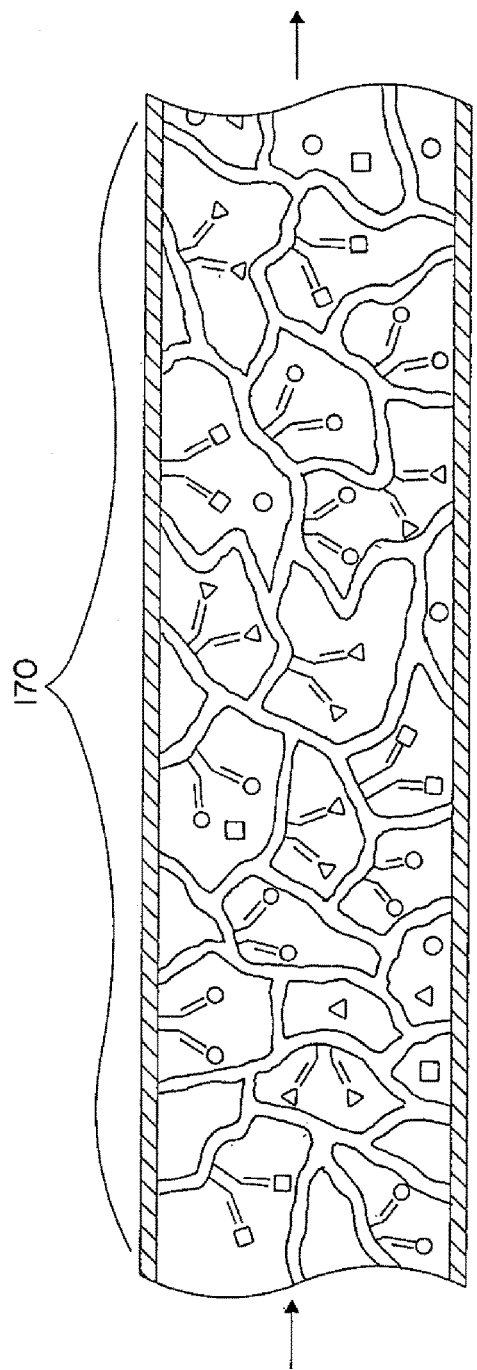
FIG. 23B illustrates polymeric microstructures with Y shape antibodies having affinity for a particular analyte within the concentrator area without the need for frits.

The antibody may be any type of affinity interacting chemical or biological system that attracts a particular analyte. FIGS. 23A and 23B illustrate an enlarge view of the antibodies 140, 150, and 160 along the interior surface of the separation capillary 28. Each antibody generally has a shape that is coupled to a substrate, which in this case is the interior surface of the separation capillary 28. The Y shape antibody includes two arms and one stem that imbeds into the substrate. As such, the antibody is immobile, but the two arms have affinity for a particular analyte (one in each arm) and as that analyte passes across the antibody, the two arms bond to the analyte until the eluting buffer solution interacts with the antibody to release the analyte. For example, in FIG. 23A, the two arms for the antibodies 140 have affinity for the circular analyte but not the square analytes or the triangular analytes. In contrast, the two branches for the antibodies 160 have affinity for the square analyte but not the circular analytes or the triangular analytes. Other antibodies in the separation capillaries 28, however, may have affinity for the triangular analytes and bond to the triangular analytes.

FIG. 23B illustrates polymeric microstructures with Y shape antibody having affinity for a particular analyte within the concentrator area without the need for frits. Each beaded microstructure may have an antibody that has affinity for a different analyte.

FIGS. 24A and 24B illustrate the use of an antibody like Fab' as described above. In contrast to the antibodies shown in FIGS. 23A and 23B, these Fab' antibodies have one side of the original antibody. The antibodies are attached to the substrate by a portion of the original stem, allowing each group of antibodies to retain their specificity, attracting and bonding to only one type of analyte.

Figure 26:
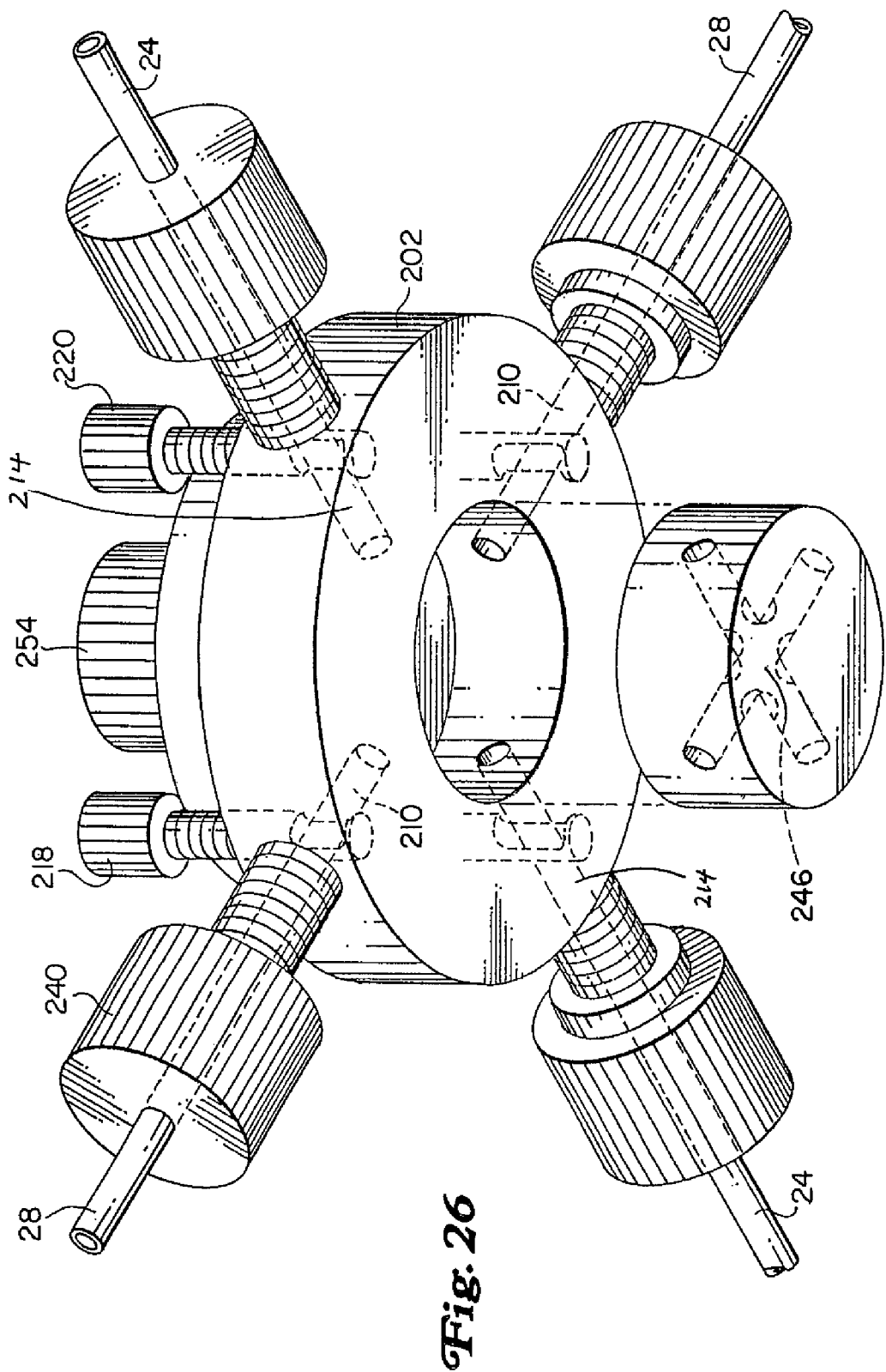
FIG. 26 is a perspective view of the bottom side of the microextraction device of FIG. 25, illustrating the concentration or reaction area.

FIGS. 25-27 illustrate a microextraction device 200 having four tubing-connecting ports: two ports 210 couple to the transport capillary 24, and two other ports 214 couple to separation capillary 28, for example. The two ports 210 for the transport capillary 24 may be larger than the two ports 214 for the separation capillary to accommodate the larger size opening in the transport capillary 24. Port 210 may be formed from fused-silica, port 214 may be formed from a plastic tube. As illustrated in FIG. 27A, the two ports 210 and 214 intersect to form a concentration area 246. The microextraction device 200 may also have a filling port 252 that provides access to the concentration area 246. The filling port 252 may be provided at the central part of the microextraction device 200. With the filing port 252, prepared by using controlled pore glass (CPG) beads having covalently attached antibody fragments to their surfaces may be inserted into the concentration area 246. This feature allows the coated beads to be replaced as the performance of the immobilized antibody fragments degrades after repeated usage.

The ports 210 and 214 may be formed within the base 202, and the filing port 252 may be formed on the cover 208. The base 202 may have openings 230, 232, 234, and 236 that pass through the corresponding ports 210 and 214. The openings 230, 232, 234, and 236 may be adapted to receive the elongated portion of valves 218, 220, 222, and 224 that are able to move between first and second positions. As illustrated in FIG. 25, each valve may have a protruding portion 226 with a cutout 228 to control the flow of fluid through the respective capillary. The cutout 228 may also be a hole found through the protruding portion 226. The hole may be coated with glass. To enable normal electrosmotic flow of liquid through the cutout 228, the cutout 228 may be formed from fused silica or coated with fused silica to maintain a closed connection with the fused-silica capillaries for the CPG beads.

The port 210 may be substantially aligned with the longitudinal direction of the separation capillary 28, and the port 214 may be substantially aligned with the longitudinal direction of the transport capillary 24. The port 214 may have a larger opening than the opening for the port 210 to allow greater flow rate of the sample solution from the transport capillary 24. Likewise, the transport capillary 24 may have a larger opening than the separation capillaries for greater flow rate.

As illustrated in FIG. 25, an indicating arrow 238 may be provided on the valve so that if the direction of the indicating arrow is in line with longitudinal axis of the capillary then the valve is in the first position, and if the direction of the indicating arrow is perpendicular to the longitudinal axis of the capillary then the valve is the second position. In the first position, the cut out 228 is aligned with the longitudinal direction of the port to allow the fluid to pass through the port. In the second position, however, the cut out 228 faces away from the port so that the protruding portion of the valve blocks the flow of fluid through the port. A connector 240 may be provided to couple the microextraction device 200 to the transport and separation capillaries. For instance, in FIG. 26, the connector 240 may be used to couple the capillary 28 to the port 210 so that the fluid from the capillary 28 may be passed to the port 210.

FIG. 26 illustrates a cut out view of the intersection area 246 formed by the intersection of the ports 210 and 214. This way, if the valves 218 and 222 are in the first position and the valves 220 and 224 are in the second position, the fluid from the capillary 28 may pass through the port 210, and then to the capillary 28 on the other end of the base 202 towards the detection device. Likewise, if the valves 220 and 224 are in the first position and the valves 218 and 220 are in the second position, the fluid from the capillary 24 may pass through the ports 214 and 216, and then to the transport capillary 24 on the other end of the base 202.

As further illustrated in FIG. 27A, the intersection area 246 may have bulging members 248 along the corners of the channels 210, 212, 214, and 216. FIG. 27B is an enlarged view of the intersection area 246 illustrated in FIG. 27A. The bulging members 248 along the ports provide for a restricted area in the area 246 such that the gaps through the ports in the intersection area are smaller than the size of the beads or matrix 250, thereby preventing the beads or matrix from moving out of the intersection area 246. As such, the beads or the matrix may capture the desired analytes as the sample passes through the intersection area 246.

Figure 28A:
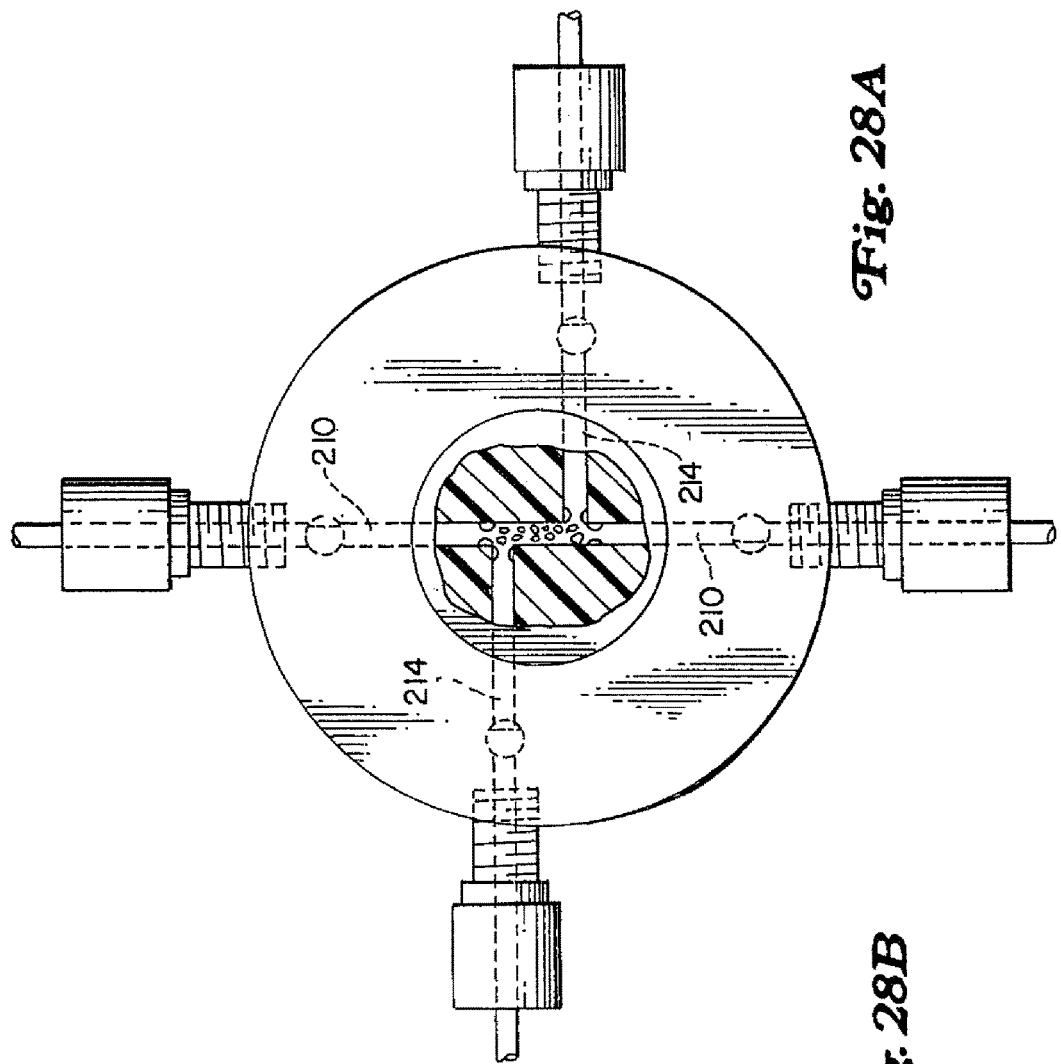
FIG. 28A illustrates a microextraction device with a concentration area that is elongated.
Figure 28B:
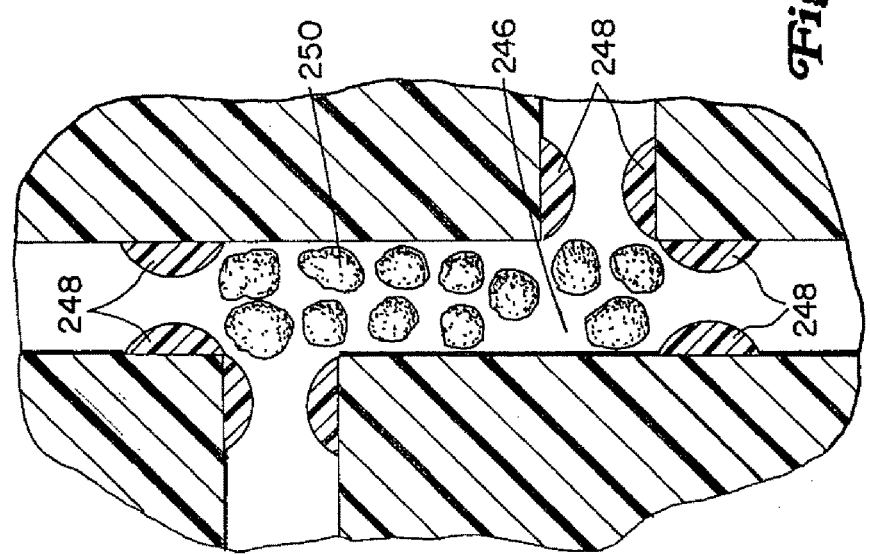
FIG. 28B illustrates an enlarge view of the concentration area of FIG. 28A.

As illustrated in FIGS. 28A and 28B, the port 210 that is aligned with the transport capillary may be staggered to form an elongated concentration area 246. This allows additional matrix-like assembly or beads 250 to be incorporated into the concentration area 246 to attract the desired analyte from the sample solution. In addition, the bulging members 248 may be provided near the intersection area 246 to contain the beads within the intersection area.

FIG. 25 illustrates that the cover 208 may have a filling port 252 adapted to receive a cap 254. The filling port 252 may be provided to insert the beads 250 or matrix into the intersection area 246 to capture the desired analytes. Once the beads 250 are inserted into the intersection area, the cap 254 may be used to enclose the filling port 252. Moreover, the beads 250 may be replaced through a variety of methods. For instance, the beads in the intersection area 246 may be removed by opening the cap 254 so that the beads are exposed through the filling port 252. The beads may then be removed through a vacuum source such as a syringe. Once the old beads are removed, a new set of beads with affinity for a desired analyte may be inserted to the intersection area 246 through the filling port 254. To secure the new beads within the intersection area, the cap 254 may enclose the filling port 252.

Experimental Data

The following is experimental data for the above invention. Where relevant, references are cited in the following discussion. A list of cited references is provided under the subheading "References" in this specification. For this experiment, a simple, solid-phase, microextraction device was fabricated for use in on-line, immunoaffinity capillary electrophoresis. The device, designed in the form of a four-part cross-shaped or cruciform configuration, included a large-bore tube to transport samples and washing buffers, and a small-bore fused-silica capillary for separation of analytes. At the intersection of the transport and separation tubes, a small cavity was fabricated, termed the analyte concentrator-microreactor, which contained four porous walls or semi-permeable membranes (one for each inlet and outlet of the tubes) permitting the confinement of beads or suitable microstructures. The surface of the beads in the analyte concentrator carried a molecular recognition adsorbing chemical or affinity ligands material. The improved cruciform configuration of the analyte concentrator-microreactor device, designed for use in on-line immunoaffinity capillary electrophoresis, enables it to specifically trap, enrich and elute an analyte from any biological fluid or tissue sample extract without any sample pretreatment except filtration, centrifugation, and/or dilution allowing the separation and characterization of target analyte(s) with improved speed, sensitivity, and lower cost than existing techniques.

As a model system, Fab' fragments derived from a purified IgG antibody were covalently bound to controlled-porosity glass and used as constituents of the analyte-microreactor device. The high-specificity polyclonal antibodies employed in these experiments were individually raised against the acidic non-steroidal anti-inflammatory drugs ibuprofen and naproxen, and the neuropeptides angiotensin II, and neurotensin. These compounds, which were present in simple and complex matrices were captured by and eluted from the analyte concentrator-microreactor using a 50 mM sodium tetraborate buffer solution, pH 9.0, followed by a 100-nL plug of 300 mM glycine buffer, pH 3.4, or preferentially a 100-nL plug of 10 mM phosphate-buffered saline, pH 7.4, containing 20-50% acetonitrile. Two analyte concentrators were tested independently: one containing Fab' fragments derived from antibodies raised against ibuprofen and naproxen; the other containing Fab' fragments derived from antibodies raised against angiotensin II and neurotensin. Each resulting electropherogram demonstrated the presence of two eluted materials in less than 20 min.

Immunoaffinity capillary electrophoresis performed in a cruciform structure was simpler and faster than previously reported in the literature using on-line microextraction devices designed in a linear format. The new concentration-separation system operated consistently for many runs, maintaining reproducible migration times and peak areas for every analyte studied.

This microextraction device design has been fabricated for facilitating the rapid introduction of samples and cleaning buffers through a large-bore transport tube, and for improving the determination of affinity-bound target analytes employing a small-bore separation capillary, maintained free of contamination, after multiple uses. The on-line extraction approach using immunoaffinity capillary electrophoresis is illustrated by determining the acidic drugs ibuprofen and naproxen, and the peptides angiotensin II and neurotensin in urine at concentration levels of less than 5 ng/mL, when the separated analytes were monitored at 214 nm. Furthermore, the microstructures within the cavity of the analyte concentrator-microreactor containing suitable immobilized antibodies were re-used several times, and when their performance diminished, it was possible to readily replace them with new ones.

Materials and Methods

Chemicals:

All chemicals were of the highest quality reagent grade. Deionized, double-distilled water was purified with a Milli-Q-Plus Ultra-Pure water system from Millipore Corporation (Bedford, Mass., USA). Nylon filters (0.20 µm) used to remove particulate matter were obtained from Gelman Sciences (Ann Arbor, Mich., USA). Underivatized controlled pore glass (CPG) beads (3000 Å pore size, 200-400 mesh, irregularly shaped) were purchased from CPG Inc. (Fairfield, N.J., USA). Bare fused-silica capillary columns were obtained from Polymicro Technologies (Phoenix, Ariz., USA). Sulfosuccinimidyl 4-(N-maleidomethyl)cyclohexane-1-carboxylate (SSMCC), the immunoPure F(ab')2 preparation kit, 2-mercaptoethylamine.HCl, Blue Carrier® immunogenic protein, and pepsin agarose were purchased from Pierce Biotechnology (Rockford, Ill., USA). 3-Aminopropyl-triethoxysilane was obtained from Polysciences (Warrington, Pa., USA). S-(+)-Ibuprofen ((S)-(+)-2-(4-isobutylphenyl)propionic acid), S-(+)-naproxen ((S)-(+)-2-(6-methoxy-2-naphthyl)propionic acid), phenylmethylsulfonyl fluoride, soybean trypsin inhibitor, iodoacetate, p-aminobenzamidine.HCL, leupeptin hydrochloride, potassium chloride, sodium phosphate ($Na_2PO_4$), and potassium phosphate ($KH_2PO_4$) were purchased from Sigma-Aldrich (St. Louis, Mo., USA). Peptide-N-glycosidase F (PNGase F) was obtained from New England Biolabs (Beverly, Mass., USA). Sodium thiocyanate and sodium azide were purchased from Fisher Scientific (Pittsburgh, Pa., USA). Superdex-75 resin, PD-10 desalting column, and r-Protein A Sepharose™ were purchased from Amersham Pharmacia Biotech (Piscataway, N.J., USA). Angiotensin II and neurotensin were obtained from Peninsula Laboratories (Belmont, Calif., USA) and Sigma-Aldrich. Methanol was purchased from Allied Signal, Burdick & Jackson (Muskegon, Mich., USA). Sep-Pak C18 cartridges were obtained from Waters Corporation (Milford, Mass., USA). A concentrated (10-fold) phosphate-buffered saline solution was prepared as follows: Dissolve 80 g of NaCl, 2.0 g of KCl, 14.4 g of $Na_2HPO_4$, and 2.4 g of $KH_2PO_4$ in 800 ml deionized, double-distilled water; adjust the pH to 7.40 with HCl; adjust the volume to 1 liter with additional deionized, double-distilled water; filtered with Nylon filters (0.20 µm). The final concentration of the used phosphate-buffered saline (a 1:10 dilution from the concentrated) is approximately the following: 0.010 M sodium phosphate (dibasic) buffer, pH 7.40, containing 0.0027 M potassium chloride, 0.137 M sodium chloride, and 0.0018 M potassium phosphate (monobasic).

Fresh, stock solutions of the peptides dissolved in water at a concentration of 100 µg/mL were prepared prior to use. The acidic drugs ibuprofen and naproxen were dissolved in a methanolic solution (35:65 methanol:water, v/v), also at a concentration of 100 µg/mL.

Methods:

Preparation of Urine Samples.

Urine samples from healthy males were collected as morning clean-catch urine specimens, prior to breakfast and with a simple dinner the previous evening. Immediately after collection of a pool of six urine samples, a cocktail of protease inhibitors was added including 0.1 mM of PMSF, soybean trypsin inhibitor, iodoacetate, p-aminobenzamidine, and 1 mM leupeptin [1,2,3]. A 0.20-µm porous diameter Nylon filter was used to filter the pooled samples, to remove particulate matter or cells. Diluted and undiluted urine samples were used for the experiments. Undiluted urine specimens were spiked with the analytes prior to On-line, immunoaffinity capillary electrophoresis (IACE) by adding the two acidic drugs into one aliquot of urine sample, and the two peptides into a second aliquot of urine sample, with final concentrations of 1-, 2-, 5-, and 50-ng/mL respectively. Conversely, urine samples were diluted first (1:1 and 1:5, v/v) with 50 mM sodium tetraborate buffer, pH 9.0, and then spiked with the analytes, as described above, at the same final concentrations as the undiluted samples.

Preparation of Antibodies.

Figures 29A, 29B:
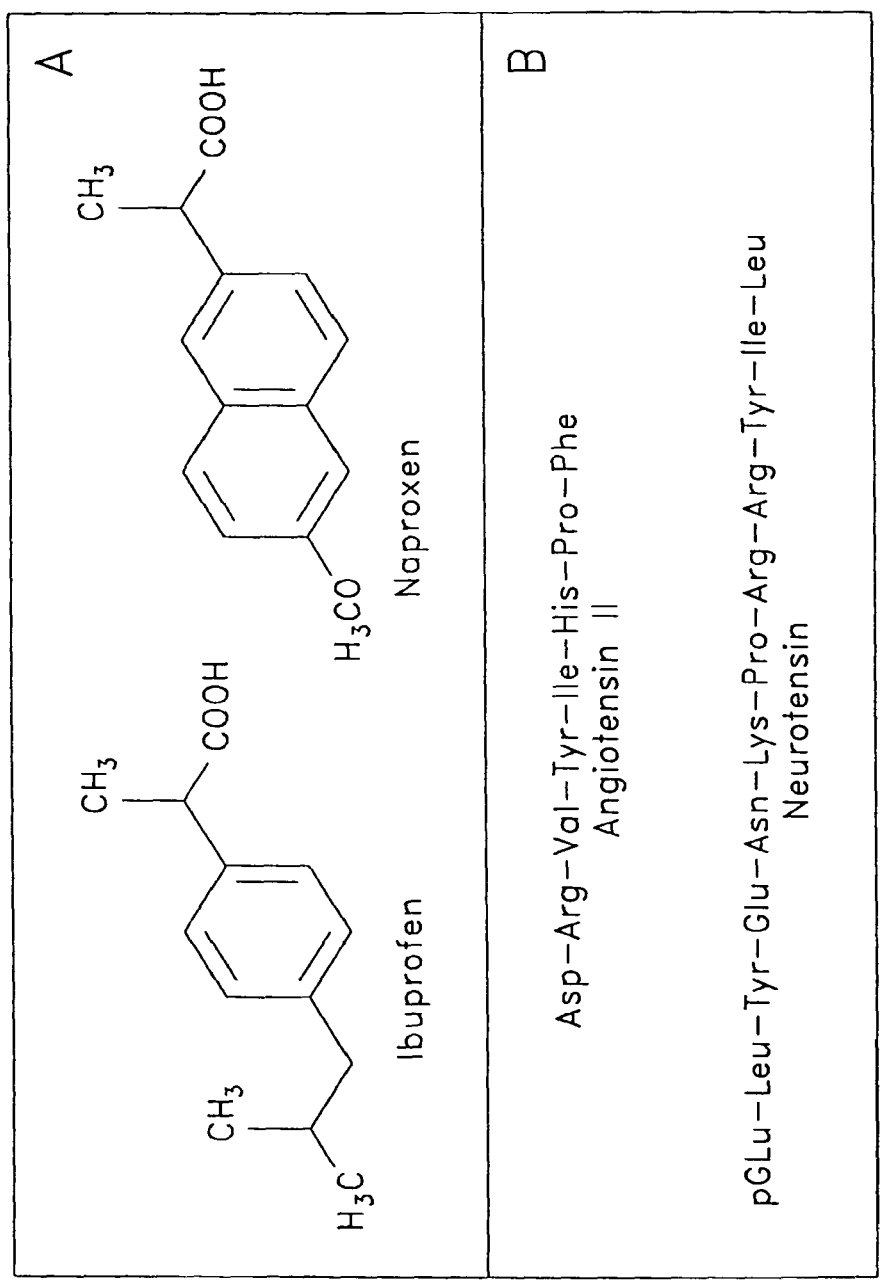
FIG. 29A illustrates molecular structure of acidic drugs, ibuprofen, and naproxen.
FIG. 29B illustrates molecular structure of neuropeptides, angiotensin II, and neurotensin.

Polyclonal antibodies raised against commercially available ibuprofen, naproxen, angiotensin II, and neurotensin (FIGS. 29A and 29B), coupled covalently to Blue Carrier immunogenic protein, were raised in rabbits using a method similar to those described elsewhere [3,4]. The purification of the antibodies from rabbit antisera was performed by HPLC using r-Protein A affinity chromatography as previously described [4]. Conjugates for immunization were prepared by various methods with the same modifications [1,5-7]. The method described by Grafe and Hoffmann [5] was used to link ibuprofen to the Blue Carrier immunogenic protein. The method described by Shi et al. [6] was used to link naprofen to the immunogenic protein. The linking of the peptides to the immunogenic protein was performed as previously reported for other carriers [1,7].

The antibodies purified from the antisera by r-Protein A Sepharose affinity chromatography, were further purified by immunoadsorption on a CPG column containing immobilized haptens (ibuprofen, naproxen, angiotensin II, or neurotensin). In order to accomplish this task, the haptens ibuprofen and naproxen were covalently linked to controlled-porous glass, employing the same chemistries used to link the haptens to the Blue Carrier immunogenic protein. The peptides were linked to CPG through a procedure described elsewhere [7]. The columns were individually eluted with 3 M sodium thiocyanate in 0.01 M sodium phosphate buffer pH 7.0 [3]. The highly specific, pure antibodies were dialyzed against 0.01 M sodium phosphate buffer pH 7.0, aliquoted in small fractions, and stored at −70° C. until use.

Preparation of Monovalent Fab' Fragments

Immunoadsorbed purified antibodies were subjected to two partial enzymatic digestions to generate $F(ab')_2$ antibody fragments. The first digestion, a deglycosylation process described by Wilson et al. [8], was performed to remove N-linked glycosyl groups attached to the Fc fragment of IgG. These investigators used PNGase F, an enzyme that removes N-linked oligosaccharides. Approximately 20 U/µL PNGase F were incubated with 1 mg/mL of purified IgG for 24 hr at 37° C. (FIG. 20).

The second enzymatic digestion was carried out using pepsin to remove the Fc fragment of the IgG while maintaining the intra- and inter-disulfide bridges. This enzymatic process was readily achieved, since the Fc fragment was free of sugars. The removal of some steric hindrance from neighboring carbohydrate moieties near the hinge region facilitated the action of pepsin. Pepsinolysis was carried out using a combination of the method described by Wilson et al. [8], and the manufacturer's instructions described in the ImmunoPure $F(ab')_2$ preparation. The divalent $F(ab')_2$ antibody fragments formed were then reduced to monovalent Fab' antibody fragments, by incubation with equal volumes of 200 mM mercaptoethylamine.HCl reagent for 30 min at 37° C. This step, reported by Phillips and Smith [2], replaced the $F(ab')_2$ reduction with Cleland's reagent (as previously described) because the latter agent was found to require optimization conditions and it is or can be an unpredictable reducing agent (FIG. 16).

Coupling of Fab' Fragments to Glass Beads

Controlled-porous glass beads, previously utilized to link antibodies directed against methamphetamine[7,9], were employed to bind monovalent Fab' fragments purified from antibodies raised against the two acidic drugs and the two neuropeptides [9,10,1,7,11]. The irregularly shaped beads were incubated at 95° C. for 60 min in the presence of 10% aqueous 3-aminopropyltriethoxysilane. This treatment was repeated four times. The incubation was carried out with the beads and solution inside a double side arm glass container, in a temperature-controlled water bath, with gentle agitation. The access ports of the glass container, inlet and outlet, were sealed with multi-hole plastic caps to reduce the evaporation of the silane solution. The beads were then incubated at 95° C. for 60 min with 10 mM hydrochloric acid. The beads were washed with copious amounts of distilled/deionized water before preparing the maleimide-activated surface. The beads were then incubated at 30° C. for 60 min with a buffer solution containing 50 mM sodium borate, pH 7.6, and 1 mg/mL SSMCC. The beads were finally washed thoroughly with 50 mM sodium borate buffer, pH 7.6, and then incubated overnight at 4° C. with approximately 500 µg/mL of SH-containing Fab' peptide in 50 mM sodium borate buffer, pH 7.6. The entire process to link SH-containing Fab' fragments to the wall of the capillary is summarized in FIG. 21.

Fabrication of the Analyte Concentrator-Microreactor

The analyte concentrator-microreactor device, designed in a cruciform configuration with four entrance-exit ports (FIG. 11A), was made of a transparent acrylic substrate, but other plastic materials (e.g., Teflon®, nylon, polyimide, or PEEK) may also be used. Two chromatographic fittings were used to connect two large-bore plastic tubes (one inlet, one outlet) to the microextraction device to transport sample and washing buffers. Two nanovolume fittings (nomenclature used to describe a device or sleeve to provide a tight fitting to a fused-silica capillary) were used to connect two 100-µm i.d., 360-µm o.d. fused-silica capillaries (one short inlet, one long outlet) to the device (FIGS. 25-27). Each port contained a porous polymeric frit, or a constricted area, fabricated from fine pieces of material produced by a blade from a frit taken from a commercially available Sep-Pak C18 cartridge. The semi-permeable frit structure permitted the confinement of the irregularly shaped CPG beads containing immobilized Fab' fragments of IgG within the analyte concentrator-microreactor. The cavity was filled with CPG beads through an additional port (termed the filling port) after the appropriate tubing (two PEEK tubes and two fused-silica capillary tubes) at the four ports were previously installed. After the cavity was properly filled with the coated beads employing a low vacuum aspiration system and gentle shaking of the device, the filling port that facilitated the entrance of the beads into the system was closed very tightly to prevent air from entering the analyte concentrator-microreactor. Since the analyte concentrator-microreactor device was made of a transparent acrylic substrate, the entire packing process was monitored using a stereo microscope.

The solid-phase microextraction device was designed with four microvalves as indicated by circles with cross areas in FIG. 11A and in more detail in FIGS. 25-27. The micro-fabricated valves permitted full control of the path of fluid in the appropriate direction, allowing the interaction of the constituents of the sample under study with the antibody fragments present in the analyte concentrator-microreactor device.

Figure 30:
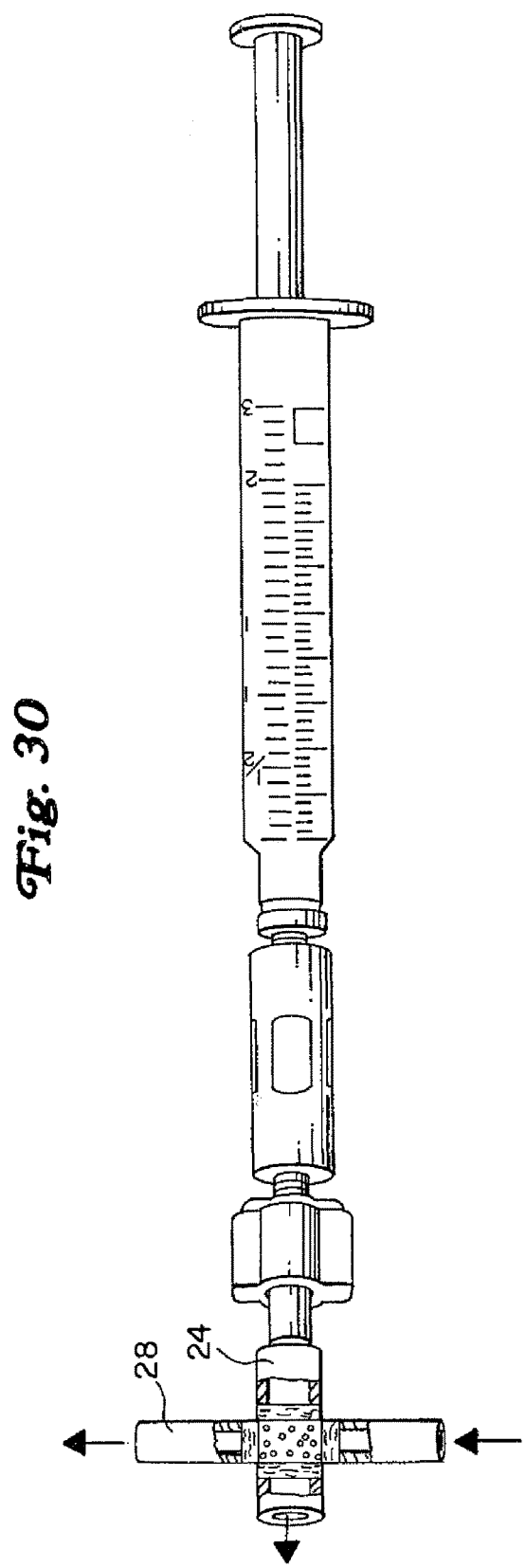
FIG. 30 illustrates a syringe coupled to a transport tubing.
Figure 31:
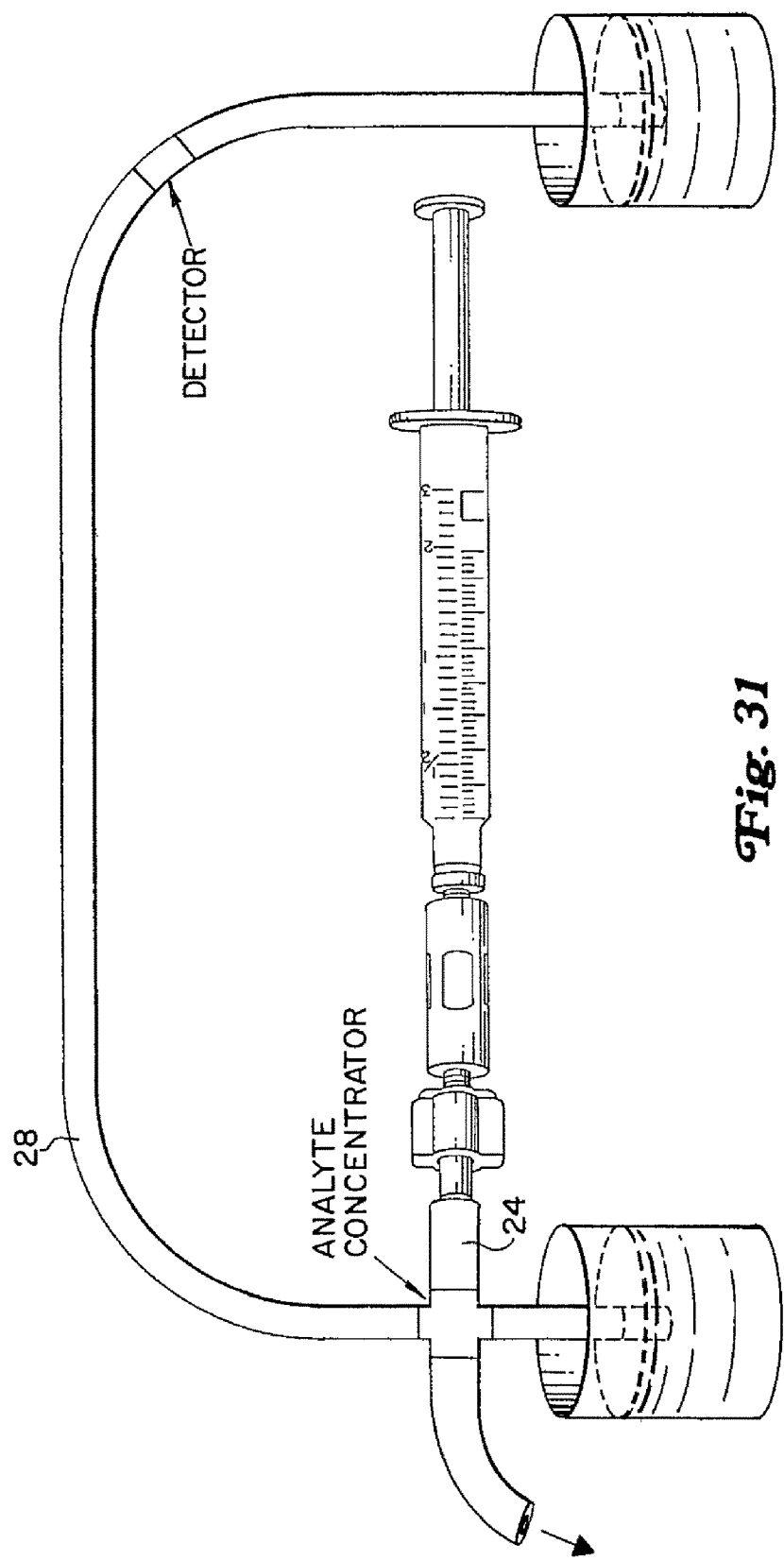
FIG. 31 illustrates a capillary electrophoresis having a concentrator near the inlet of the transport capillary.

Once the analyte concentrator-microreactor was completed packed and properly assembled, one of the inlet positions for the large-bore tubing was attached by a commercially available connector to a 3-mL plastic syringe as depicted in FIGS. 30 and 31.

Separation and Detection of Analytes by CE-UV

Capillary electrophoresis studies for ibuprofen and naproxen [12], and angiotensin II and neurotensin [13,14] have been reported previously using commercially available instruments, but not using the cross-shaped analyte concentrator-microreactor configuration. For experiments directed to this application, a capillary electrophoresis apparatus as depicted in FIG. 31 was employed [4,14]. The fused-silica capillary (100-µm×65-cm×100-cm) used for analyte separation was conditioned prior to being connected to the microextraction device, by rinsing with water for 2 min, 0.5 N NaOH for 5 min, water for 3 min, and with background electrolyte (as specified below) for 5 min. The introduction of sample and washing buffer was achieved by using the appropriate valves to direct the flow of liquid (FIGS. 11A and 25-27). When the valves for the transport tube were closed, the separation capillary was conditioned with 50 mM sodium tetraborate, pH 8.5. When the valves for the separation capillary were closed, samples were introduced into the analyte concentrator-microreactor using a large-bore plastic tube by positive pressure using a syringe, or by employing a low vacuum aspiration system directly from the sample reservoir. The amount of sample introduced into the microextraction device was approximately 1 mL, a sufficient volume containing enough concentration of hapten to saturate the binding sites of the antibody fragments. Standards were prepared in 50 mM sodium tetraborate buffer, pH 9.0. Spiked urine samples were prepared by adding the analytes directly to undiluted urine, or to diluted urine in 50 mM sodium tetraborate buffer, pH 9.0. The sample was allowed to be in direct contact with the immobilized affinity ligand for 5 min, permitting the peptide to be retained in order to control the appropriate interaction and temperature for achieving maximum binding. After a few washes of the transport tube with 50 mM sodium tetraborate buffer, pH 9.0, the valves were switched to the separation position. The separation column was conditioned once more with 50 mM sodium tetraborate buffer pH 8.5, and completely degassed. The peptide was finally eluted with a plug of approximately 100 nL of 300 mM glycine-HCl buffer, pH 3.4, or preferentially 100 nL of 10 mM phosphate-buffered saline, pH 7.4, containing 20-50% (v/v) acetonitrile, and the separation was allowed to continue. (The glycine buffer is used normally when the peptides are labeled with a fluorescence chromophore, and fluorescence detection is employed. The phosphate-buffered saline, containing acetonitrile or other organic solvent, is normally used when the peptides are not tagged by a fluorescence chromophore, and ultraviolet detection is employed.)

All separations were performed at 26 kV, and the majority of the capillary was positioned within a cartridge cassette [15,4,14], containing a fluid of regulated-temperature, in order to maintain the capillary temperature at approximately 25° C. The separated analytes were monitored by UV-absorption preferentially at 214 nm (but a wide range of wavelengths can be used as well), using a modified on-column UV, variable-wavelength detection system (Hitachi Instruments, Inc., Danbury, Conn., USA). Data collection for quantification of the electropherographic peaks was carried out with a Chromato-Integrator (Hitachi Instruments, Inc.).

When not in use, all separation capillaries were removed from the microextraction device and rinsed with sequential washes of water, 0.1 N NaOH, water, 0.5 N HCl, and water for approximately 5 min each, and then stored in air at 25° C. The area of the microextraction device was maintained wet at all times with a solution of 50 mM sodium tetraborate buffer, pH 7.0, containing 1% (w/v) sodium azide. The microfabricated valves were kept closed to allow the tetraborate-azide buffer to remain within the microextraction device. The disassembled microextration device was stored at 4° C.

Results and Discussion.

Improved Procedure to Obtain Fab' Fragments. (FIG. 20.)

One of the standard procedures to obtain Fab' fragments containing the hinge region cysteine(s) is to generate first F(ab')$_2$ fragments. Traditionally, pepsin has been the preferred proteolytic enzyme to cleave the Fc fragment of several IgGs, including IgY [56], when compared to bromelain, ficin, and lysyl endopeptidase [16,17]. However, a wide range of optimization conditions for the cleavage of the Fc fragment constituent of the monomeric IgG, have been reported in the literature [17-20]. Apparently, the different subclasses of IgGs present a certain degree of resistance to pepsin cleavage producing a wide variation in the yield for the formation of F(ab')$_2$ fragments, depending of the IgG subclass. This is due, in part, by investigators who underestimated the steric effect on the active site of pepsin, which can be attributed to the presence of N-linked carbohydrates near the hinge of IgG. Wilson et al. [8], demonstrated that by removing the carbohydrate groups of the intact IgG molecule, prior to digestion by pepsin, the yield for the formation of F(ab')$_2$ fragments increased dramatically. The presence of carbohydrates in antibodies seems to be important for antigen clearance functions, such as complement activation, and antibody activity [21]

In the experiments reported here, it was confirmed that the removal of N-linked carbohydrates was preferred for facilitating pepsin activity on the IgG molecule, to generate dimeric F(ab')$_2$ fragments and then monomeric Fab' fragments (see FIG. 20). Comparative pepsinolysis studies of IgG, with and without glycosylation, demonstrated a more consistent yield of the monomeric deglycosylated IgG when qualitative and quantitative capillary electrophoresis studies were performed (data not shown). Covalent attachment of monomeric Fab' fragments through SH— groups permits proper orientation of the molecule and increases the surface area to enhance the capturing of a target ligand. Specifically oriented attachments of antibodies, or antibody fragments, to a surface have been demonstrated to be more efficient in capturing a target analyte, when compared to chemistries employing random attachments [22-24]. The advantages of oriented immobilization of biologically active proteins are: (a) improved steric accessibility to the active binding sites; (b) increased stability of the immobilized molecule; and (c) facilitation to a greater surface area of affinity interaction.

Determination of Pharmaceutical Drugs and Peptides in Urine Specimens

Determination of non-steroidal anti-inflammatory drugs and neuropeptides in urine was carried out by immunoaffinity capillary electrophoresis. Several experiments were performed to test the efficiency of the system. In a preliminary study, a 50-ng/mL solution of angiotensin II was applied to the analyte concentrator-microreactor device containing immobilized Fab' fragments derived from a polyclonal antibody raised against the peptide. The device was part of the capillary electrophoresis instrument depicted in FIG. 31. The sample was allowed to be in direct contact with the immobilized affinity ligand, the peptide was retained, and after a few washes and conditioning with the appropriate buffers, the peptide was eluted with a small plug of 0.3 M glycine-HCl buffer, pH 3.4, or neutral pH buffers containing acetonitrile, such as phosphate-buffered saline, pH 7.4, containing 20-50% acetonitrile, or other organic solvents at concentrations ranging from 5% to 100% (apparently, there is not a universal way of eluting all antibodies or antibody fragments. It is preferred to optimize every elution condition for each individual immobilized affinity ligand-target analyte complex. Since the affinity binding is different for every immunological complex, it may affect the linearity of quantification if the hapten is not released completely from the immunological complex). The success of this experiment prompted optimization of the binding conditions. A series of dilutions were performed in the urine specimen, and spiked with the acidic drugs or peptides. A representative electropherogram is shown in FIGS. 32A and 32B. The urine specimen used in this experiment was diluted 1:1 (v/v) with 50 mM sodium tetraborate buffer, pH 9.0. The sample was divided in two aliquots. One aliquot was spiked with 5 ng/mL each of ibuprofen and naproxen, and another with 5 ng/mL each of angiotensin II and neurotensin. The samples were analyzed in two separate analyte concentrator-microreactors. The data obtained was consistent for 9 runs, maintaining reproducible migration times and peak areas as indicated in Table 1 below.

TABLE 1

Optimizing experimental conditions for enhancement of hapten-antibody binding.

| Sample | Ibuprofen | Naproxen | Angiotensin II | Neurotensin |
|---|---|---|---|---|
| Control sample (5 ng/mL) (dilution 1:1) | 14.40* 1845+ | 17.20* 1470+ | 13.30* 955+ | 16.40* 1580+ |
| Same as control (Assay No. 9) | 14.47* 1837+ | 17.25* 1463+ | 13.35* 950+ | 16.44* 1568+ |
| Same as control (after 3 months at 40° C. and with azide) | 14.50* 1657+ | 17.31* 1324+ | 13.39* 848+ | 16.48* 1417+ |
| Same as control (dilution 1:5) | 14.48* 1893+ | 17.26* 1486+ | 13.34* 975+ | 16.45* 1598+ |
| Sample at 2 ng/mL (dilution 1:1) | 14.46* 718+ | 17.28* 564+ | 13.37* 385+ | 16.47* 637+ |
| Sample at 1 ng/mL (dilution at 1:1) | 14.43* 293+ | 17.24* 185+ | 13.35* 193+ | 16.44* 321+ |
| Sample at 5 ng/mL (undiluted) | 14.38* 1417+ | 17.12* 1215+ | 13.17* 821+ | 16.34* 1411+ |
| Sample at 1 ng/mL (undiluted) | 14.36* 248+ | 17.09* 163+ | 13.11* 185+ | 16.29* 314+ |

Note

TABLE 1-continued

Optimizing experimental conditions for enhancement of hapten-antibody binding.

| Sample | Ibuprofen | Naproxen | Angiotensin II | Neurotensin |
|---|---|---|---|---| that the numbers with (*) represent migration time in minutes; and numbers with (†) represent peak area in arbitrary units.

The analyte concentrator-microreactor needs to be packed correctly. Otherwise, incorrectly filling of the device can lead to discontinuity in the current. The filled device was examined with the assistance of a stereo microscope to monitor packing efficiency. After three months at 4° C. and in the presence of sodium azide, the binding activity for most antibody fragments was still maintained at approximately 90% activity (Table 1).

Maintaining the appropriate pH was also useful, as demonstrated in the comparative studies performed for the diluted and undiluted urine specimens. As seen in Table 1, undiluted urines yield peak areas much lower than diluted urines, while giving very similar migration times. It has been known for many years, specificity is the ability of antibodies to discriminate among different ligands. In the case of haptens, extremely fine structural changes in the molecule are responsible for the discrimination [25]. To maintain the so called 'exquisite specificity', the molecular recognition properties needs to be kept at optimum conditions to be effective. Ionic strength and pH of the buffer is another factor in maximizing the binding. Since urine samples have different pHs, which is dependent on many factors, it would be appropriate to bring the pH of each urine tested to a value of 9.0, but this may be impractical. A dilution of 1:1 (v/v) with 50 mM sodium tetraborate buffer seems to be much more convenient and consistent with the needs of an automated system.

Higher dilutions of urine specimens, e.g., 1:5 (v/v), with 50 mM sodium tetraborate buffer, pH 9.0, provides improved replicates for peak areas when compared to the 1:1 dilutions, and thus confirms the importance of pH. The improved analyte concentrator-microreactor structure described in this paper has the following attractive features: (a) it uses microliter sample volumes; (b) extensive sample preparation is not required, except filtration, centrifugation, and/or dilution; (c) protects the separation capillary from non-specific binding of unwanted materials, because of its cruciform design; (d) operates consistently for many runs; (e) yields reproducible migration times and peak areas for the analyte under study; (f) permits easy replacement of CPG beads; (g) allows the on-line concentration of samples to increase up to 1000-fold or more, thereby permitting quantitation levels of analytes at approximately 5 ng/mL or lower using UV detection.

Figures 33A, 33B, 33C:
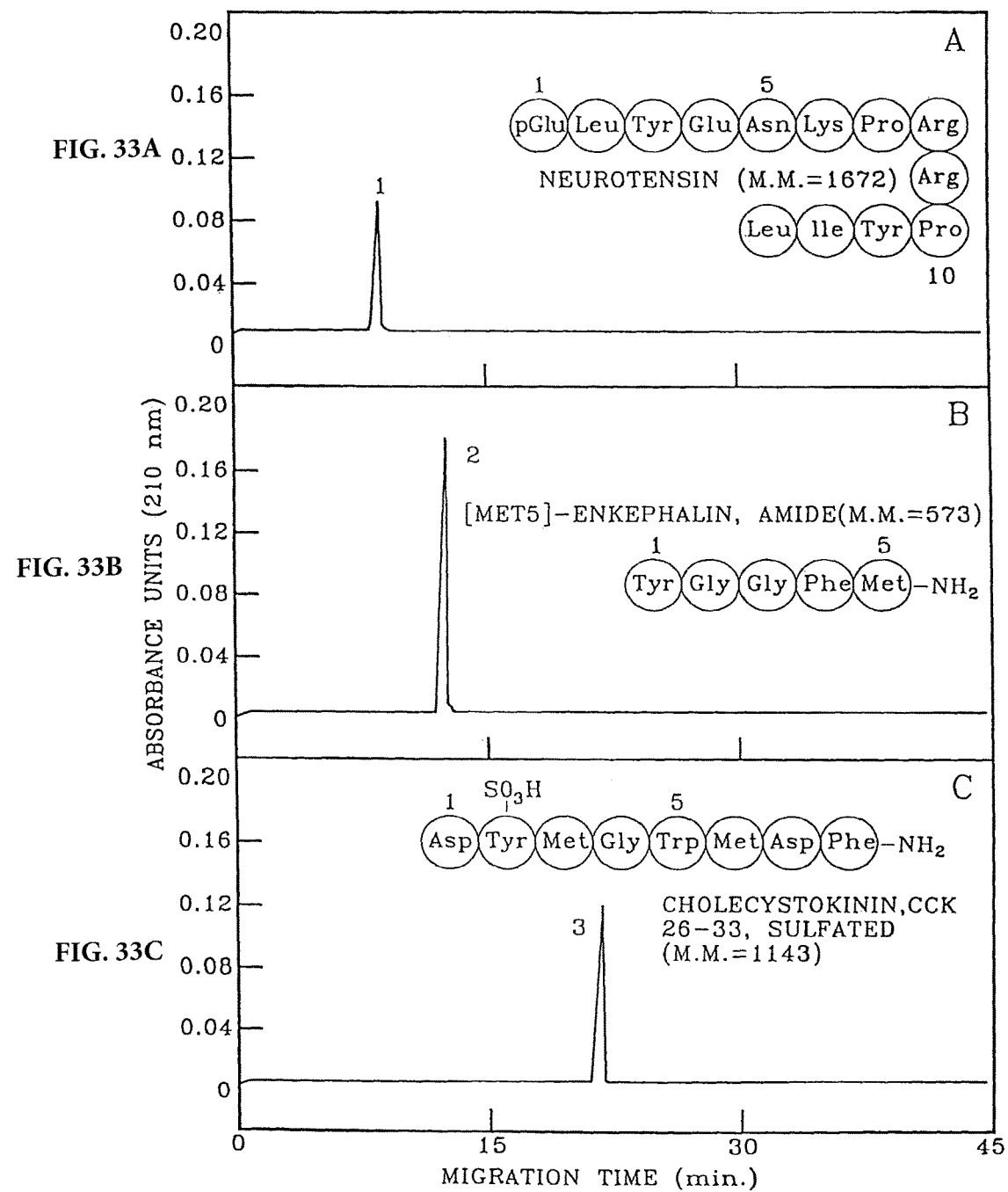
FIGS. 33A, 33B, and 33C illustrate electropherogram for analytes detected using the electrophoresis apparatus 10 with three concentrators with a different antibody in each of the concentrators, which acts against: (A) neurotensin; (B) enkephalin; and (C) cholecystokinin.

FIGS. 33A, 33B, and 33C illustrate electropherogram for analytes detected using the electrophoresis apparatus 10 with three concentrators with a different antibody in each of the concentrators. In this case, three antibodies of Fab' fragments which act against the following peptide hormones were used: (A) neurotensin; (B) enkephalin; and (C) cholecytokinin. The concentrators 34, 36, and 38, each had an antibody with affinity towards (A) neurotensin; (B) enkephalin; and (C) cholecytokinin, respectively. Urine specimen were spiked with the neurotensin, enkephalin, and cholecytokinin analytes prior to IACE. The urine specimen were then pass through the transport capillary 24 towards the three concentrators 34, 36, and 38. After the three antibodies captured their respective analytes, the separation capillaries 28, 30, and 32 were eluted sequentially. FIG. 33 indicates that migration time and peak for the three analytes: (A) neurotensin; (B) enkephalin; and (C) cholecytokinin correspond the control sample illustrating that the electrophoresis apparatus 10 operates consistently for the analytes under study. The process of capturing each peptide from the urine specimen by immobilized antibody fragments located at the analyte concentrator, cleaning the capillary with an appropriate buffer, eluting the bound peptide from the immobilized affinity ligand, and separating the released peptide by capillary electrophoresis was carried under the same experimental conditions as described above in the Experimental Data.

Figure 34:
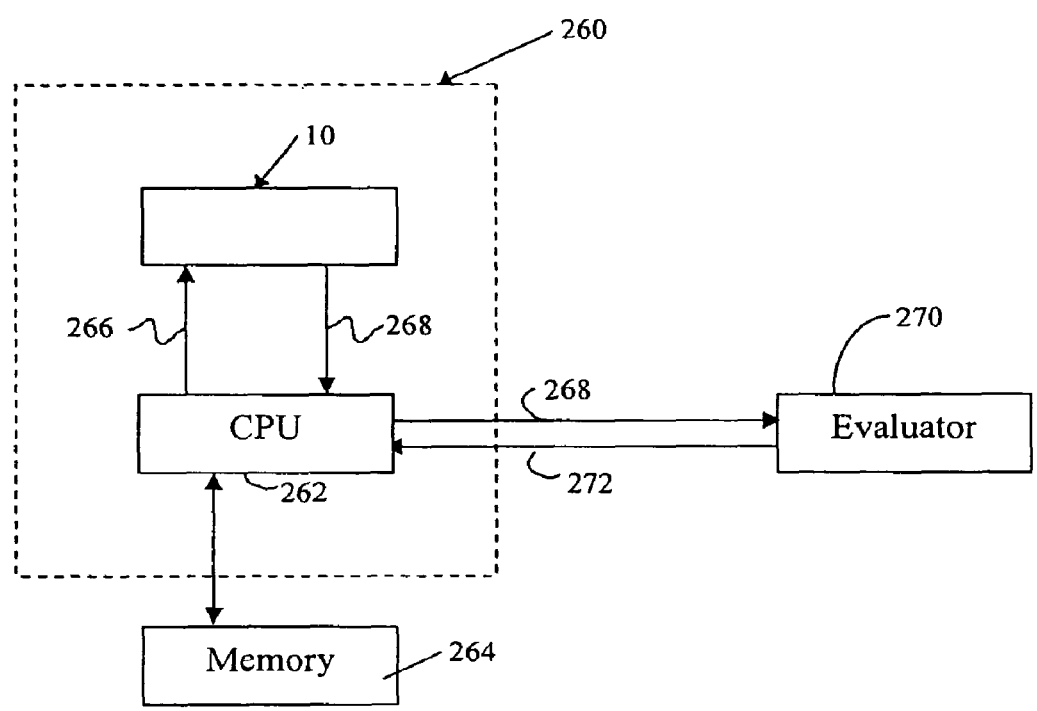
FIG. 34 illustrates a diagnostic kit that may be used at home by individuals to detect early signs of certain disease (s).

FIG. 34 illustrates a diagnostic kit 260 that may be used by individuals to detect early signs of certain disease(s). Some individuals may be predisposed to certain diseases more so than others based on their family health history, such as cancer, diabetes, and heart diseases. For these individuals, an early detection of such diseases may be a key to fighting the diseases. In this regard, individuals may use the diagnostic kit 260 to monitor and detect early signs of a number of diseases. Such tests may be done at the home of the individual for convenience and privacy. The diagnostic kit 260 may include the electrophoresis apparatus 10 that is communicateably coupled to a CPU 262 that may operate the electrophoresis apparatus 10 based on a predetermined set of instructions. As discussed above, the valves on the transport and separation capillaries may be motor operated, which are controlled by the CPU.

An individual that is predisposed to a predetermine disease may select or purchase a system of capillaries and valves with the concentrators 34, 36, and 38 that may isolate biomarkers that are associated with a predetermined disease. In general, each disease may have a plurality of biomarkers or analytes associated with that disease. A different disease may have different biomarkers than other diseases. As such, biomarkers may serve as a fingerprint for identifying a particular disease an individual may have based on test performed on the individual's specimen. If the biomarkers are detected, then evaluation may be made as to whether the biomarkers correspond to a particular disease or not. For instance, Disease 1 may be associated with four biomarkers: A, K, M, and T; Disease 2 may be associated with five biomarkers: B, D, F, L, and P; and Disease 3 may be associated with three biomarkers: B, T, and Y. Each biomarker may have its migration time through the separation capillary and peak that may be detected by the detector 86. If an individual is predisposed or concern about the disease 2, then the individual may select a system of capillaries and valves with at least five analyte concentrators where each analyte concentrator has an affinity towards the analytes or biomarkers B, D, F, L, and P, respectively, or in any order. In the case of detecting disease 3 with three biomarkers, concentrators 34, 36, and 38 as illustrated in FIG. 9 or FIG. 14 may be used to isolate biomarkers B, T, and Y, respectively. Alternatively, as illustrated in FIG. 22, a separation capillary 28 having three types of antibodies 140, 150, and 160 within its interior wall between the valves 104 and 108 may be used to isolate the biomarkers B, T, and Y, in any order. Likewise, the separation capillaries 30 and 32 may be used to isolate biomarkers A, K, M, and T for the disease 1, and biomarkers B, D, F, L, and P for the disease 2, respectively. As such, one system of capillaries and valves may be used to isolate biomarkers for more than one disease.

The individual may install the system of capillaries and valves into the platform 12 and locked it in placed with the holders 49. For isolating the biomarkers, the individual's specimen such as urine may be provided into the sample cup 15. Other specimen such as blood, hair, and nail may be provided. The CPU may then send the control signals 266 to operate the apparatus 10 according to the steps generally discussed in FIG. 12 to isolate the analytes of interest or the biomarkers from the specimen provided by the individual. The detector 86 may then obtain the data for each of the biomarkers in terms of their respective migration time and peak. For instance, if the individual providing the specimen does have the disease 3, then the detector 86 may find three biomarkers B, T, and Y, each having its respective migration time through the separation capillary and peak. On the other hand, if the individual does not have the disease 3, then one or two of the biomarkers may be detected from the specimen but not all three biomarkers. This data information 268 may be analyzed in a variety of ways. For instance, the data information 268 may be provided to the CPU 262, which is then compared with the plurality of reference data stored in the memory 264. The CPU may find that the biomarkers do indicate that the specimen provided by the individual has the disease 2 if all three biomarkers are found to have substantially similar respective migration time and peak as compared to the migration time and peak indicated in the reference data stored in the memory 264. On the other hand, if at least one of the biomarkers do not substantially match up with the migration time and the peak, then the CPU may indicate that the individual may not have the disease 2.

To check on the test result from the CPU, the individual may send the data 268 to an evaluator 270 such as a specialist or doctor to examine the data to confirm or deny that the biomarkers correspond to a disease. The evaluator may provide a feedback 272 to the CPU 262 so that the individual may take the next step based on the feedback provided by the evaluator. The memory may be updated by the evaluator if new biomarkers are found that corresponds to a particular disease. In addition, the evaluator 270 and the memory 264 may be provided remotely and the data 268 and feedback 272 may be provided electronically such as through the Internet. Alternatively, the CPU 262 may send the data information 268 directly to the evaluator 270 for analysis of the data and a feedback to the CPU. In other words, the CPU may skip the comparison of the data 268 with the reference data stored in the memory 264 and go directly to the evaluator 270 for the analysis.

All patents, patent publications, and other published references mentioned herein are hereby incorporated by reference in their entireties as if each had been individually and specifically incorporated by reference herein. By their citation of various references in this document, the applicant do not admit that any particular reference is "prior art" to his invention. While specific examples have been provided, the above description is illustrative and not restrictive. Any one or more of the features and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with the reference to the above description, but instead should be determined with reference to the appended claims along with their full scope of equivalents.

LIST OF REFERENCES

[1] Guzman, N. A., J. Chromatogr. B 2000, 749, 197-213.

[2] Phillips, T. M., Smith, P., Biomed. Chromatogr. 2003, 17, 182-187.

[3] Guzman, N. A., Ascari, W. Q., Cutroneo, K. R., Desnick, R. J., J. Cell. Biochem. 1992, 48, 172-189.

[4] Guzman, N. A., Hernandez, L., In: Techniques in Protein Chemistry, Hugli, T. E. (Ed.), Academic Press, New York, Chapter 44, pp. 456-467 (1989).

[5] Grafe, K. A., Hoffmann, H., Pharmazie 2000, 55, 286-292.

[6] Shi, Z.-D., Yang, B.-H., Zhao, J.-J., Wu, Y.-L., Ji, Y.-Y., Yeh, M. Bioorg. Med. Chem. 2002, 10, 2171-2175.

[7] Guzman, N. A., Trebilcock, M. A., Advis, J. P. J. Liq. Chromatogr. 1991, 14, 997-1015.

[8] Wilson, D. S., Wu, J., Peluso, P., Nock, S., J. Immunol. Meth. 2002, 260, 29-36.

[9] Guzman, N. A., Park, S. S., Schaufelberger, D., Hernandez, L., Paez, X., Rada, P., Tomlinson, A. J., Naylor, S., J. Chromatogr. B 1997, 697, 37-66.

[10] Guzman, N. A., Stubbs, R. J., Electrophoresis 2001, 22, 3602-3628.

[11] Guzman, N. A. LC.GC 1999, 17, 16-27.

[12] Pedersen-Bjergaard, S., Rasmussen, K. E., Electrophoresis 2000, 21, 579-585.

[13] Shaw, C. J., Guzman, N. A., in: Ohannesian, L., Streeter, A. J. (Eds.), Pharmaceutical Analysis, Marcel Dekker, New York 2002, Chapter 7, pp. 313-386.

[14] Guzman, N. A., Hoebel, B. G., Hernandez, L. BioPharm 1989, 2, 22-37.

[15] Guzman, N. A., U.S. Pat. No. 5,202,010, 13 Apr. 1993.

[16] Mariani, M., Camagna, M., Tarditi, L., Seccamani, E., Mol. Immunol. 1991, 28, 69-77.

[17] Yamaguchi, Y., Kim, H., Kato, K., Masuda, K., Shimada, I., Arata, Y., J. Immunol. Methods 1995, 181, 259-267.

[18] Akita, E. M., Nakai, S., J. Immunol. Methods 1993, 162, 155-164.

[19] Jones, R. G. A., Landon, J., J. Immunol. Methods 2002, 263, 57-74.

[20] Rea, D. W., Ultee, M. E., J. Immunol. Methods 1993, 157, 165-173.

[21] Wright, A., Morrison, S. L., TIB Tech. 1997, 15, 26-32.

[22] Lu, B., Smyth, M. R., O'Kennedy, R., Analyst 1996, 121, 29R-32R.

[23] Turkova, J., J. Chromatogr. B 1999, 722, 11-31.

[24] Peluso, P., Wilson, D. S., Do, D., Tran, H., Venkatasubbaiah, M., Quincy, D., Heidecker, B., Poindexter, K., Tolani., Phelan, M., Witte, K., Jung, L. S., Wagner, P., Nock, S., Anal. Biochem. 2003, 312, 113-124.

[25] Marchalonis, J. J., Adelman, M. K., Robey, I. F., Schluter, S. F., Edmundson, A. B., J. Mol. Recognit. 2001, 14, 110-121.

List of Other References

To be submitted in an Information Disclosure Statement.

U.S. PATENT DOCUMENTS:

| | | | |
|---|---|---|---|
| 5,045,172 | September 1991 | Guzman | 204/299 R |
| 5,202,010 | April 1993 | Guzman | 204/299 R |
| 5,246,577 | September 1993 | Fuchs et al. | 204/198.2 |
| 5,318,680 | June 1994 | Fishman et al. | 204/180.1 |
| 5,340,452 | August 1994 | Brenner et al. | 204/180.1 |
| 5,348,633 | September 1994 | Karger et al. | 204/180.1 |
| 5,413,686 | May 1995 | Klein et al. | 204/299 R |
| 5,439,578 | August 1995 | Dovichi et al. | 204/299R |
| 5,453,382 | September 1995 | Novotny et al. | 436/178 |
| 5,498,324 | March 1996 | Yeung et al. | 204/452 |
| 5,516,409 | May 1996 | Kambara | 204/603 |
| 5,560,811 | October 1996 | Briggs et al. | 204/451 |
| 5,730,850 | March 1998 | Kambara et al. | 204/603 |
| 5,741,639 | April 1998 | Ensing et al. | 435/6 |
| 5,800,692 | September 1998 | Naylor et al. | 204/601 |
| 5,958,202 | September 1999 | Regnier et al. | 204/451 |
| 6,007,690 | December 1999 | Nelson et al. | 204/601 |
| 6,010,607 | January 2000 | Ramsey | 204/435 |
| 6,010,608 | January 2000 | Ramsey | 204/453 |
| 6,020,208 | February 2000 | Hutchens et al. | 436/174 |
| 6,224,728 B1 | May 2001 | Oborny et al. | 204/450 |
| 6,387,234 B1 | May 2002 | Yeung et al. | 204/451 |
| 6,395,169 B1 | May 2002 | Hindsgaul et al. | 210/198.2 |
| 6,406,604 B1 | June 2002 | Guzman | 204/601 |
| 6,415,821 B2 | July 2002 | Kambolz et al. | 137/827 |
| 6,534,262 B1 | March 2003 | McKernan et al. | 435/6 |
| 6,544,396 B1 | April 2003 | Cong et al. | 204/601 |
| 6,554,986 B1 | April 2003 | Mathies et al. | 204/452 |
| 6,562,214 B1 | May 2003 | Amrhein et al. | 204/601 |
| 6,596,140 B2 | July 2003 | Nordman et al. | 204/452 |
| 6,613,212 B1 | September 2003 | Siebert et al. | 204/603 |
| 6,616,824 B1 | September 2003 | Tanaka | 204/603 |
| 6,627,453 B1 | September 2003 | Hindsgaul et al. | 436/161 |
| 6,635,164 B1 | October 2003 | Anazawa et al. | 204/603 |

FOREIGN PATENT DOCUMENTS

| | | |
|---|---|---|
| WO | WO 95/10344 | April 1995 |
| WO | WO 97/11362 | March 1997 |
| WO | WO 00/30751 | June 2000 |
| WO | WO 00/65354 | November 2000 |
| WO | WO 02/44703 A2 | June 2002 |
| WO | WO 02/48716 A2 | June 2002 |
| WO | WO 02/059592 A2 | August 2002 |
| WO | WO 03/027028 A1 | April 2003 |
| WO | WO 03/038424 A1 | May 2003 |
| WO | WO 03/048755 A1 | June 2003 |
| WO | WO 03/059935 A2 | July 2003 |
| WO | WO 03/087772 A2 | October 2003 |
| EP | EP 0 793 098 | September 1997 |
| EP | EP 1 048 950 A1 | November 2000 |
| EP | EP 1 048 951 A1 | November 2000 |
| EP | EP 0 666 980 B1 | May 2002 |
| EP | EP 1 357 378 A2 | October 2003 |

Other Publications

"Affinity Chromatography", Cuatrecasas and Anfinsen, Annual Review of Biochemistry 40, pp. 259-278. No month available (1971).

"Isotachophoresis Electrodesorption of Proteins from an Affinity Adsorbent on a Microscale", Kasicka and Prusik, Journal of Chromatography 273(1), pp. 117-128 (Mar. 11, 1983).

"Desorption Isotachophoresis—Quantitative Characterization of Sorption and Desorption Conditions", Kasicka and Prusik, Journal of Chromatography 320(1), pp. 75-80 (Feb. 22, 1985).

"The Use of a Concentration Step to Collect Urinary Components Separated by Capillary Electrophoresis and Further Characterization of Collected Analytes by Mass Spectrometry", Guzman et al., Journal of Liquid Chromatography 14(5), pp. 997-1015 (March 1991).

"Enzymophoresis of Nucleic Acids by Tandem Capillary Enzyme Reactor-Capillary Zone Electrophoresis", Nashabeh and Ziad El Rassi, Journal of Chromatography 596(2), pp. 251-264 (Apr. 10, 1992).

"Switching Valve with Internal Micro Precolumn for On-Line Sample Enrichment in Capillary Zone Electrophoresis", Debets et al., Journal of Chromatography 608(1-2), pp. 151-158 (Sep. 11, 1992).

"On-Line Peptide Mapping by Capillary Electrophoresis", Amankwa and Kuhr, Analytical Chemistry 65(19), pp. 2693-2697 (Oct. 1, 1993).

"Preparation and Evaluation of an On-Line Preconcentrator for Capillary Electrophoresis", Hoyt, Jr. et al., Journal of Microcolumn Separations 5(4), pp. 325-330, No month available (1993).

"On-Line Sample Preconcentration on a Packet-Inlet Capillary for Improving the Sensitivity of Capillary Electrophoresis of Pharmaceuticals", Swartz and Merion, Journal of Chromatography 632(1-2), pp. 209-213 (Feb. 19, 1993).

"Immunoaffinity Capillary Electrophoresis Analysis of Cyclosporin in Tears", Phillips and Chmielinska, Biomedical Chromatography 8(5), pp. 242-246 (September-October 1994).

"Optimization of On-Line Peptide Mapping by Capillary Zone Electrophoresis", Licklider and Kuhr, Analytical Chemistry 66(24), pp. 4400-4407 (Dec. 15, 1994).

"The Use of Solid Phase Concentrators for On-Line Preconcentration of Metallothionein Prior to Isoform Separation by Capillary Zone Electrophoresis", Beattie et al., Electrophoresis 16(3), pp. 322-328 (March 1995).

"Selective Preconcentration for Capillary Zone Electrophoresis Using Protein G Immunoaffinity Capillary Chromatography", Cole and Kennedy, Electrophoresis 16(4), pp. 549-556 (April 1995).

"Sensitivity Enhancement and Second-Dimensional Information from Solid Phase Extraction-Capillary Electrophoresis of Entire High-Performance Liquid Chromatography Fractions", Strausbauch et al., Electrophoresis 16(4), pp. 541-548 (April 1995).

"Michaelis-Menten analysis of immobilized enzyme by affinity capillary electrophoresis", Yoshimoto et al., Journal of Pharmaceutical and Biomedical Analysis 13(4-5), pp. 483-488 (April 1995).

"Biomedical Applications of On-Line Preconcentration-Capillary Electrophoresis Using an Analyte Concentrator: Investigation of Design Options", Guzman, Journal of Liquid Chromatography 18(11), pp. 3751-3768 (June 1995).

"Capillary enzymophoresis of nucleic acid fragments using coupled capillary electrophoresis and capillary enzyme microreactors having surface-immobilized RNA-modifying enzymes", Mechref and El Rassi, Electrophoresis 16(11), pp. 2164-2171 (November 1995).

"Immobilization of Antibodies as a Versatile Tool in Hybridized Capillary Electrophoresis", Ensing and Paulus, Journal of Pharmaceutical and Biomedical Analysis 14(3), pp. 305-316 (January 1996).

"On-Capillary Sample Preconcentration Incorporated in Chiral Capillary Electrophoresis", He et al., Analytical Sciences 12, pp. 177-181 (April 1996).

"Preconcentration and Microreaction Technology On-Line with Capillary Electrophoresis", Tomlinson et al., Journal of Chromatography A 744(1-2), pp. 3-15 (13 Sep. 1996).

"Protein Identification by Solid Phase Microextraction-Capillary Zone Electrophoresis-Microelectrospray-Tandem Mass Spectrometry", Figeys et al., Nature Biotechnology 14(11), pp. 1579-1583 (November 1996).

"Consecutive protein digestion and peptide derivatization employing an on-line analyte concentrator to map proteins using capillary electrophoresis", Guzman, In: Capillary Electrophoresis in Analytical Biotechnology (Edited by Pier Giorgio Righetti), CRC Series in Analytical Biotechnology, Chapter 4, pp. 101-121, CRC Press, Inc. Boca Raton, Fla. (1996, No month available).

"Identification of Proteins by Capillary Electrophoresis-Tandem Mass Spectrometry. Evaluation of an On-Line Solid-Phase Extraction Device", Figeys et al., Journal of Chromatography A 763(1-2), pp. 295-306 (28 Feb. 1997).

"High-Throughput DNA Sequencing on a Capillary Array Electrophoresis System", Marsh et al., Journal of Capillary Electrophoresis 4(2), pp. 83-89 (March-April 1997).

"New Approaches in Clinical Chemistry: On-Line Analyte Concentration and Microreaction Capillary Electrophoresis for the Determination of Drugs, Metabolic Intermediates, and Biopolymers in Biological Fluids", Guzman et al., Journal of Chromatography B 697(1-2), pp. 37-66 (Sep. 12, 1997).

"Automated Microanalysis Using Magnetic Beads with Commercial Capillary Electrophoresis Instrumentation", Rashkovetsky et al., Journal of Chromatography A, 781 (1-2), pp. 197-204 (26 Sep. 1997).

"A Novel m-ESI Source for Coupling Capillary Electrophoresis and Mass Spectrometry: Sequence Determination of Tumor Peptides at the Attomole Level", Settlage et al., Journal of Microcolumn Separation 10(3), pp. 281-285, No month available (1998).

"Analysis of Multiplexed Short Tandem Repeat (STR) Systems Using Capillary Array Electrophoresis", Mansfield et al., Electrophoresis 19(1), pp. 101-107 (January, 1998).

"A New Design for Large, Dilute Sample Loading in Capillary Electrophoresis", Barroso and de Jong, Journal of Capillary Electrophoresis 5(1-2), pp. 1-7 (January-February-March-April, 1998).

"Affinity Capillary Electrophoresis: A Physical-Organic Tool for Studying Interactions in Biomolecular Recognition", Colton et al., Electrophoresis 19(3), pp. 367-382 (March 1998).

"Survey of Recent Advances in Analytical Applications of Immunoaffinity Chromatography", Hage, Journal of Chromatography B 715(1), pp. 3-28 (Sep. 11, 1998).

"Affinity Capillary Electrophoresis: Important Application Areas and Some Recent Developments", Heegaard et al., Journal of Chromatography B 715(1), pp. 29-54 (Sep. 11, 1998).

"Recycling Immunoaffinity Chromatography for Multiple Analyte Analysis in Biological Samples", Phillips and Krum, Journal of Chromatography B 715(1), pp. 55-63 (Sep. 11, 1998).

"Nanoflow Solvent Gradient Delivery from a Microfabricated Device for Protein Identifications by Electrospray Ionization Mass Spectrometry", Figeys and Aebersold, Analytical Chemistry 70(18), pp. 3721-3727 (Sep. 15, 1998).

"Fabrication of Nanocolumns for Liquid Chromatography", He et al., Analytical Chemistry 70(18), pp. 3790-3797 (Sep. 15, 1998).

"Parallel Molecular Genetic Analysis", McKenzie et al., European Journal of Human Genetic 6(5), pp. 417-429 (September-October, 1998).

"Optimization of Solid Phase Microextraction-Capillary Zone Electrophoresis-Mass Spectrometry for High Sensitivity Protein Identification", Figeys et al., Electrophoresis 19(13), pp. 2338-2347 (October, 1998).

"Analysis of Recombinant Cytokines in Human Body Fluids by Immunoaffinity Capillary Electrophoresis", Phillips and Dickens, Electrophoresis 19(16-17), pp. 2991-2996 (November, 1998).

"Evaluation of Adsorption Preconcentration/Capillary Zone Electrophoresis/Nanospray Mass Spectrometry for Peptide and Glycoprotein Analyses", Bateman et al., Journal of Mass Spectrometry 33(11), pp. 1109-1123 (November, 1998).

"Precolumn Affinity Capillary Electrophoresis for the Identification of Clinically Relevant Proteins in Human Serum: Application to human Cardiac Troponin I", Dalluge and Sander, Analytical Chemistry 70(24), pp. 5339-5343 (Dec. 15, 1998).

"On-Line Bioaffinity, Molecular Recognition, and Preconcentration in CE Technology", Guzman, LC-GC 17(1), pp. 16-27 (January 1999).

"Capillary Array Electrophoresis DNA Sequencing", Kheterpal and Mathies, Analytical Chemistry 71(1), pp. 31A-37A (Jan. 1, 1999).

"Membrane Preconcentration CE", Yang et al., Analytical Chemistry 71(5), pp. 183A-189A (Mar. 1, 1999).

"An On-Line Preconcentrator and the Evaluation of Electrospray Interfaces for the Capillary Electrophoresis/Mass Spectrometry of Peptides", Herring and Qin, Rapid Communications in Mass Spectrometry 13(1), pp. 1-7, No month available (1999).

"SDS Capillary Electrophoresis of Proteins in Microfabricated Channels", Yao et al., Proceedings of the National Academy of Sciences USA 96(10), pp. 5372-5377 (May 11, 1999).

"Miniaturised on-line solid-phase extraction for enhancement of concentration sensitivity in capillary electrophoresis", Petersson et al., Journal of Chromatography A 841(2), pp. 241-261 (14 May 1999).

"On-line solid-phase preconcentration for sensitivity enhancement in capillary electrophoresis", Bonneil and Waldron, Journal of Capillary Electrophoresis 6(3-4), pp. 61-73 (May-August 1999).

"Monitoring the purity of a synthetic peptide by capillary electrophoresis: Utilization of an on-line preconcentration method for improved separation and detection sensitivity", Vizioli et al., Journal of Capillary Electrophoresis 6(3-4), pp. 109-118 (May-August 1999).

"Simultaneous Genetic Typing from Multiple Short Tandem Repeat Loci Using a 96-Capillary Array Electrophoresis System", Gao et al., Electrophoresis 20(7), pp. 1518-1526 (June 1999).

"Dynamic Hybridization on a Chip Using Paramagnetic Beads", Fan et al., Analytical Chemistry 71(21), pp. 4851-4859 (Nov. 1, 1999).

"Radial Capillary Array Electrophoresis Microplate and Scanner for High-Performance Nucleic Acid Analysis", Shi et al., Analytical Chemistry 71(23), pp. 5354-5361 (Dec. 1, 1999).

"Sheathless Preconcentration-Capillary Zone Electrophoresis-Mass Spectrometry Applied to Peptide Analysis", Begona Barroso and de Jong, Journal of the American Society for Mass Spectrometry 10(12), pp. 1271-1278 (December 1999).

"Characterization of a solid-phase extraction device for discontinuous on-line preconcentration in capillary electrophoresis-based peptide mapping", Bonneil and Waldron, Journal of Chromatography B 736(1-2), pp. 273-287 (Dec. 24, 1999).

"Strategies to improve the sensitivity in capillary electrophoresis for the analysis of drugs in biolical fluids", Toussaint et al., Electrophoresis 21(4), pp. 691-698 (March 2000).

"Mapping the phosphorylation sites of proteins using on-line immobilized metal affinity chromatography/capillary electrophoresis/electrospray ionization multiple stage tandem mass spectrometry", Cao and Stults, Rapid Communication Mass Spectrometry 14(17), pp. 1600-16006. No month available (2000).

"Packing columns for capillary electrochromatography", Colon et al., Journal of Chromatography A 887(1-2), pp. 43-53 (Jul. 28, 2000).

"Stationary phases for capillary electrochromatography", Pursch and Sander, Journal of Chromatography A 887(1-2), pp. 313-326 (Jul. 28, 2000).

"On-line preconcentration methods for capillary electrophoresis", Osbourn et al., Electrophoresis 21(14), pp. 2768-2779 (August 2000).

"Alternative methods providing enhanced sensitivity and selectivity in capillary electrophoresis", Schweitz et al., Journal of Chromatography A 892(1-2), pp. 203-217 (15 Sep. 2000).

"Electrochromatography", Smith and Carter-Finch, Journal of Chromatography A 892(1-2), pp. 219-255 (15 Sep. 2000).

"Advances in column technology and instrumentation in capillary electrochromatography", Pyell, Journal of Chromatography A 892(1-2), pp. 257-278 (15 Sep. 2000).

"Sample preconcentration by field amplification stacking for microchip-based capillary electrophoresis", Lichtenberg et al., Electrophoresis 22(2), pp. 258-271 (January 2001).

"Analysis of single-cell cultures by immunoaffinity capillary electrophoresis with laser-induced fluorescence detection", Phillips, Luminescence 16(2), pp. 145-152 (March-April 2001).

"Sol-gel technique for the preparation of beta-cyclodextrin derivative stationary phase in open-tubular capillary electrochromatography", Wang et al., Electrophoresis 22(11), pp. 2167-2172 (18 Jul. 2001).

"On-line sample preconcentration in capillary electrophoresis, focused on the determination of proteins and peptides", Stroink et al., Electrophoresis 22(12), pp. 2375-2383 (August 2001).

"Approaches to enhancing the sensitivity of capillary electrophoresis methods for the determination of inorganic and small organic anions", Breadmore and Haddad, Electrophoresis 22(12), pp. 2464-2489 (August 2001).

"Robust and cost-effective capillary electrophoresis-mass spectrometry interfaces suitable for combination with on-line analyte preconcentration", Waterval et al., Electrophoresis 22(13), pp. 2701-2708 (August 2001).

"Capillary electrophoretic bioanalysis of therapeutically active peptides with UV and mass spectrometric detection after on-capillary preconcentration", Waterval et al., Electrophoresis 22(13), pp. 2709-2716 (August 2001).

"The use of selective adsorbents in capillary electrophoresis-mass spectrometry for analyte preconcentration and microreactions: A powerful three-dimensional tool for multiple chemical and biological applications", Guzman and Stubbs, Electrophoresis 22(17), pp. 3602-3628 (October 2001).

"Sample preparation with fiber-in-tube solid-phase microextraction for capillary electrophoretic separation of tricyclic antidepressant drugs in human urine", Jinno et al., Electrophoresis 22(17), pp. 3785-3790 (October 2001).

"Exploiting lectin affinity chromatography in clinical diagnosis", Satish and Surolia, Journal of Biochemical and Biophysics Methods 49(1-3), pp. 625-640 (Oct. 30, 2001).

"On-line preconcentration in capillary electrochromatography using a porous monolith together with solvent gradient and sample stacking", Quirino et al., Analytical Chemistry 73(22), pp. 5557-5563 (Nov. 15, 2001).

"Sensitivity enhancement by on-line preconcentration and in-capillary derivatization for the electrophoretic determination of amino acids", Latorre et al., Electrophoresis 22(20), pp. 4355-4361 (December 2001).

"Improved method for pepsinolysis of mouse IgG(1) molecules to F(ab')$_2$ fragments", Wilson et al., Journal of Immunological Methods 260(1-2), pp. 29-36 (Feb. 1, 2002).

"Application of microfluidic devices to proteomics research: identification of trace level protein digests and affinity capture of target peptides", Li et al., Molecular & Cellular Proteomics 1(2), pp. 157-168 (February 2002).

"Toward a microchip-based solid-phase extraction method for isolation of nucleic acids", Wolfe et al., Electrophoresis 23(5): 727-733 (March 2002).

"Immunoaffinity screening with capillary electrophochromatography", Mayer et al., Electrophoresis 23(9), pp. 1255-1262 (May 2002).

"On-column ion-exchange preconcentration of inorganic anions in open tubular capillary chromatography with elution using transient-isotachophoretic gradients. 3. Implementation and method development", Breadmore et al., 74(9), 2112-2118 (May 1, 2002).

"On-line trypsin-encapsulated enzyme reactor by the sol-gel method integrated into capillary electrophoresis", Sakai-Kato et al., Analytical Chemistry 74(13): 2943-2949 (Jul. 1, 2002).

"Sweeping: Concentration mechanism and applications to high-sensitivity analysis in capillary electrophoresis", Quirino et al., Journal of Chromatography A 965(1-2), pp. 357-3773 (August 2002).

"On-chip chromatography: the last twenty rears", de Mello, Lab on a Chip 2(3), pp. 48N-54N (August 2002).

"A new type of capillary column for open-tubular electrochromatography", Zhao et al., Electrophoresis 23(17), pp. 2990-2995 (September 2002).

"On-line drug metabolism system using microsomes encapsulated in a capillary by sol-gel method and integrated into capillary electrophoresis", Sakai-Kato et al., Analytical Biochemistry 308(2), pp. 278-284 (Sep. 15, 2002).

"An integrated solid-phase extraction system for sub-picomolar detection", Jemere et al., Electrophoresis 23(20), pp. 3537-3544 (October 2002).

"Integration of solid-phase extraction membranes for sample multiplexing: application to rapid protein identification from gel-isolated protein extracts", Bonneil et al., Electrophoresis 23(20), pp. 3589-3598 (October 2002).

"Advances in sol-gel based columns for capillary electrochromatography: sol-gel open-tubular columns", Malik, Electrophoresis 23(22-23), pp. 3973-3992 (November 2002).

"Integration of on-column immobilized enzyme reactor in microchip electrophoresis", Park et al., Electrophoresis 24(1-2), pp. 200-206 (January 2003).

"Recent developments in protein microarray technology", Wilson and Nock, Angew Chem Int Ed English 42(5), pp. 494-500 (Feb. 3, 2003).

"On-chip coupling of isoelectric focusing and free solution electrophoresis for multidimensional separations", Herr et al., Analytical Chemistry 75(5), pp. 1180-1187 (Mar. 1, 2003).

"Analysis of intracellular regulatory proteins by immunoaffinity capillary electrophoresis coupled with laser-induced fluorescence detection", Biomedical Chromatography 17(2-3), pp. 182-187 (March 2003).

"Immuno-based sample preparation for trace analysis", Hennion and Pichon, Journal of Chromatography A 1000 (1-2), pp. 29-52 (Jun. 6, 2003).

"Silica gel-based monoliths prepared by the sol-gel method: facts and figures", Siouffi, Journal of Chromatography A 1000(1-2), pp. 801-818 (Jun. 6, 2003).

"On-line preconcentration strategies for trace analysis of metabolites by capillary electrophoresis", Britz-McKibbin and Terabe, Journal of Chromatography A 1000(1-2), pp. 917-934 (Jun. 6, 2003).

"Small structures fabricated using ash-forming biological materials as templates", Kim, Biomacromolecules 4(4), pp. 908-913 (July-August 2003).

"On-line preconcentration in capillary electrophoresis using monolithic methacrylate porous", Baryla and Toltl, Analyst 128(8), pp. 1009-1012 (August 2003).

"Capillary electrochromatography and preconcentration of neutral compounds on poly(dimethylsiloxane) microchips", Ro et al., Electrophoresis 24(18), pp. 3253-3259 (September 2003).

"Preparation of hollow silica microspheres in W/O emulsions with polymers", Park et al., Journal of Colloid and Interface Science 266(1), pp. 107-114 (Oct. 1, 2003).

"Fluidic preconcentrator device for capillary electrophoresis of proteins", Astorga-Wells and Swerdlow, Analytical Chemistry 75(19), pp. 5207-5212 (Oct. 1, 2003).

"A microfluidic electrocapture device in sample preparation for protein analysis by MALDI spectrometry", Astorga-Wells et al., Analytical Chemistry 75(19), pp. 5213-5219 (Oct. 1, 2003).

"The 'right' size in nanobiotechnology", Whitesides, Nature Biotechnology 21(10), pp. 1161-1163 (October 2003).

"Fabrication of novel biomaterials through molecular self-assembly", Zhang, Nature Biotechnology 21(10), pp. 1171-1178 (October 2003).

"Integrated nanoliter systems", Hong and Quake, Nature Biotechnology 21(10), pp. 1179-1183 (October 2003).

"Small-scale systems for in vivo drug delivery", La Van et al., Nature Biotechnology 21(10), pp. 1184-1191 (October 2003).

"Electrochemical DNA detectors", Drummond et al., 21(10), Nature Biotechnology 21(10), 1192-1199 (October 2003).

"Low-attomole electrospray ionization MS and MS/MS analysis of protein tryptic digests using 20-μm-i.d. polystyrene-divinylbenzene monolithic capillary columns", Ivanov et al., Analytical Chemistry 75(20), pp. 5306-5316.

"Dual-function microanalytical device by in situ photolithographic grafting of porous polymer monolith: Integrating solid-phase extraction and enzymatic digestion for peptide mass mapping", Peterson et al., Analytical Chemistry 75(20), pp. 5328-5335 (Oct. 15, 2003).

"Phosphoprotein isotope-coded solid-phase tag approach for enrichment and quantitative analysis of phosphopeptides from complex mixtures", Qian et al., Analytical Chemistry 75(20), pp. 5441-5450 (Oct. 15, 2003).

"Development of a poly(dimethylsiloxane) interface for on-line capillary column liquid chromatography-capillary electrophoresis coupled to sheathless electrospray ionization time-of-flight mass spectrometry", Bergstrom et al., Analytical Chemistry 75(20), pp. 5461-5467 (Oct. 15, 2003).

"Chip-based solid-phase extraction pretreatment for direct electrospray mass spectrometry analysis using an array of monolithic columns in a polymeric substrate", Tan et al., Analytical Chemistry 75(20), pp. 5504-5511 (Oct. 15, 2003).

"Biochemical analisis with microfluidic systems", Bilitewski et al., Analytical and Bioanalytical Chemistry 377 (3), pp. 556-569 (October 2003).

"The puzzle of the proteome", Willis, Modern Drug Discovery 6(10), pp. 26-30 (October 2003).

What is claimed is:

1. A disease detection system, comprising:
an electrophoresis apparatus including: (a) a transport passage; (b) a plurality of separation passages, each of the separation passages having a separation passage overlapping portion that overlaps a different portion of the transport passage, each intersection of each of the separation passages with the transport passage has a staggered configuration of the transport passage having an elongated separation passage portion that forms the respective separation passage overlapping portion where the transport passage and the separation passages connect at two separate and distinct points, the plurality of separation passages being separate and independently communicable upstream of the respective overlapping portions with a biomarker separation buffer supply or with a supply of a biomarker elution buffer or solution; (c) a different biomarker concentrator in each of the overlapping portions that isolates and concentrates a different biomarker from a specimen from an animal introduced into an inlet end of the transport passage; a first set of the different biomarkers being associated with a first disease and a different second set of the biomarkers being associated with a second disease, each of the biomarker concentrators includes at least one affinity ligand capable of attracting the respective different biomarker from the specimen; and (d) a a valve system operable at least in part to control fluid flow through the transport passage from the inlet end of the transport passage to an outlet end of the transport passage and from the separation passages to a biomarker detection zone;
the valve system controlling the flow of a biomarker separation buffer in the separation passages introduced from the biomarker separation buffer supply or a plug of a biomarker elution buffer or solution in the separation passages introduced from the biomarker elution buffer supply in a sequential order from an inlet end of the respective separation passages to an outlet end of the respective separation passages,
the valve system comprises a first valve in the transport passage upstream of one of the staggered configurations, a second valve in the transport passage downstream of one of the staggered configurations, a third valve in the separation passage associated with one of the staggered configurations and upstream of one of the staggered configurations and a fourth valve in the separation passage and downstream of one of the staggered configurations, the third valve and the fourth valve of the valve system being selectively operable in a first disease mode wherein biomarkers associated with the first disease are released from a first set of the biomarker concentrators for delivery to the detection zone and in an alternative second disease mode wherein biomarkers associated with the second disease are released from a second set of the biomarker concentrators for delivery to the detection zone;

a memory having reference data corresponding to the first and second diseases; and a CPU that controls the operation of the electrophoresis apparatus in both the first and second disease modes and compares data relative to the biomarkers detected at the biomarker detection zone with the reference data, the CPU can transmit data detected in the detection zone over the Internet to an evaluator; and the CPU can receive from the evaluator feedback relative to the first and/or second disease.

2. The system of claim 1 wherein each of the passages is a capillary.

3. The system of claim 1 further comprising an updatable memory operatively connected to the CPU and positioned remote from the CPU.

4. The system of claim 1 wherein the first set and the second set overlap and both include at least one same biomarker concentrator and separation passage associated therewith during operation of the electrophoresis apparatus in the first disease mode and the second disease mode.

5. The system of claim 1 wherein the biomarker detection zone comprises a single and/or a plurality of simultaneously operating detectors, wherein the detectors obtain different qualitative, quantitative and structural information from the released biomarkers.

6. The system of claim 1 wherein the biomarker elution buffer or solution contains an appropriate chromophoric reagent to elute and label the bound biomarker simultaneously.

7. The system of claim 1 wherein the valves allow cleaning, washing, conditioning, separation solution and the elution buffer or solution to pass sequentially through each of the separation passages at controlled times towards the biomarker detection zone, and the valves allow the corresponding released and concentrated biomarkers to pass through each of the separation passages towards the biomarker detection zone.

8. The system of claim 1 wherein:

the electrophoresis apparatus includes a platform;

the plurality of separation passages defines a first set of separation passages and a second set of separation passages;

the biomarker concentrators define a first set of biomarker concentrators associated with a first predetermined disease and a second set of biomarker concentrators associated with a second predetermined disease;

the first set of separation passages and the first set of biomarker concentrators form a first modular unit;

the second set of separation passages and the second set of biomarker concentrators form a second modular unit; and the first and second modular units are alternatively positionable in operative positions supported by the platform.

9. The system of claim 1 wherein each of the biomarker concentrators is a biomarker concentrator-microreactor having a plurality of immobilized affinity-capture ligands and/or a plurality of immobilized affinity-reactor ligands.

10. The system of claim 1 wherein an additional analyte concentrator containing a chromophoric reagent to react with the at least one different biomarker is placed in one or more of the separation passages.

11. The system of claim 1 wherein the transport passage is adapted to perform isoelectric focusing separation of a sample solution of the specimen.

12. The system of claim 1, wherein the biomarker concentrator-microreactor device comprises an extra port or filling port to replace the matrix positioned within the concentrator-microreactor device or to add appropriate buffer or medium to cell or subcellular structures positioned within the concentrator-microreactor device.

13. The system of claim 1 further comprising an ultraviolet, fluorescent, phosphorescent, chemiluminescent, laser-induced fluorescent, circular dichroism, electrochemical, and/or mass spectrometer biomarker detector at the detection zone.

14. The system of claim 1 wherein the biomarkers comprise at least one of cells, peptides, oligo-nucleotides, oligo-saccharides, or lipids.

15. The system of claim 1 wherein biomarkers released from the biomarker concentrators into the separation passages are delivered to the detection zone by electrophoresis, electro-osmotic flow, mechanical pressure or a combination of electro-osmotic flow and mechanical pressure.

16. The system of claim 1 further comprising a plurality of simultaneously operating detectors in the detection zone, each of the detectors obtaining different qualitative, quantitative, and/or structural information from the released and separated biomarkers.

17. The system of claim 1 further comprising only a single detector in the detection zone to obtain qualitative, quantitative, and/or structural information from the released biomarkers.

18. The system of claim 1 wherein the inlet end of the transport passage can be alternatively in fluid communication with a supply of a cleaning solution, a supply of a conditioning buffer, a supply of the specimen and a supply of a washing solution.

19. The system of claim 1 wherein the valve system allows cleaning, washing, conditioning, separation solutions and the elution buffer or solutions, as well as corresponding released concentrated biomarkers of interest, to pass sequentially through each of the separation passages towards the detection zone.

20. The system of claim 1 wherein the valve system allows cleaning and conditioning buffers followed by a sample specimen and a washing solution to pass sequentially from an inlet through an outlet of the transport passage towards a waste container.

21. The system of claim 1 wherein the electrophoresis apparatus includes:

a first auxiliary buffer passage through which a separation buffer can be provided to a first one of the separation passages, downstream of a first one of the biomarker concentrators and upstream of the biomarker detector; and a second auxiliary buffer passage through which a separation buffer can be provided to a second one of the separation passages, downstream of a second one of the biomarker concentrators and upstream of the biomarker detector.

22. The system of claim 1 wherein each of the biomarker concentrators is a biomarker concentrator-microreactor having a plurality of immobilized affinity ligands and/or a plurality of immobilized affinity-reactor ligands.

23. The system of claim 1 wherein each of the passages is a capillary or is at least in substantial part a channel.

24. The system of claim 1 wherein each of the passages is at least in substantial part a channel.

25. The system of claim 1 wherein the separation passages have an independently controlled temperature system.

26. The system of claim 1 wherein the valves are microvalves.

27. The system of claim 1 wherein the CPU controls operating of said valves.

28. The system of claim 1 wherein the valves allow cleaning, washing and conditioning buffers or solutions to pass through the transport capillary or passage, from the inlet end to the outlet end of the transport capillary to a waste container, passing through each biomarker concentrator-microreactor device, allowing a cycle of analysis to be completed for each separation capillary, followed by a recycling process to start another cycle of analysis.

29. The system of claim 1 wherein the immobilized affinity ligands within the biomarker concentrator-microreactor device can be re-used multiple times allowing frequent biomarker determination for early detection of a disease and permitting the monitoring of disease progression or prognosis and the effect of medication.

30. The system of claim 1 wherein the at least one affinity ligand can be covalently or non-covalently attached to microstructures positioned within the biomarker concentrator-microreactor or directly to an inner wall of the biomarker concentrator-microreactor.

31. The system of claim 30 wherein the at least one affinity ligand attached covalently or non-covalently to the microstructures positioned within the concentrator-microreactor or directly to the inner wall of the biomarker concentrator-microreactor can be bound or immobilized in various configurations and orientations.

32. The system of claim 30 wherein the at least biomarkers captured by the one or more affinity ligands immobilized to the matrix positioned within the biomarker concentrator-microreactor or directly to the inner wall of the biomarker concentrator-microreactor can be released simultaneously as a group or one or more at a time stepwise or sequentially.

33. The system of claim 30 wherein the binding of the at least one biomarker to the one or more of the immobilized affinity ligands can be optimized by the use of gently shaking, microwave pulse or acoustic micromixing system.

34. The system of claim 30 wherein the binding of the at least one biomarker to the one or more of the immobilized affinity ligands can be optimized by the use of an appropriate temperature, time of interaction, and pH of the buffer.

35. The system of claim 30 wherein the affinity ligands immobilized to the inner wall of the biomarker concentrator-microreactor can be used to capture small molecules, polymeric structures, biomolecules, cells, organelles, and/or globular structures.

36. The system of claim 1 wherein the specimen is a biological fluid, urine, blood, saliva, breath, sweat, cerebrospinal fluid, hair, nail, tissue or cell extract from the animal.

37. The system of claim 10 wherein the animal is a human being.

38. The system of claim 10 wherein the evaluator is a medical specialist.

39. The system of claim 38 wherein the medical specialist is positioned remote from the electrophoresis apparatus.

* * * * *